US012150956B2

(12) United States Patent
Anyarambhatla et al.

(10) Patent No.: US 12,150,956 B2
(45) Date of Patent: *Nov. 26, 2024

(54) TRACE ELEMENT COMPOSITIONS, METHODS OF MAKING AND USE

(71) Applicant: American Regent, Inc., Shirley, NY (US)

(72) Inventors: Gopal Anyarambhatla, New Albany, OH (US); Richard Lawrence, Southold, NY (US); Jasmina Marinkovic, East Setauket, NY (US)

(73) Assignee: American Regent, Inc., Shirley, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/653,608

(22) Filed: May 2, 2024

(65) Prior Publication Data

US 2024/0299447 A1 Sep. 12, 2024

Related U.S. Application Data

(60) Continuation of application No. 18/482,612, filed on Oct. 6, 2023, now Pat. No. 11,975,022, which is a division of application No. 17/365,695, filed on Jul. 1, 2021, now Pat. No. 11,786,548.

(60) Provisional application No. 63/047,708, filed on Jul. 2, 2020.

(51) Int. Cl.
| | |
|---|---|
| *A61K 33/30* | (2006.01) |
| *A61K 9/00* | (2006.01) |
| *A61K 31/7004* | (2006.01) |
| *A61K 33/00* | (2006.01) |
| *A61K 33/04* | (2006.01) |
| *A61K 33/06* | (2006.01) |
| *A61K 33/22* | (2006.01) |
| *A61K 33/24* | (2019.01) |
| *A61K 33/32* | (2006.01) |
| *A61K 33/34* | (2006.01) |
| *A61K 47/10* | (2017.01) |
| *A61K 47/20* | (2006.01) |
| *A61P 3/02* | (2006.01) |

(52) U.S. Cl.
CPC ............ *A61K 33/30* (2013.01); *A61K 9/0029* (2013.01); *A61K 31/7004* (2013.01); *A61K 33/00* (2013.01); *A61K 33/04* (2013.01); *A61K 33/06* (2013.01); *A61K 33/22* (2013.01); *A61K 33/24* (2013.01); *A61K 33/32* (2013.01); *A61K 33/34* (2013.01); *A61K 47/10* (2013.01); *A61K 47/20* (2013.01); *A61P 3/02* (2018.01)

(58) Field of Classification Search
CPC ........ A61K 33/00; A61K 33/30; A61K 33/04; A61K 33/06; A61K 33/11; A61K 33/24; A61K 33/32; A61K 33/16; A61K 33/18; A61K 9/0029; A61K 31/7004; A61K 47/10; A61K 47/20; A61K 47/02; A61K 2300/00; A61P 3/02; Y02A 50/30

See application file for complete search history.

(56) References Cited

U.S. PATENT DOCUMENTS

| | | | |
|---|---|---|---|
| 5,993,863 | A | 11/1999 | Kikuchi et al. |
| 6,844,012 | B1 | 1/2005 | Forceville |
| 7,022,351 | B2 | 4/2006 | Abdel-Monem et al. |
| 11,510,941 | B1 | 11/2022 | Maloney et al. |
| 11,786,548 | B2 | 10/2023 | Anyarambhatla et al. |
| 11,975,022 | B2 * | 5/2024 | Anyarambhatla ..... A61K 47/20 |
| 2018/0296599 | A1 | 10/2018 | Smith |
| 2021/0069138 | A1 | 3/2021 | Pinoie et al. |
| 2022/0000766 | A1 | 1/2022 | Lawrence et al. |
| 2023/0302047 | A1 | 9/2023 | Anyarambhatla et al. |
| 2024/0058378 | A1 | 2/2024 | Anyarambhatla et al. |

FOREIGN PATENT DOCUMENTS

| | | |
|---|---|---|
| CN | 105521481 A | 4/2016 |
| KR | 20200077462 A | 6/2020 |
| KR | 102295585 B1 | 8/2021 |
| WO | 2019/211605 A1 | 11/2019 |

OTHER PUBLICATIONS

Selenious Acid Injection, USP. Product Information Bulletin. Jun. 2019.
Selenious Acid Injection—6 mcg/mL of Selenium, Package Insert, American Regent Mar. 2022.
Selenious Acid Injection—60 mcg/ml of Selenium, Package Insert, American Regent Oct. 2019.
American Regent Announces the Launch and Availability of Selenious Acid Injection, USP, Jul. 10, 2019.
Menendez, Ana M., et al., Iron Contamination in Parenteral Nutrition Mixtures—Full Abstract, Bibloteca.ub.edu.ar, Nov. 14, 2017.
Pluhator-Murton, Michelle M. et al., Trace Element Contamination of Total Parenteral Nutrition. 1. Contribution of Component Solutions, Journal of Parenteral and Enteral Nutrition, vol. 23, No. 4, Jul.-Aug. 1999.
Poole, Robert L., et al., Aluminum Exposure in Neonatal Patients using the Least Contaminated Parenteral Nutrition Solution Products, Nutrients.Nov. 2012; 4(11): 1566-1574.
Selenium Injection, 40 Mcg, package insert, American Regent, Aug. 2018.

(Continued)

*Primary Examiner* — Tracy Liu
(74) *Attorney, Agent, or Firm* — Sorell, Lenna & Schmidt, LLP

(57) ABSTRACT

Injectable compositions that can be added to parenteral nutrition are provided. In particular, a stable injectable composition is provided which includes water, and at least one of about 800 µg to about 4,000 µg of zinc, about 40 µg to about 400 µg of copper, from about 4 µg to about 90 µg of selenium, or from about 1 µg to about 80 µg of manganese per 1 mL of the injectable composition. Methods of preparing and using of the stable injectable composition are also provided.

30 Claims, No Drawings

(56) References Cited

OTHER PUBLICATIONS

Selepen (Selenium IV Additive for use with TPN), Product Monograph, Pharmaceutical Partners of Canada, Inc., Jan. 15, 2008.
Unapproved Drugs, www.fda.gov/drugs/enforcement-activities-fda/unapproved-drugs, Oct. 17, 2019.
M.T.E-6 Concentrated, Product Monograph, Pharmaceutical Partners of Canada, Inc., Jan. 15, 2008.
Moukarzel, Adib. Chromium in Parenteral Nutrition: Too Little or Too Much? Gastroenterology. 2009; vol. 137: S18-S28.
Hardy, Gil, et al. Trace element supplementation in parenteral nutrition: Pharmacy, posology, and monitoring guidance. Nutrition. vol. 25 (2009) 1073-1084.
European Medicines Agency, Committee for Medicinal Products for Human Use. Guideline on the Specification Limits for Residues of Metal Catalysts or Metal Reagents. London. Feb. 21, 2008.
Sriram, K. and Lonchyna, V. Micronutrient Supplementation in Adult Nutrition Therapy: Practical Considerations. Journal of Parenteral and Enteral Nutrition. 2009. vol. 33: 548. May 19, 2009.
Parrish, Carol R. Trace Element Monitoring and Therapy for Adult Patients Receiving Long-term Total Parenteral Nutrition. Nutrition Issues in Gastroenterology, Series #25. Practical Gastroenterology. Mar. 2005.
Mirtallo, Jay, et al. Safe Practices for Parenteral Nutrition. Journal of Parenteral and Enteral Nutrition. 2004. vol. 28, No. 6: S39.
Fessler, Theresa A. Trace Elements in Parenteral Nutrition: A Practical Guide for Dosage and Monitoring in Adult Patients. Nutrition in Clinical Practice. 2013. vol. 28, No. 6. Dec. 2013. 722-729.
Fresenius Kabi USA LLC. Adult Multi-Trace Element Availability. Letter to Healthcare Professionals.
Baptista et al. Utilizing selenious acid to reverse selenium deficiency in total parenteral nutrition patients. Am. J. Clin. Nutr. (1984); 39(5):816-820, 819.
Highlights of Prescribing Information, KABIVEN (amino acids, eletrolytes, dextrose and lipid injectable emulsion) for Intravenous use, Rev. Apr. 2016, Fresenius Kabi, Uppsala, Sweden.
Lipinski, B., Sodium Selenite as an Anticancer Agent. Anticancer Agents Med Chem. (2017) 17(5): 658-661.
Health Products Regulatory Authority. Summary of Product Characteristics. Additrace, concentrate for solution for infusion. Mar. 2020.
Highlights of Prescribing Information and Full Prescribing Information—Clinimix E (amino acids with electrolytes in dextrose with calcium) injection for intravenous use. Rev. Sep. 2016. Baxter Healthcare Corp., Deerfield, IL. 60015 U.S.A.
Allingstrup, M., Afshari, A., Selenium supplementation for critically ill adults (Review). Cochrane Database of Systematic Reviews. John Wiley & Sons, Ltd. 2016.
Brodin, Ola, et al. Pharmacokinetics and Toxicity of Sodium Selenite in the Treatment of Patients with Carcinoma in a Phase I Clinical Trial: The SECAR Study. Nutrients (2015) vol. 7, 4978-4994.
Health Products Regulatory Authority, Summary of Product Characteristics. Peditrace, concentrate for solution for infusion. Apr. 2019.
Song, Mihae, et al. Phase I trial of selenium plus chemotherapy in gynecologic cancers. Gynecologic Oncology (2018) vol. 150, pp. 478-486. Elsevier Inc.
Power-Burns, Melanie. Pediatric Multi-Trace Element Availability. Fresenius Kabi. May 29, 2013.
Package Leaflet: Information for the Patient Additrace® Concentrate for Solution for Infusion. HPRA Pharmacovigilance. Earlsfort Terrace, Dublin, Ireland. Mar. 14, 2019.
Summary of Product Characteristics. Peditrace Concentrate for Infusion Solutions. Fresenius Kabi AB SE-751 74 Uppsala, Sweden. May 13, 2009.
Cupric Sulfate Injection. Rev. Jan. 2009. American Regent, Inc., Shirley, New York 11967. Drugs.com.
Package insert. Selenium Injection. Rev. Aug. 2018. American Regent, Inc., Shirley, New York 11967.
Package insert. Baxter Infuvite Adult Multiple Vitamins for Infusion. Rev. May 2004. Baxter Healthcare Corporation, Deerfield, IL 60015 USA.
Package Insert. Manganese Sulfate Injection USP. Rev. Jan. 2009. American Regent, Inc., Shirley, New York 11967.
Package insert "Highlights of Prescribing Information" Zinc Sulfate Injection. Rev. Oct. 2019. American Regent, Inc., Shirley, New York 11967.
Prescribing information. Infed(R) Iron Dextran Injection USP. Nov. 2018. Retrieved from Internet URL: https://dailymed.nlm.nih.gov/fda.
Prescribing information. Intralipid(R) 20%. A 20% I.V. Fat Emulsion. Jun. 2006. Retrieved from Internet URL: https://www.accessdata.fda.gov/drugsatfda_docs/label/2007/017643s072,018449s039lbl.pdf.
Prescribing Information. 50% Dextrose Injection, USP; 70% Dextrose Injection, USP. Rev. Nov. 21, 2018. Baxter Corporation, Mississauga, on L5N 0C2.
Product Monograph. Travasol E with electrolytes and Travasol injection. Nov. 3, 2016. Baxter Corporation, Mississauga, ON L5N 002.
International Council for Harmonisation of Technical Requirements for Pharmaceuticals for Human Use. ICH Harmonised Guideline. Guideline for elemental impurities. Q3D(R1) Final Version Mar. 22, 2019.
U.S. Department of Health and Human Services, Food and Drug Administration, Center for Drug Evaluation and Research (CDER), Center for Biologics Evaluation and Research (CBER). Q3D(R1) Elemental Impurities Guidance for Industry. Mar. 2020. ICH. Revision I.
Vanek, Vincent W., et al. "ASPEN position paper: recommendations for changes in commercially available parenteral multivitamin and multi-trace element products." Nutrition in Clinical Practice 27.4 (2012): 440-491. (Year: 2012).
Selenious Acid—Product Information Bulletin. Jun. 2019. American Regent, Inc., Shirley, NY.
Highlights of Prescribing Information—Selenious Acid Injection. Aug. 2021. American Regent, Inc., Shirley, NY.
Highlights of Prescribing Information—Selenious Acid Injection. Rev. Apr. 2019. American Regent, Inc., Shirley, NY.
Copper 0.4 mg/mL Cupric Chloride Injection, USP. Rev. Apr. 2021. Distributed by Hospira, Inc., Lake Forest, IL.
Zinc 1 mg/ml Zinc Chloride Injection, USP. Rev. Jul. 2020. Distributed by Hospira, Inc., Lake Forest, IL.
Manganese 0.1 mg/ml Manganese Chloride Injection, USP. Rev. Nov. 2009. Distributed by Hospira, Inc., Lake Forest, IL.
Allwood, M.C. and Kearney, M.C. "Compatibility and stability of additives in parenteral nutrition admixtures," Nutrition. Sep. 1998 vol. 14. No. 9. pp. 697-706.
Munoz, P. G., et al. "Influence of the type of amino acids in the formation of precipitates of copper and sulphur in parenteral nutrition," Nutr Hosp. Aug. 26, 2019. vol. 36. No. 4. pp. 764-768.
Miller, Sarah J. "Parenteral Nutrition," U.S. Pharmacist. Jul. 20, 2006, vol. 7: HS-10-HS-20.
Sacks, Gordon S. and Driscoll, David F. "Does Lipid Hang Time Make a Difference? Time Is of the Essence," Clinical Controversies. Nutrition in Clinical Practice. vol. 17. Oct. 2002. pp. 284-290.
Nesheim, Malden C. "Dietary Supplements," Nutrition. vol. 14, No. 9, pp. 729-730. 1998.
Mirtallo, J., et al. "Safe Practices for Parenteral Nutrition," Journal of Parenteral and Enteral Nutrition. vol. 28, No. 6. Nov.-Dec. 2004, pp. S39-S70.
Pluhator-Murton, Michelle M., et al. "Trace Element Contamination of Total Parenteral Nutrition. 1. Contribution of Component Solutions," Journal of Parenteral and Enteral Nutrition. vol. 23, Issue No. 4, Jul. 1999. Abstract.
Perks, Patti, et al. "Advances in Trace Element Supplementation for Parenteral Nutrition," Nutrients 2022, 14, 1770.
O'Grady, Naomi, et al. "Guidelines for the Prevention of Intravascular Catheter-Related Infections," CDC MMWR Recommendations and Reports. Aug. 9, 2002 / 51 (RR10); 1-26.

(56) References Cited

OTHER PUBLICATIONS

Olson, Logan M., et al. "Quantitative Assessment of Trace Element Contamination in Parenteral Nutrition Components," Journal of Parenteral and Enteral Nutrition. vol. 43, Issue No. 8, Nov. 2019. Abstract.

Postaire E., et al. "Stability and behaviour of selenium in total parenteral nutrition solutions", International Journal of Pharmaceutics, Elsevier, NL, vol. 55, No. 2-3, Oct. 15, 1989 (Oct. 15, 1989), pp. 99-103, XP025829115.

Manning R.J., et al. "Chemical stability of total parenteral nutrition mixtures", International Journal of Pharmaceutics, Elsevi ER, NL, vol. 81, No. 1, Mar. 15, 1992 (Mar. 15, 1992) pp. 1-20, XP025544259.

PCT International Search Report and Written Opinion of the International Searching Authority (EPO) dated Oct. 18, 2021, issued in International PCT Application No. PCT/US2021/040133 filed Jul. 1, 2021.

PCT International Search Report and Written Opinion of the International Searching Authority (EPO) dated Oct. 18, 2021, Issued in International PCT Application No. PCT/US2021/040135 filed Jul. 1, 2021.

Vanek, Vincent W., et al. A.S.P.E.N. Position Paper: Recommendations for Changes in Commercially Available Parenteral Multivitamin and Multi-Trace Element Products. Nutrition in Clinical Practice. vol. 27 No. 4, Aug. 2012.

Highlights of Prescribing Information. KABIVEN (amino acids, electrolytes, dextrose and lipid injectable emulsion) for intravenous use. Rev. Oct. 2016. Fresenious Kabi. Upsala, Sweden.

Package Insert. Multitrace® 4—Concentrate (Trace Elements Injection 4, USP) for IV Use After Dilution—Rx Only. Rev. Aug. 2018. American Regent, Inc., Shirley, NY 11967.

Package Insert. Multitrace® 5—Concentrate (Trace Elements Injection 5, USP) for IV Use After Dilution—Rx Only. Rev. Aug. 2018. American Regent, Inc., Shirley, NY 11967.

Parenteral Nutrition—an overview | ScienceDirect Topics. (list of abstracts of publications). Retrieved from the Internet on May 8, 2020 from URL https://www.sciencedirect.com/topics/medicine-and-dentistry/parenteral-nutrition.

A.S.P.E.N. Parenteral Nutrition Safety Consensus Recommendations. Journal of Parenteral and Enteral Nutrition. JPEN J Parenter Enteral Nutr published online Nov. 26, 2013. URL http://pen.sagepub.com/content/early/2013/11/19/0148607113511992. Sage Publications on behalf of the American Society of Parenteral & Enteral Nutition.

Amin, H., et al. Manganese Toxicity Complicating Parenteral Nutrition. American Journal of Therapeutics 0, 1-2 (2019). Wolters Kluwer Health, Inc.

Chalela, Julio A., et al. Manganese Encephalopathy: An Under-Recognized Condition in the Intensive Care Unit. Neurocrit Care (2011) 14:456-458.

Derelanko, M. J., et al. Thirteen-Week Subchronic Rat Inhalation Toxicity Study with a Recovery Phase of Trivalent Chromium Compounds, Chromic Oxide, and Basic Chromium Sulfate. Toxicological Sciences. vol. 52, 278-288, 1999.

Powers-Burns, M. Adult Multi-Trace Element Availability. (Announcement) Fresenius Kabi USA, LLC. Lake Zurich, Illinois. May 29, 2013.

Lin, Jennifer, et al. Trace Elements in Parenteral Nutrition: Considerations for the Prescribing Clinician. Nutrients. vol. 9, No. 440, 2017.

Prescribing Information. M.V.I.-12 (Multi-Vitamin Infusion without vitamin K). Rev. Apr. 2004. aaiPharma, Wilmington, NC 28405. 14 pages.

Takagi, Yoji, et al. Evaluation of indexes of in vivo manganese status and the optimal intravenous dose for adult patients undergoing home parenteral nutrition. Am J Clin Nutr 2002;75:112-8.

Walter, E., et al. Manganese Toxicity in Critical Care: Case report, literature review and recommendations for practice. Journal of the Intensive Care Society. 2016. vol. 17, No. 3, 252-257.

Package Insert. Chromium Chloride Injection, USP. Rev. Jan. 2009. American Regent, Inc. Shirley, NY 11967.

Toxicological Profile for Chromium. U.S. Department of Health and Human Services. Sep. 2012. 592 pages.

Vincent, John B., The Biochemistry of Chromium. Recent Advances in Nutritional Sciences. 2000 American Society for Nutritional Sciences.

Opinion of the Scientific Committee on Food on the Tolerable Upper Intake Level of Trivalent Chromium. Scientific Committee on Food. European Commssion—Health & Consumer Protection Directorate General. Apr. 23, 2003.

Liden, S., et al. Penetration of Chromium in Intact Human Skin in vivo. Journal of Investigative Dermatology, vol. 72, No. 1, pp. 42-45. 1979. The Williams & Wilkins Co.

O'Flaherty, E. J., et al. A Physiologically Based Model for the Ingestion of Chromium (III) and Chromium (IV) by Humans. Toxicological Sciences, vol. 60, pp. 96-213, 2001.

Toxicological Review of Trivalent Chromium. (CAS No. 16065-83-1) United States Environmental Protection Agency. Aug. 1998. Washington, D.C., 51 pgs.

Donaldson, David L., et al. Chromium (III) Metabolism by the Kidney. Annals of Clinical and Laboratory Science, vol. 11, No. 5. 1981. Institute for Clinical Science, Inc. 9 pgs.

Schroeder, Henry A., et al. Chromium, Cadmium and Lead in Rats: Effects on Life Span, Tumors and Tissue Levels. Journal of Nutrition, vol. 86. 1965. 16 pages.

Chromium—FDA prescribing information, side effects and uses. Drugs.com. Retrieved from URL: http://www.drugs.com/pro/chromium.html. Aug. 31, 2015.

Cupo, Doreen, et al. Binding of Chromium to Chromatin and DNA from Liver and Kidney of Rats Treated with Sodium Dichromate and Chromium (III) Chcloride in Vivo. Cancer Research, vol. 45, Mar. 1985, pp. 1146-1151.

Nethercott, J., et al. A study of chromium induced allergic contact dermatitis with 54 volunteers: implications for environmental risk assessment. Occupational and Environmental Medicine. 1994. vol. 51, pp. 371-380.

ICH guideline Q3C (R5) on impurities: guideline for residual solvents. Step 5. European Medicines Agency. Aug. 2011. 27 pages.

Package insert. Cupric Sulfate Injection USP, Rx Only, Sterile, Pyrogen Free, Trace Element Additive for IV Use After Dilution (Copper 0.4 mg/mL). Rev. Jan. 2009. American Regent, Inc. Shirley, New York 11967.

Boone, C.; Gervais, J. A.; Luukinen, B.; Buhl, K.; Stone, D. 2012, Copper Sulfate Technical Fact Sheet; National Pesticide Information Center, Oregon State University Extension Services. http://npic.orst.edu/factsheets/cuso4tech.pdf.

Harris, Z. L., et al. Aceruloplasmineria: an inherited neurodegenerative disease with impairment of iron hemeostasis. American Journal of Clinical Nutrition. 1998. vol. 67 (Supp): 972S-977S. Downloaded from ajcn.nutrition.org on Sep. 9, 2015.

Uauy, R., et al. Essentiality of copper in humans. American Journal of Clinical Nutrition. 1998. vol. 67 (Suppl): 958S-959S. American Society for Clinical Nutrition.

Lonnerdal, B. Intestinal regulation of copper homeostasis: a developmental perspective. American Journal of Clinical Nutrition. 2008. vol. 88 (Suppl): 846S-850S. American Society for Clinical Nutrition.

Wapnir, R. Copper absorption and bioavailability. American Journal of Clinical Nutrition. 1998. vol. 67 (Suppl): 1054S-1060S. American Society for Clinical Nutrition.

Mortazavi, F., et al. Acute Renal Failure due to Copper Sulfate Poisoning; a Case Report. Iran Journal of Pediatrics. Mar. 2009; vol. 19. No. 1, pp. 75-78.

Gamakaranage et al. Complications and management of acute copper sulphate poisoning; a case discussion. Journal of Occupational Medicine and Toxicology 2011, 6:34 http://www.occup-med.com/content/6/1/34. Jun. 2020.

Ashish, B, et al. Copper Toxicity: A Comprehensive Study. Research Journal of Recent Sciences. vol. 2 (ISC-2012), 58-67 (2013). International Science Congress Association.

Cupric Sulfate. Right to Know Hazardous Substance Fact Sheet, New Jersey Department of Health. Jan. 1999; Rev. Oct. 2008.

(56) References Cited

OTHER PUBLICATIONS

Fluoride in Drinking Water. Background document for development of WHO Guidelines for Drinking Water Quality. 2004. World Health Organization.
Fluoride in Drinking Water: A Scientific Review of EPA's Standards. National Research Council 2006. Washington, DC: The National Academies Press. https://doi.org/10.17226/11571. Available at http://nap.edu/11571.
Biological Aspects of Fluorine. Rev. Oct. 17, 2019. Retrieved from "https://en.wikipedia.org/w/index.php?title=Biological_aspects_of_fluorine&oldid=921702858".
Kanduti, D., et al. Fluoride: A Review of Use and Effects on Health. Mater Sociomed. Apr. 2016; 28(2): 133-137.
Impurities: Guideline for Residual Solvents Q3C(R6). ICH Harmonised Guideline. Current Step 4 version dated Oct. 20, 2016. International Council for Harmonisation of Technical Requirements for Pharmaceuticals for Human Use. 40 pages.
NTP Technical Report on the Toxicology and Carcinogenesis Studies of Sodium Fluoride (CAS No. 7681-49-4) in F344/N Rats and B6C3F Mice. (Drinking Water Studies). Dec. 1990. National Toxicology Program, P.O. Box 12233, Research Triangle Park, NC 27709. U.S. Department of Health and Human Services Public Health Service. National Institutes of Health.
Alfrey Md, A.C. Aluminum Toxicity. Bulletin of NY Academy of Medicine. vol. 60, No. 2, Mar. 1984.
Gorsky, J., et al. Metabolic Balance of Aluminum Studied in Six Men. Clin Chem vol. 25, No. 10; 1739-1743. 1979.
Bernando, Jose F. Aluminum Toxicity. Medscape. Apr. 15, 2015. Retrieved from webpage URL: http://emedicine.medscape.com/article/165315-overview on May 5, 2017.
Eid, R., et al. Iron mediated toxicity and programmed cell death: A review and a re-examination of existing paradigms. Biochimica et Biophysica Acta 1864 (2017) 399-430.
Dainty, Jack R., et al. Estimation of Dietary Iron Bioavailability from Food Iron Intake and Iron Status. PLOS One. vol. 9, No. 10. Oct. 30, 2014.
Coates Md, T.D. Physiology and Pathophysiology of Iron Hemoglobin-Associated Diseases. Free Radic Biol Med. Jul. 2014. vol. 72; 23-40.
Frazer, D. M., et al. Iron Imports. I. Intestinal iron absorption and its regulation. Am J Physiol Gastrointest Liver Physiol. vol. 289; G631-G635, 2005.
Golberg, L., et al. The Effects of Intensive and Prolonged Administration of Iron Parenterally in Animals. Mar. 1, 1957. Excerpt from Effects of Large Doses of Iron. Benger Laboratories Ltd.; Holmes Chapel, Chesire; and the Dept. of Pathology, Univ. of Manchester.
Cabantchik, Z. Labile iron in cells and body fluids: physiology, pathology, and pharmacology. Frontiers in Pharmacology. vol. 5. Article 45. Mar. 2014.
Finazzi, D., et al. Biology of ferritin in mammals: an update on iron storage, oxidative damage and neurodegeneration. Arch Toxicol (2014) vol. 88; 1787-1802. Published online Aug. 15, 2014.
Richardson, D.R., et al. Mitochondrial iron trafficking and integration of iron metabolism between the mitochondrion and cytosol. PNAS. vol. 107. No. 24. 10775-10782. Jun. 15, 2010.
Arosio, P., et al. The Importance of eukaryotic ferritins in iron handling and cytoprotection. Biochem J. (2015) 472; 1-15.
Donovan, A. et al. The iron exporter ferroportin/Slc40a1 is essential for iron homeostasis. Cell Metabolism. Mar. 2005. vol. 1. Elsevier Inc.
Chen, H., et al. Decreased Hephaestin Activity in the Intestine of Copper-Deficient Mice Causes Systemic Iron Deficiency. Nutrient Physiology, Metabolism and Nutrient-Nutrient Interactions. Feb. 2006. American Society for Nutrition.
Cherukuri, S., et al. Unexpected role of ceruloplasmin in intestinal iron absorption. Cell Metabolism. vol. 2. Nov. 2005. Elsevier Inc.
Chiabrando, D., et al. The mitochondrial heme exporter FLVCR1b mediates erythroid differentiation. The Journal of Clinical Investigation. vol. 122. No. 12. Dec. 2012. pp. 4569-4580.
Ganz, T. Hepcidin, a key regulator of iron metabolism and mediator of anemia of inflammation. Blood. vol. 102, No. 3. Aug. 1, 2003.
Pantopoulos, K, et al. Mechanisms of mammalian iron homeostasis. Biochemistry. vol. 51, No. 29. Jul. 24, 2012. pp. 5705-5724.
Gkouvatsos, K., et al. Regulation of iron transport and the role of transferrin. Biochimica et Biophysica Acta 1820. (2012) 188-202. Elsevier Inc.
Silva, B., et al. An overview of molecular basis of iron metabolism regulation and the associated pathologies. Biochimica et Biophysica Acta 1852. (2015) 1347-1359. Elsevier Inc.
Gozzelino, R., et al. Iron Homeostasis in Health and Disease. Int. J. Mol. Sci. 2016, 17, 130.
Chen, M., et al. Iron Overload and Apoptosis of HL-1 Cardiomyocytes: Effects of Calcium Channel Blockade. PLOS One. vol. 9, No. 11. Nov. 2014.
Weinstein, D., et al. Inappropriate expression of hepcidin is associated with iron refractory anemia: implications for the anemia of chronic disease. Blood. vol. 100, No. 10, Nov. 15, 2002.
Nemeth, E. et al. Hepcidin, a putative mediator of anemia of inflammation, is a type II acute-phase protein. Blood. vol. 101, No. 7, Apr. 1, 2003.
Laftah, A., et al. Effect of Hepcidin on intestinal iron absorption in mice. Blood Journal. Retrieved from Internet URL: http://www.bloodjournal.org/content/103/10/3940.full.print? on Aug. 12, 2015.
Delaby, C., et al. Presence of the iron exporter ferroportin at the plasma membrane of macrophages is enhanced by iron loading and down-regulated by hepcidin. Blood Journal. Retrieved from Internet URL: http://www.bloodjournal.org/content/106/12/3979.full.print? on Aug. 12, 2015.
Boyd, E. et al. The Acute Oral Toxicity of Reduced Iron. Canad. Med. Ass. J. vol. 89. Jul. 27, 1963.
Zhang, Z., et al. Taurine supplementation reduces oxidative stress and protects the liver in an iron overload murine model. Molecular Medicine Reports 10: 2255-2262, May 2014.
Carrier, J., et al. Effect of oral iron supplementation on oxidative stress and colonic inflammation in rats with induced colitis. Allment Pharmacol Ther. Jul. 2, 2001; 15: 1989-1999.
Toyoda, T., et al. A 13-week subchronic toxicity study of acetominophen using an obese rat model. The Journal of Toxicological Sciences. vol. 43. No. 7, 423-433. 2018.
Loreal, O., et al. Iron, hepcidin, and the metal connection. Frontiers in Pharmacology. vol. 5; Article 128. Jun. 2014.
Gamella, E., et al. Iron-Induced Damage in Cardiomyopathy: Oxidative-Dependent and Independent Mechanisms. Oxidative Medicine and Cellular Longevity. vol. 2015; Article ID 230182. Mar. 15, 2015.
Milic, S., et al. The Role of Iron and Iron Overload in Chronic Liver Disease. Medical Science Monitor. 2016; vol. 22; 2144-2151.
Andersen, H., et al. Iron deposits in the chronically inflamed central nervous system and contributes to neurodegeneration. Cell. Mol. Life. Sci. (2014) vol. 71; 1607-1622.
Iron in Drinking Water. Background document for development of WHO Guidelines for Drinking Water Quality. 2003. World Health Organization.
Greenwood, Norman N.; Earnshaw, Alan (1997). Iodine. Chemistry of the Elements (2nd ed.). Butterworth-Heinemann. ISBN 978-0-08-037941-8. Retrieved from "https://en.wikipedia.org/w/index.php?title=Iodine&oldid=937989829" Page last edited on Jan. 28, 2020.
U.S. Dept. of Health and Human Services. Toxicological Profile for Iodine. Apr. 2004. 580 pages.
Trace Elements: Iodine. National Report on Biochemical Indicators of Diet and Nutrition in the U.S. Population 1999-2002.
Leung, A., et al. Consequences of excess iodine. Nat. Rev. Endocrinol. Mar. 2014; vol. 10, No. 3; 136-142.
WHO. Guideline: Fortication of food grade salt with iodine for the prevention and control of Iodine deficiency disorders. World Health Organization; 2014.
ICH Harmonised Guideline. Impurities: Guideline for Residual Solvents Q3C(R6). Current Step 4 version. International Council for Harmonisation of Technical Requirements for Pharmaceuticals in Humans. Oct. 20, 2016.
Manganese Sulfate. FDA Package Insert. Rev. Nov. 2005. American Regent, Inc. Shirley, NY 11967. Retrieved from Internet URL: http://medlibrary.org/lib/rx/meds/manganese-sulfate/ on Sep. 12, 2015.

(56) References Cited

OTHER PUBLICATIONS

Product Specification. Manganese (II) sulfate monohydrate. Sigma-Aldrich. St. Louis, MO 63103. www.sigmaaldrich.com; 1 page. Jun. 2020.
U.S. Dept. of Health and Human Services. Toxicological Profile for Manganese. Sep. 2012. 556 pages.
Manganese. Updated Nov. 1987.
Recommended Dietary Allowances, 10th Edition. Subcomittee on the Tenth Edition of the RDAs Food and Nutrition Board Commission on Life Sciences National Research Council. National Academy Press. Washington, D.C. 1989. 298 pages.
Leach, Jr., R.M., et al. Studies on the Role of Manganese in Bone Formation. I. Effect upon the mucopolysaccharide content of chick bone. Journal of Nutrition, vol. 78. 1962.
Ash, David E. Structure and Function of Arginases. Arginine Metabolism: Enzymology, Nutrition and Clinical Significance. 2004. American Society for Nutritional Sciences.
Keller, J., et al. Mitochondrial Manganese Superoxide Dismutase Prevents Neural Apoptosis and Reduces Ischemic Brain Injury: Suppression of Peroxynitrite Production, Lipid Peroxidation, and Mitochondrial Dysfunction. The Journal of Neuroscience, Jan. 15, 1998, 18(2):687-697.
Brown, Frank F., et al. A Study of the Interaction of Manganese Ions with ATP by P Fourier-Transform Nuclear-Magnetic Resonance. Eur. J. Blochem. vol. 38; 54-58 (1973).
Abreu, Isabel A., et al. Superoxide dismutases—a review of the metal-associated mechanistic variations. Biochimica et Biophysica Acta 1804. (2010) 263-274. Elsevier B.V.
Hurley LS, Keen CL, Baly DL. Manganese deficiency and toxicity: effects on carbohydrate metabolism in the rat. Neurotoxicology. 1984 Spring;5(1):97-104. Abstract.
Lindberg, O. et al. Manganese, a Co-factor of Oxidative Phosphorylation. Nature 173, 1038-1039 (May 29, 1954); doi:10.1038/1731038a0. Wenner-Gren's Institute, Stockholm. Mar. 12.
Kimura M., et al. Tissue manganese levels and liver pyruvate carboxylase activity in magnesium-deficient rats. Biol Trace Elem Res. May 1996;52(2):171-9. Abstract.
Malecki, E.A., et al. Manganese Protects against Heart Mitochondrial Lipid Peroxidation in Rats Fed High Levels of Polunsaturated Fatty Acids. Biochemical and Molecular Roles of Nutrients. 1996 American Institute of Nutrition.
Takeda, A. Manganese action in brain function. Brain Res Brain Res Rev. Jan. 2003;41(1):79-87. Abstract.
Marotte, EJ, et al. Manganese superoxide dismutase expression in endothelial progenitor cells accelerates wound healing in diabetic mice. J Clin Invest. Dec. 2010;120(12):4207-19. doi: 10.1172/JCI36858. Epub Nov. 8, 2010. Abstract.
Muszyńska, A., et al. The mechanism of daunorubicin-induced inhibition of prolidase activity in human skin fibroblasts and its implication to impaired collagen biosynthesis. Exp Toxicol Pathol. May 2000;52(2):149-55. Abstract.
Possible Interactions with: Manganese. Retrieved from Internet URL: https://umm.edu/health/medical/altmed/supplement-interaction/possible-interactions-with-manganese. Jun. 2020.
Akinlove, O., et al. Effects of contraceptives on serum trace elements, calcium and phosphorus levels. West Indian Med J. Jun. 2011;60(3):308-15. Abstract.
Mehta, R., et al. Manganese levels in a jaundiced long-term total parenteral nutrition patient: potentiation of haloperidol toxicity? Case report and literature review. JPEN J Parenter Enteral Nutr. Jul.-Aug. 1990;14(4):428-30. Abstract.
Finley, J.W. Manganese absorption and retention by young women is associated with serum ferritin concentration. Am J Clin Nutr. Jul. 1999;70(1):37-43. Abstract.
Fitsanakis, V.A., et al. Manganese (Mn) and iron (Fe): interdependency of transport and regulation. Neurotox Res. Aug. 2010:18(2):124-31. doi: 10.1007/s12640-009-9130-1. Epub Nov. 18, 2009. Abstract.
Maas, E., et al. Influence of Calcium and Magnesium on Manganese Absorption. Plant Physiol. (1969) vol. 44; 796-800.

Barneveld, A., et al. The influence of calcium and magnesium on manganese transport and utilization in Mice. Biological Trace Element Research. Dec. 1984, vol. 6, Issue 6, pp. 489-505. Abstract.
Hathcock, John N. Manganese. Vitamin and Mineral Safety, 2nd Edition. 2004.
Roth, Jerome A. Homeostatic and toxic mechanisms regulating manganese uptake, retention, and elimination. Biol. Res. vol. 39; 45-57; 2006.
Schwartz, Ruth, et al. Apparent absorption and retention of Ca, Cu, Mg, Mn, and Zn from a diet containing bran. The American Journal of Clinical Nutrition. vol. 43: Mar. 1986, pp. 444-455.
WHO. Manganese in Drinking Water. Background document for development of WHO Guidelines for Drinking Water Quality. World Health Organization. 2011.
Keen, Carl L., et al. The Effect of Age on Manganese Uptake and Retention from Milk and Infant Formulas in Rats. Journal of Nutrition. vol. 116: 395-402. 1986. Downloaded from Internet URL: jn.nutrition.org on Sep. 17, 2015.
Kostial, K., et al. Influence of Age on Metal Metabolism and Toxicity. Environmental Health Perspectives. vol. 25: 81-86. (1978).
Zheng, Wei, et al. Comparative Toxicokinetics of Manganese Chloride and Methylcyclopentadienyl Manganese Tricarbonyl (MMT) in Sprague-Dawley Rats. Toxicological Sciences 54, 295-301 (2000) Copyright © 2000 by the Society of Toxicology.
Garcia-Aranda, Jose A., et al. In Vivo Intestinal Absorption of Manganese in the Rat. Journal of Nutrition. vol. 113:2601-2607. 1983. Downloaded from Internet URL: jn.nutrition.org on Sep. 17, 2015.
Kwakye, Gunnar F., et al. Manganese-Induced Parkinsonism and Parkinson's Disease: Shared and Distinguishable Features. Int. J. Environ. Res. Public Health 2015, 12, 7519-7540; doi: 10.3390/ijerph120707519.
NTP Technical Report on the Toxicology and Carcinogenesis Studies of Manganese (II) Sulfate Monohydrate (Cas No. 10034-96-5) in F344/N Rats and B6C3F Mice (Feed Studies) Dec. 1993. NIH Publication No. 94-3159 U.S. Department of Health and Human Services. Public Health Service National Institutes of Health, 275 pages.
Kalea, A.Z., et al. Dietary manganese affects the concentration, composition and sulfation pattern of heparan sulfate glycosaminoglycans in Sprague-Dawley rat aorta. Biometals. Oct. 2006, vol. 19, Issue 5, pp. 535-546. Abstract.
Tran, T.T., et al. Effects of neonatal dietary manganese exposure on brain dopamine levels and neurocognitive functions. Neurotoxicology [2002, 23(4-5):645-651] Abstract.
Ponnapakkam TP, et al. Assessment of male reproductive system in the CD-1 mice following oral manganese exposure. Reproductive Toxicology (Elmsford, N.Y.) [2003, 17(5):547-551] Abstract.
Dodd, Celia, et al. Manganese Potentiates LPS-Induced Heme-Oxygenase 1 in Microglia but not Dopaminergic Cells: Role in Controlling Microglial Hydrogen Peroxide and Inflammatory Cytokine Output. Published in final edited form as: Neurotoxicology, Dec. 2011 ; 32(6): 683-692. doi: 10.1016/j.neuro.2011.09.002.
ICH guideline Q3C (R5) on impurities: guideline for residual solvents. Step 5. European Medicines Agency, London, UK. Aug. 2011.
Freund Md, H., et al. Chromium Deficiency During Total Parenteral Nutrition. JAMA 241:496-498, 1979. Abstract.
Bagchi, D., et al. Cytotoxicity and oxidative mechanisms of different forms of chromium. Toxicology. Oct. 30, 2002;180 (1):5-22. Abstract.
Derelenko, M.J., et al. Thirteen-Week Subchronic Rat Inhalation Toxicity Study with a Recovery Phase of Trivalent Chromium Compounds, Chromic Oxide, and Basic Chromium Sulfate. Toxicological Sciences 52, 278-288 (1999) Copyright © 1999 by the Society of Toxicology.
Wahlberg, J.E. Percutaneous Absorption of Trivalent and Hexavalent Chromium (51Cr) Through Excised Human and Guinea Pig Skin. Dermatologica 1970;141:288-296. Abstract.
Danielsson, B., et al. Embryotoxicity of chromium: Distribution in pregnant mice and effects on embryonic cells in vitro. Archives of Toxicology Dec. 1982, vol. 51, Issue 3, pp. 233-245. Abstract.

(56) References Cited

OTHER PUBLICATIONS

Eastmond, David A., et al. Trivalent Chromium: Assessing the Genotoxic Risk of an Essential Trace Element and Widely Used Human and Animal Nutritional Supplement. Critical Reviews in Toxicology. vol. 38, Issue 3, 2008. Abstract.
Peled, T., et al. Cellular copper content modulates differentiation and self-renewal in cultures of cord blood-derived CD34+ cells. Br J Haematol. Mar. 2002;116(3):655-61. Abstract.
Lazarchick J. Update on anemia and neutropenia in copper deficiency. Curr Opin Hematol. Jan. 2012;19(1):58-60. doi: 10.1097/MOH. 0b013e32834da9d2. Abstract.
Bastarache, E. Copper Compounds Toxicology. Retrieved from Internet URL: http://digitalfire.com/4sight/hazards/ceramic_hazard_copper_compounds_toxicology_329.html. Jun. 2020.
Gaetke, L.M. et al. Copper toxicity, oxidative stress, and antioxidant nutrients. Toxicology. Jul. 15, 2003;189 (1-2):147-63. Abstract.
Leteller M.E., et al. Possible mechanisms underlying copper-induced damage in biological membranes leading to cellular toxicity. Chem Biol Interact. Jan. 15, 2005;151(2):71-82. Abstract.
Mason, R.W. et al. Copper and Copper Salts. International Programme on Chemical Safety. Poisons Information Monograph (Group Monograph) G002. Oct. 4, 1990. National Toxicology Group, University of Otago Medical School, Dunedin, New Zealand.
Mitra, S., et al. Copper-induced immunotoxicity involves cell cycle arrest and cell death in the spleen and thymus. Toxicology. Mar. 11, 2012;293(1-3):78-88. doi: 10.1016/j.tox.2011.12.013. Epub Jan. 8, 2012. Abstract.
Mitra, S., et al. Copper induced immunotoxicity promote differential apoptotic pathways in spleen and thymus. Toxicology. Apr. 5, 2013;306:74-84. doi: 10.1016/j.tox.2013.01.001. Epub Jan. 11, 2013. Abstract.
Hatch, G.E., et al. Correlation of effects of inhaled versus intratracheally injected males on susceptibility to respiratory infection in mice. Am Rev Respir Dis. Aug. 1981;124(2):167-73. Abstract.
Ekstrand, J. Influence of milk products on fluoride bioavailability in man. European Journal of Clinical Pharmacology May 1979, vol. 16, Issue 3, pp. 211-215. Abstract.
Kahn, H. and K. Stralka. Estimated Daily Average Per Capita Water Ingestion by Child and Adult Age Categories Based on USDA's 1994-96 and 1998 Continuing Survey of Food Intakes by Individuals (Journal Article). Journal of Exposure Science and Environmental Epidemiology . Nature Publishing Group, London, UK, 19:396-404, (2008). Abstract.
WHO. Fluorides. World Health Organization. Geneva 2002. 188 pages. Retrieved from Internet URL: http://www.inchem.org/documents/ehc/ehc/ehc227.htm#3.2.1.3. Jun. 2020.
WHO. Aluminum. Environmental Health Criteria 194. World Health Organization. Geneva 1997. 217 pages. Retrieved from Internet URL: http://www.inchem.org/documents/ehc/ehc/ehc194.htm. Jun. 2020.
Aspenström-Fagerlund, B., et al. Fatty acids increase paracellular absorption of aluminium across Caco-2 cell monolayers. Chem Biol Interact. Oct. 7, 2009;181(2):272-8. doi: 10.1016/j.cbi.2009.06.016. Epub Jul. 2, 2009. Abstract.
Iron Basic Information. Chemical Book. 2017. Retrieved from Internet URL: https://www.chemicalbook.com/ProductChemicalPropertiesCB8280013_EN.htm. Jun. 2020.
Iron. Retrieved from Internet URL: http://www.inchem.org/documents/jecfa/jecmono/v18je18.htm. Jun. 2020.
Iodine. Retrieved from Internet URL: https://www.sigmaaldrich.com/catalog/substance/iodine25381755356211?lang=en&region=US. Jun. 2020.
Iodine. Retrieved from Internet URL: http://www.inchem.org/documents/jecfa/jecmono/v024je11.htm. Jun. 2020.
Package insert. Multitrace—4 Pediatric (Trace elements injection 4, USP) for IV use after dilution. Rx only. Rev. Aug. 2018. American Regent, Inc. Shirley, NY 11967.
Package insert. Multitrace—4 Neo-Natal (Trace elements injection 4, USP) for IV use after dilution. Rx only. Rev. Aug. 2018. American Regent, Inc. Shirley, NY 11967.

Copper. Copied from webpage URL: https://lpi.oregonstate.edu/mic/minerals/copper ; 2001; Updated Dec. 2013; Oregon State University, Linus Pauling Institute, Micronutrient Information Center.
AI Aluminum. Merck Index—1952 by Merck & Co., Inc.
King, PhD., Michael W. Introduction to Menkes Disease. | © 1996-2014 themedicalbiochemistrypage.org, LLC | info @ themedicalbiochemistrypage.org.
WHO. Copper—Environmental Health Criteria 200. International Programme on Chemical Safety. World Health Organization. Geneva 1998.
Copper Sulfate. Extoxnet. Extension Toxicology Network. A Pesticide Information Project of Cooperative Extension Offices of Cornell University, Michigan State University, Oregon State University and University of California at Davis. May 1994.
Salto, H., et al. Liver dysfunction and probable manganese accumulation in the brainstem and basal ganglia. J Neurol Neurosurg Psychiatry 1995 58: 760-761. Downloaded from http://jnnp.bmj.com/ on Sep. 16, 2015—Published by group .bmj.com.
Copper (II) Sulfate CASRN: 7758-98-7. NLM HSDB Database. Hazardous Substances Databank No. 916. Last Revision Date: Nov. 8, 2002.
Abstract. USEPA; Drinking Water Criteria Document for Copper (Final Draft) p.V-10 (1985) EPA-600/X-84-190-1].
Abstract. USEPA; Health Issue Assessment: Copper p. 49 (1987) EPA/600/8-87/001].
Abstract. WHO; Environ Health Criteria 200: Copper p. 122 (1998)].
Abstract. USEPA; Health Issue Assessment: Copper p. 44-9 (1987) EPA/600/8-87/001].
Abstract. Bhunya SP, Pati PC; Cytologia 52 (4): 801-8 (1987)].
US EPA. Manganese. TEACH Chemical Summary. U.S. EPA, Toxicity and Exposure Assessment for Children's Health. Last revised Oct. 29, 2007.
Freund, H., et al. Chromium Deficiency During Total Parenteral Nutrition. JAMA 241:496-498, 1979. Abstract.
Groundwater Information Sheet—Boron (B). State Water Resources Control Board, Division of Water Quality, GAMA Program. Rev. May 2016.
Boron. Excerpt from 3.2 Chemistry of the Element. 2020.
Toxicological Profile for Boron. Agency for Toxic Substances and Disease Registry. U.S. Department of Health and Human Services. Public Health Service. Nov. 2010.
Case Reports of Toxicity Effects. CAS Registry No. 10043-35-3. Boracic Acid, Boric Acid. HSDB database. National Library of Medicine. 2020.
Jansen, J.A., et al. Gastro-intestinal absorption and in vitro release of boric acid from water-emulsifying ointments. Food Chem Toxicol. Jan. 1984; 22 (1): 49-53. Abstract.
NTP Technical Report on the Toxicology and Carcinogenesis Studies of Boric Acid (CAS No. 10043-35-3) in Mice (Feed Studies). National Toxicology Program. U.S. Department of Health and Human Services. Oct. 1987.
ICH guideline Q3C (R5) on impurities: guideline for residual solvents. Step 5. European Medicines Agency. Aug. 2011.
Menendez, Ana M., et al., Iron Contamination in Parenteral Nutrition Mixtures-Full Abstract, Bibloteca.ub.edu.ar, Nov. 13, 2023.
American Regent, Selenious Acid Injection, Apr. 2019: https://accessdata.fda.gov/drugsatfda_docs/label/2019/209379s000lbl.pdf (year:2019).
Third-Party Submission. U.S. Appl. No. 17/365,695. dated Feb. 17, 2022.
Burjonrappa et al., Role of trace elements in parenteral nutrition support of the surgical neonate, 2012, Journal of Pediatric Surgery, vol. 47, pp. 760-771 (year:2012).
Fresenius Kabi Canda Limitd. Addnutriv. Product Monograph. Mar. 31, 2020. 18 pgs.
ASPEN. Appropriate Dosing for Parental Nutrition: ASPEN Recommendations 2019. Jan. 8, 2019. 3 pgs.
Dawson, Mick. Endotoxin Limits for Parenteral Drug Products. BET White Paper. Apr. 2017. vol. 1 No. 2. 7 pgs.
Domellof et al. Guidelines on Pediatric Parenteral Nutrition: Iron and Trace Minerals. Clinical Nutrition 37.6 (2018): 2354-2359.

(56) References Cited

OTHER PUBLICATIONS

Fessler, Theresa. Trace Element Monitoring and Therapy for Adult Patients Receiving Long-term Total Parenteral Nutrition. Practical Gastroenterology. Mar. 2005. 10 pgs.

Jacobsen et al. Chapter 32: Methanol, Ethylene Glycol, and Other Toxic Alcohols in Haddad and Winchester's Clinical Management of Poisoning and Drug Overdose. Jun. 7, 2007.pp. 605-633.

JAMA. Guidelines for Essential Trace Element Preparations for Parenteral Use. JAMA Network. May 11, 1979. pp. 2051-2054.

Nielsen, Forrest. Micronutrients in Parenteral Nutrition: Boron, Silicon, and Fluoride. Gastroenterology 137.5 (2009): S55-S60.

USP Chapter 232. Elemental Impurities-Limits. United States Pharmacopeia. 2016. pp. 1-3.

Olson et al. Quantitative Assessment of Trace-Element Contamination in Parenteral Nutrition Components. Journal of Parenteral and Enteral Nutrition. vol. 43 No. 8. Nov. 2019. pp. 970-976.

Pillai et al. Pharmaceutical Glass Interactions. Journal of Pharmaceutical Sciences and Research. vol. 8.2.2016. pp. 103-111.

Popinska et al. Aluminum Contamination of Parenteral Nutrition Additives, Amino Acid Solutions, and Lipid Emulsions. Nutrition. Sep. 1999. vol 15 No 9. pp. 683-686.

Tsallas, George. Availability and Physicochemical Stability of Zinc and Chromium in Total Parenteral Nutrition Solutions. Bull NY Acad. Med. vol. 60. Mar. 1984. pp. 125-131.

Zemrani et al. Trace Element Provision in Parenteral Nutrition in Children: One Size Does Not Fit All. Nutrients. Nov. 2018. 1819. 17 pgs.

Bohrer et al. Contribution of the Raw Material to the Aluminum Contamination in Parenterals. Journal of Parenteral and Enteral Nutrition 26 No. 6 (2002): 382-388.

JPGN 2005. Iron, Minerals and Trace Elements. Journal of Pediatric Gastroenterol Nutrition, vol. 41, Suppl. 2, Nov. 2005. S39-S46.

Exhibit A '548 Chart in Defendant's Invalidity Contentions in the District Court of New Jersey, *American Regent, Inc.* v. *Somerset Therapeutics, LLC, Somerset Pharma, LLC, Odin Pharmaceuticals, LLC, Apotex Inc., Apotex Corp., and Rk Pharma, Inc.*, Civil Action Nos. 24 CV 1022 (BRM)(CLW); 24 CV 1030; 24 CV 1169; 24 CV 2268 (Consolidated) Aug. 29, 2024. 138 pgs.

Exhibit B '022 Chart in Defendant's Invalidity Contentions in the District Court of New Jersey, *American Regent, Inc.* v. *Somerset Therapeutics, LLC, Somerset Pharma, LLC, Odin Pharmaceuticals, LLC, Apotex Inc., Apotex Corp., and Rk Pharma, Inc.*, Civil Action Nos. 24 CV 1022 (BRM)(CLW); 24 CV 1030; 24 CV 1169; 24 CV 2268 (Consolidated) Aug. 29, 2024. 72 pgs.

Exhibit C '565 D Chart in Defendant's Invalidity Contentions in the District Court of New Jersey, *American Regent, Inc.* v. *Somerset Therapeutics, LLC, Somerset Pharma, LLC, Odin Pharmaceuticals, LLC, Apotex Inc., Apotex Corp., and Rk Pharma, Inc.*, Civil Action Nos. 24 CV 1022 (BRM)(CLW); 24 CV 1030; 24 CV 1169; 24 CV 2268 (Consolidated) Aug. 29, 2024. 69 pgs.

Defendant's Invalidity Contentions in the District Court of New Jersey, *American Regent, Inc.* v. *Somerset Therapeutics, LLC, Somerset Pharma, LLC, Odin Pharmaceuticals, LLC, Apotex Inc., Apotex Corp., and Rk Pharma, Inc.*, Civil Action Nos. 24 CV 1022 (BRM)(CLW); 24 CV 1030; 24 CV 1169; 24 CV 2268 (Consolidated) Aug. 29, 2024. 186 pgs.

Fresenius Kabi. Peditrace® Data Sheet. Fresenius Kabi New Zealand Limited. Mar. 31, 2010. 3 pgs.

American Regent, Inc., Zinc Sulfate—zinc sulfate injection, solution Label, Shirley, New York. American Regent, Inc. Oct. 2020. 2 pgs.

Menendez, A.M., et al., SUN-P014: Iron Contamination in Pediatric and Adult Parenteral Nutrition Mixtures. S57-S58 (2017).

American Regent,Inc.'s Prescribing information for Selenious Acid Injection, for intravenous use, published on or about Apr. 30, 2019 (Selenious Acid PI).†

\* cited by examiner
† cited by third party

TRACE ELEMENT COMPOSITIONS, METHODS OF MAKING AND USE

This application claims priority to U.S. Provisional Application Ser. No. 63/047,708, filed on Jul. 2, 2020, the entire disclosure of which is hereby incorporated by reference in its entirety into the present disclosure.

BACKGROUND

Parenteral nutrition (PN) provides nutrients and fluids to a patient and is typically administered intravenously. It differs from normal oral food ingestion in that the nutrients and fluids are administered by an intravenous infusion. In this way, the entire digestive tract is bypassed. Parenteral nutrition is indicated when ingestion of nourishment administered orally via the digestive tract is not possible, not desired, or too dangerous. Thus, parenteral nutrition is used when there are considerable impediments in digestion and resorption, as well as in the framework of intensive care medicine. Complete parenteral nutrition can supply the same nutrients as normal enteral nourishment which includes carbohydrates, fats, proteins, vitamins, electrolytes, water and also trace elements (e.g., trace metals).

Trace elements together with vitamins are required for specific metabolic functions. Trace elements are present at very low concentrations in the human body and help maintain physical and mental health. As structural and/or functional constituents of numerous metalloproteinases (e.g., copper, zinc), enzymes (e.g., selenium), hormones (e.g., iodine) or vitamins (e.g., cobalt), trace elements are involved in many metabolic processes. A deficiency of trace elements impairs the optimal development of important physiological processes in the body.

Often times, one or more trace elements are added to the parenteral nutrition using specific pharmaceutical manufacturing regulations under strict aseptic conditions. Trace element addition to the parenteral nutrition is an important component in the framework of parenteral nutrition therapy. Trace element addition can also remedy an already existing trace element deficiency to help the patient have an enhanced quality of life. Although trace element addition facilitates many enzymatic processes, long term use may cause accumulation of large quantities resulting in toxicity.

In recent years, recommended daily doses of trace elements (e.g., copper, manganese, and chromium) have been reduced and some instances daily doses of chromium are not typically needed. Sometimes, the daily dosage of trace elements needs to be adjusted for contaminants that may already be present in the parenteral nutrition.

Because multiple trace elements (e.g., zinc, copper, selenium, manganese, and chromium) are currently available in all-in-one formulations at higher daily doses, one or more trace elements are not easily customizable to the patient's specific trace element requirement when it is added to the parenteral nutrition.

Typically, parenteral nutrition once admixed remains stable for a relatively short period of time without the addition of trace elements to the parenteral nutrition. For example, once admixed, KABIVEN® parenteral nutrition remains stable for 48 hours at room temperature or 25° C. This stability is without the addition of trace elements to the parenteral nutrition. If not used immediately, the admixed KABIVEN® parenteral nutrition can be stored for up to 7 days under refrigeration at 2° C. to 8° C. without the addition of trace elements to the parenteral nutrition. After removal from refrigeration, the admixed KABIVEN® parenteral nutrition should be used within 48 hours. If not, it should be discarded. This type of stability is also for other different brands of parenteral nutrition.

Parenteral nutrition is admixed based on the specific metabolic needs of the patient. Admixing parenteral nutrition can be time consuming, expensive, and tedious to prepare under aseptic conditions. Often when trace elements are added to parenteral nutrition and the parenteral nutrition is stored for more than 24 to 48 hours at room temperature, stability problems such as, for example, particulate formation and precipitation may occur. This requires the healthcare provider (e.g., pharmacist, nurse, healthcare facility, caregiver, etc.) to dispose of any unused parenteral nutrition after the 24 to 48-hour time period, which increases cost to the patient and the healthcare provider.

Further, if the patient's parenteral nutrition is put on hold for a short period of time (e.g., 48 hours); the admixed parenteral nutrition containing the added trace elements will also need to be discarded. This can lead to drug supply shortages as now the parenteral nutrition and trace elements have to be discarded and a new prescription of parenteral nutrition containing the trace elements has to be admixed again. Because of the short stability period, parenteral nutrition with added trace elements is prepared close to the time period that it will be administered to the patient on a daily basis, which may require frequent trips to the healthcare facility. This also prevents the parenteral nutrition with added trace elements to be made in many daily doses or in batches.

Thus, there is a need for injectable parenteral nutrition containing one or more trace elements that is stable for a longer period of time, thereby reducing the time and costs associated with frequent admixing. The quality of life of the patient and the caregiver is also improved by avoiding frequent trips to healthcare facilities for the admixing of injectable parenteral nutrition. Further, there is also a need for parenteral nutrition with one or more added trace elements that can be made in many daily doses or in batches because it is stable for a longer period of time. There is also a need for trace element compositions and methods that have lower daily doses of one or more trace elements compared to those in currently available trace element products.

SUMMARY

An injectable parenteral nutrition containing a trace element is provided that is stable for a longer period of time compared to existing parenteral nutrition products that have trace elements added thereto, thereby reducing the time and costs associated with frequent admixing. The quality of life of the patient and the caregiver is also improved by avoiding frequent trips to healthcare facilities for the admixing of injectable parenteral nutrition. An injectable parenteral nutrition containing a trace element is also provided that can be made in daily doses or in batches because it is stable for a longer period of time. There is also provided a trace element composition and method that have lower daily doses of one or more trace elements as compared to currently available trace element products (e.g., Mutitrace-5® concentrate, Addamel™) that can be dosed for adult, pediatric or neonatal patients.

In one embodiment there is an injectable composition comprising water, and at least one of about 800 µg to about 4,000 µg of zinc, about 40 µg to about 400 µg of copper, about 4 µg to about 90 µg of selenium, or about 1 µg to about 80 µg of manganese per 1 mL of the injectable composition.

In another embodiment, there is an injectable composition comprising water, and at least one trace element consisting of about 800 µg to about 4,000 µg of zinc, about 40 µg to about 400 µg of copper, about 4 µg to about 90 µg of selenium, or about 1 µg to about 80 µg of manganese per 1 mL of the injectable composition.

In yet another embodiment, there is a method of making an injectable composition, the method comprising mixing at least one of about 800 µg to about 4,000 µg of zinc, about 40 µg to about 400 µg of copper, about 4 µg to about 90 µg of selenium, or about 1 µg to about 80 µg of manganese with water to form 1 mL of the injectable composition.

In still yet another embodiment, there is a method of maintaining plasma trace elements in a patient in need thereof, the method comprising administering at least an injectable composition to the patient, the injectable composition comprising water, and at least one of about 800 µg to about 4,000 µg of zinc, about 40 µg to about 400 µg of copper, about 4 µg to about 90 µg of selenium, or about 1 µg to about 80 µg of manganese per 1 mL of the injectable composition.

In one exemplary embodiment, there is an injectable trace element composition comprising water, and at least one of about 800 µg to about 4,000 µg of zinc, about 40 µg to about 400 µg of copper, about 4 µg to about 90 µg of selenium, or about 1 µg to about 80 µg of manganese per 1 mL of the injectable composition.

In various embodiments, the injectable compositions described in this application comprise, consist essentially of or consist of water, at least one of zinc in an amount from about 600 µg, 700 µg, or 800 µg to about 4,000 µg, copper in an amount from about 40 µg to about 400 µg, from about 4 µg to about 90 µg of selenium, and from about 1 µg to about 80 µg of manganese per 1 mL of the injectable composition.

Stable trace element injectable compositions or injectable compositions that can be added to a parenteral nutrition are provided. In various aspects, a stable injectable composition comprises water, from about 800 µg to about 4,000 µg of zinc, from about 40 µg to about 400 µg of copper, from about 4 µg to about 90 µg of selenium, and from about 1 µg to about 80 µg of manganese per 1 mL of the injectable. In some aspects, the stable trace element injectable composition consists essentially of or consists of water, from about 900 µg to about 4,000 µg of zinc, from about 40 µg to about 400 µg of copper, from about 4 µg to about 90 µg of selenium, and from about 1 µg to about 80 µg of manganese per 1 mL of the injectable.

In some embodiments, methods of making and using the stable injectable compositions of this application are provided. In one aspect, the method of making a trace element injectable composition includes mixing from about 800 µg to about 4,000 µg of zinc, from about 40 µg to about 400 µg of copper, about 4 µg to about 90 µg of selenium, and about 1 µg to about 80 µg of manganese with water to form 1 mL of the injectable composition.

In some embodiments, there is a method of maintaining plasma trace elements in a patient in need thereof, the method including administering at least an injectable composition to the patient, the injectable composition comprising water, from about 800 µg to about 4,000 µg of zinc, from about 40 µg to about 400 µg of copper, from about 4 µg to about 90 µg of selenium, and from about 1 µg to about 80 µg of manganese per 1 mL of the injectable composition.

In various aspects, stable parenteral nutrition is provided comprising at least one of an amino acid, a dextrose, a lipid, water, an electrolyte, or a mixture thereof and at least one trace element which is stable for about at least 3 days to about 14 days. In various embodiments, the at least one trace element of the stable parenteral nutrition includes zinc, copper, selenium, and manganese or a mixture thereof.

In many embodiments, parenteral nutrition comprises, consists essentially of, or consists of an amino acid, a dextrose, a lipid, an electrolyte, or a mixture thereof and at least one trace element composition per from about 250 mL to about 4000 mL of parenteral nutrition. The stable trace element injectable composition that can be added to a parenteral nutrition comprises, consists essentially of or consists of water, from about 800 µg to about 4,000 µg of zinc, from about 40 µg to about 400 µg of copper, from about 4 µg to about 90 µg of selenium, and from about 1 µg to about 80 µg of manganese per 1 mL of the injectable. In some embodiments, the trace element injectable composition that can be added to parenteral nutrition contains water for injection and trace elements comprising, consisting essentially of or consisting of from about 2000 µg to about 4,000 µg of zinc, from about 200 µg to about 400 µg of copper, from about 30 µg to about 90 µg of selenium and from about 20 µg to about 80 µg of manganese per 1 mL of the injectable composition.

In some embodiments, the trace element injectable composition comprises, consists essentially of, or consists of 3,000 µg of zinc, 300 µg of copper, 60 µg of selenium, and 55 µg of manganese per 1 mL of the injectable composition. These trace element compositions are useful additives to parenteral nutrition for adult or pediatric patients.

In yet other embodiments, the stable trace element composition that can be added to parenteral nutrition comprises, consists essentially of or consists of 1000 µg of zinc, 60 µg of copper, 6 µg of selenium and 3 µg of manganese per 1 mL of the injectable composition. These trace element compositions are useful additives to parenteral nutrition for neonate patients.

In various embodiments, the injectable compositions including trace elements can be added to parenteral nutrition available in the marketplace, for example KABIVEN® and CLINIMIX®. As a result, this application provides parenteral nutrition comprising at least one of an amino acid, a dextrose, a lipid, an electrolyte or a mixture thereof and at least one of zinc, copper, selenium, and manganese, which is stable for about at least 3 days to about 14 days.

In some embodiments, there is a method of making a parenteral nutrition containing trace elements, the method comprising adding trace elements to the parenteral nutrition, the trace elements comprising about 800 µg to about 4,000 µg of zinc, about 40 µg to about 400 µg of copper, about 4 µg to about 90 µg of selenium, and about 1 µg to about 80 µg of manganese per 250 mL to about 4000 mL of the parenteral nutrition, the parenteral nutrition comprising at least one of amino acid, a dextrose, a lipid, an electrolyte, or a mixture thereof.

In some aspects, there is a method of providing a source of calories, protein, electrolytes, water or essential fatty acids for adult, pediatric or neonate patients requiring parenteral nutrition, the method comprising administering to a patient in need thereof an injectable parenteral nutrition formulation comprising at least one of an amino acid, a dextrose, a lipid, an electrolyte, or a mixture thereof, the parenteral nutrition comprising about 800 µg to about 4,000 µg of zinc, about 40 µg to about 400 µg of copper, about 4 µg to about 90 µg of selenium, and about 1 µg to about 80 µg of manganese per 250 mL to 4000 mL of the parenteral nutrition.

In some embodiments, there is a method of maintaining plasma trace elements in a patient in need thereof, the method comprising administering a parenteral nutrition to the patient, the parenteral nutrition comprising at least one of an amino acid, a dextrose, a lipid, an electrolyte or a mixture thereof and at least one of zinc, copper, selenium, and manganese, which is stable for about at least 3 days to about 14 days to prevent depletion of endogenous stores of the at least one of zinc, copper, selenium, and manganese and subsequent depletion symptoms.

A method of maintaining, supplementing or increasing one or more trace elements to a patient in need thereof, the method comprising administering to the patient about 800 µg to about 4,000 µg of zinc, about 40 µg to about 400 µg of copper, about 4 µg to about 90 µg of selenium, or about 1 µg to about 80 µg of manganese per about 250 mL to 4000 mL of aqueous fluid, the aqueous fluid comprising an amino acid, a dextrose, a lipid, an electrolyte or a mixture thereof.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

DETAILED DESCRIPTION

Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Scientific and technical terms used herein have meanings commonly used in the art unless otherwise specified. The definitions provided herein are to facilitate understanding of certain terms used frequently herein and are not meant to limit the scope of the present disclosure.

It is noted that, as used in this specification and the appended claims, the singular forms "a," "an," and "the," include plural referents unless expressly and unequivocally limited to one referent. Thus, for example, reference to "a trace element" includes one, two, three or more trace elements.

As used in this specification and the appended claims, the term "or" is generally employed in its sense including "and/of" unless the content clearly dictates otherwise.

Patents, patent applications, published applications and publications, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

The term "composition(s)" refers to an aggregate material formed from two or more substances, ingredients, or constituents; the way in which a whole or mixture is made up. When referring to pharmaceutical drug products, a composition is often called "formulation(s)".

The term "impurity" refers to a constituent, component or ingredient which impairs the purity of a pharmaceutical active ingredient or pharmaceutical composition.

The term "injectable" or "injectable composition," as used herein, means a composition that can be injected into a larger volume container and infused intravenously via peripheral veins found in upper extremities (hands and arms) or central veins, which is a large vein in the central circulation system. Catheters are used to reach either a peripheral or central vein. For example, central venous catheters can be inserted percutaneously or surgically through the jugular, subclavian, or femoral veins, or via the chest or upper arm peripheral veins.

The trace elements composition can be administered parenterally including intravenously or the like into the patient (e.g., mammal). The term "mammal" refers to organisms from the taxonomy class "mammalian," including but not limited to humans, other primates such as monkeys, chimpanzees, apes, orangutans and monkeys, rats, mice, rabbits, cats, dogs, pigs, cows, horses, etc.

The term "reference listed drug" refers to an approved drug product to which generic versions are compared to show that they are bioequivalent.

The term "stability" refers to capability of a pharmaceutical active ingredient or pharmaceutical composition to remain within a specific criteria or specification(s).

The term "stable", as used herein, means remaining in a state or condition that is suitable for administration to a patient and without undergoing a substantial change in the potency of the active agent in the formulation over the specified time period. In some embodiments, the injectable parenteral nutrition composition containing trace elements of the current application is considered stable if the parenteral nutrition composition containing trace elements can maintain its strength at the level specified on the label for the maximum anticipated shelf-life (e.g., the time period from the date of manufacture until administration to the animal, for example, a human patient) under environmental conditions likely to be encountered in actual use. Typically, stability can be determined following the FDA guidelines, for example, Guidance for Industry: Drug Stability Guidelines (p. 1-48), Dec. 9, 2008.

A substantial change in potency is one which decreases the drug concentration by more than 15%, from the target concentration for the specified period of time. Unless indicated otherwise, a stable composition is one which retains at least 85% of the original amount of the injectable composition in that state (e.g., not precipitated, degraded, or adsorbed to the container) for a period of at least 72 hours.

The carriers and excipients and other components of the pharmaceutical compositions must be "pharmaceutically acceptable" in the sense of being compatible with the other ingredients of the formulation and not deleterious to the recipient thereof. Thus, the term "pharmaceutically acceptable salt" references salt forms of the active compounds which are prepared with counter ions which are non-toxic under the conditions of use and are compatible with a stable formulation. For compounds which contain relatively acidic functionalities, base addition salts can be obtained by contacting the neutral form of such compounds with a sufficient amount of the desired base, either neat or in a suitable inert solvent.

The term "pharmaceutically acceptable carrier or excipient" means a carrier or excipient that is useful in preparing a pharmaceutical composition that has an acceptable side-effect profile and serves to provide a medium for the storage or administration of the active component(s) under the conditions of administration for which the composition is formulated or used. The carrier or excipient is compatible with the other ingredients of the formulation and not deleterious to the recipient thereof. A "pharmaceutically acceptable carrier or excipient" as used in the specification and claims includes both one and more than one such carrier or excipient. Pharmaceutically acceptable carriers are determined in part by the particular composition being administered, as well as by the particular method used to administer the composition. For the injectable compositions of this disclosure, water is a pharmaceutically acceptable carrier. There are a wide variety of suitable formulations of pharmaceutical compositions of the present disclosure (see, e.g., Remington's Pharmaceutical Sciences, 20th ed., 2018, supra).

The term "tonicity adjusting agents" refers to agents used to modify the osmolality of a formulation to bring it closer to the osmotic pressure of body fluids such as blood or plasma. Provided that the compositions are physiologically compatible, the compositions do not require any particular osmolality. Thus, the compositions can be hypotonic, isotonic, or hypertonic. Typically, the pharmaceutical compositions have an osmolality between about 250 to 350 mOsm/kg. The tonicity of the pharmaceutical compositions can be adjusted by adjusting the concentration of any one or more of a tonicity agent, a co-solvent, complexing agent, buffering agent, or excipient. Suitable tonicity adjusting agents include, but are not limited to, anhydrous and hydrous forms of dextrose, for example, dextrose 5%, dextrose 10%, dextrose 20%, dextrose 25%, or dextrose 50% in water or a combination thereof.

The pH of the injectable composition can be adjusted to the recited pH range or target pH by the addition of an acid or acidic salt or base or basic salt, as appropriate. For instance, the pH may be adjusted with a base such as an alkali metal hydroxide such as NaOH, KOH, or LiOH, or an alkaline earth metal hydroxide, such as $Mg(OH)_2$ or $Ca(OH)_2$, or a carbonate. Acids useful for adjusting the pH include, without limitation, hydrochloric acid, or sulfuric acid, for example.

The term "pharmaceutical composition" is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients described herein.

The term "single-use container" refers to a sealed pharmaceutically prepared container holding a drug product in a sterile environment that is intended to be used in a single operation of transferring the entire contents or substantially entire contents. It should be recognized that the single-use container is generally preservative-free and that if multiple transfers are attempted, they should be completed in a short duration, i.e., less than about 8-10 hours from the first breach of the sterile environment. In some aspects the single-use container may be used to administer all of its contents to one subject in need thereof. In some aspects the single-use container may be used to administer its contents to more than one subject in need thereof.

As used herein, the term "mixing" refers to admixing, contacting, blending, stirring, or allowing to admix, mix, blend, stir and the like.

The term "dissolved oxygen" refers to oxygen that is found in the aqueous carrier of the compositions. Distinguished from dissolved oxygen is the headspace oxygen. As used herein, the term "headspace oxygen" refers to the oxygen that is found in the headspace volume of the sealed container comprising the composition.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

The headings below are not meant to limit the disclosure in any way; embodiments under anyone heading may be used in conjunction with embodiments under any other heading.

Trace Elements Injectable Compositions

This application relates to the development of injectable compositions comprising at least one of zinc, copper, manganese, and selenium. The injectable compositions of this application include lower daily amounts of at least one of zinc, copper, manganese, chromium, or selenium per 1 mL of the composition than currently available products.

Trace elements, such as zinc, copper, manganese, and selenium are important to metabolic functions and for restoring and maintaining normal growth and development in mammals. Zinc is a trace element. Zinc is a constituent of numerous enzymes including carbonic anhydrase, alcohol and lactate dehydrogenases and various peptidases. Zinc has been identified as a cofactor for over 70 different enzymes, including alkaline phosphatase, lactic dehydrogenase and both RNA and DNA polymerase. Zinc facilitates wound healing, helps maintain normal growth rates, normal skin hydration and the senses of taste and smell. Zinc is considered an essential nutrient participating in multiple metalloenzymes involved in most central metabolic pathways, including metabolism of protein, fat, and carbohydrates; DNA binding; gene regulation; transcription of DNA to RNA; synthesis of heme, long-chain fatty acids, and prostaglandins; cholesterol transport; stabilization of cell membrane lipids; sexual maturation and reproduction; and immune function.

Copper is a trace element. Copper is essential as a cofactor for serum ceruloplasmin, an oxidase necessary for proper formation of the iron carrier protein, transferrin. Copper also helps maintain normal rates of red and white blood cell formation. The metabolic functions of copper relate to its presence in tyrosinase, urate oxidase, dopamine-p-hydroxylase, amine oxidases, cytochrome oxidase and cytoplasmic superoxide dismutase, in the latter, in combination with zinc. Copper is incorporated into metalloenzymes that are involved with connective tissue formation; metabolism of iron (ceruloplasmin), cholesterol, and glucose; myelin synthesis; conversion of dopamine to norepinephrine in the brain, serotonin synthesis, melanin pigment formation; and antioxidant participating in the immune system.

Manganese is another trace element. Manganese is believed to have an activating function for many enzymes such as phosphoglucomutase, choline esterase, the oxidative 0-keto-decarboxylases, certain peptidases, and muscle ATPase. Manganese is an activator for enzymes such as polysaccharide polymerase, liver arginase, cholinesterase, and pyruvate carboxylase. Manganese is incorporated into metalloenzymes involved with energy release, fatty acid and cholesterol synthesis, and release of lipids from the liver.

Selenium is also a trace element. Selenium is part of glutathione peroxidase which protects cell components from oxidative damage due to peroxides produced in cellular metabolism. Selenium is incorporated at the active site of glutathione peroxidase, an enzyme that catalyzes the breakdown of hydroperoxides and has metabolic interrelationships with vitamin E, an antioxidant (Vanek et al., A.S.P.E.N. Position Paper, Nutrition in Clinical Practice, Vol. 27, No. 4, pp. 440-491, August 2012).

In various embodiments, the injectable compositions described in this application comprise, consist essentially of or consist of water, at least one of zinc in an amount from about 900 µg to about 4,000 µg, copper in an amount from about 40 µg to about 400 µg, selenium in an amount from about 4 µg to about 90 µg, or manganese in an amount form about 1 µg to about 80 µg per 1 mL of the injectable composition. Therefore, the injectable composition, in some embodiments, can have as the trace element zinc only, copper only, selenium only, manganese only or they can be in the composition in any combination.

In some embodiments, the injectable compositions described in this application comprise water, and at least one of zinc in an amount from about 2000 µg to about 4,000 µg, copper in an amount from about 200 µg to about 400 µg, about 30 µg to about 90 µg of selenium, and about 20 µg to about 80 µg of manganese per 1 mL of the injectable composition. In some other embodiments, zinc is in an amount from about 900 µg, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900 to about 4000 µg. In various embodiments, copper is in an amount from about 40 µg, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390 to about 400 µg. In other embodiments, selenium is in an amount from about 4 µg, 5, 6, 7, 8, 9, 10, 20, 30, 40, 50, 60, 70, 80 to about 90 µg. In yet other embodiments, manganese is in an amount from about 1 µg, 2, 3, 4, 5, 6, 7, 8, 9, 10, 20, 30, 40, 50, 60, 70 to about 80 µg. In various embodiments, the injectable compositions described in this application comprise, consist essentially of or consist of water, zinc in an amount from about 2000 µg to about 4,000 µg, copper in an amount from about 200 µg to about 400 µg, about 30 µg to about 90 µg of selenium, and about 20 µg to about 80 µg of manganese per 1 mL of the injectable composition.

In some embodiments, the injectable composition comprises water, and at least one of 3,000 µg of zinc, 300 µg of copper, 60 µg of selenium, and 55 µg of manganese per 1 mL of the injectable composition. In other embodiments, the injectable composition consists essentially of or consists of water, 3,000 µg of zinc, 300 µg of copper, 60 µg of selenium, and 55 µg of manganese per 1 mL of the injectable composition. These embodiments are useful as additives to parenteral nutrition applicable to adults or pediatric patients.

In other embodiments, the injectable composition comprises water 1000 µg of zinc, 60 µg of copper, 6 µg of selenium and 3 µg of manganese per about 250 mL to 4000 mL of parenteral nutrition. In yet other embodiments, the trace element injectable composition consist essentially of or consists of water, 1000 µg of zinc, 60 µg of copper, 6 µg of selenium and 3 µg of manganese per about 250 mL to 4000 mL of parenteral nutrition. These embodiments are useful as additives to parenteral nutrition applicable to neonate patients.

In various aspects the injectable composition includes only one of the trace elements, for example only zinc or copper, or manganese or selenium. The at least one of the zinc can include from about 0.23 wt. percent to about 1.33 wt. percent. The at least one of copper can be in an amount from about 0.03 wt. percent to about 0.13 wt. percent. The at least one of manganese comprises from about 0.0055 wt. percent to about 0.013 wt. percent. The at least one of selenium comprises about 0.002 wt. percent to about 0.02 wt. percent and the water comprises from about 96 wt. percent to about 99.66 wt. percent of the injectable composition based on a total weight of the injectable composition. In yet other embodiments, at least one of the zinc comprises about 0.3 wt. percent, the copper comprises about 0.03 wt. percent, the manganese comprises about 0.0055 wt. percent, the selenium comprises about 0.006 wt. percent, or the water comprises from about 99.66 wt. percent of the injectable composition based on a total weight of the injectable composition.

In many aspects, the zinc in the injectable composition is elemental zinc, the copper is elemental copper, the selenium is elemental selenium, the manganese is elemental manganese and the water is sterile water for injection. In other instances, the elemental zinc is obtained from zinc sulfate or zinc sulfate heptahydrate, the elemental copper is generated from cupric sulfate or cupric sulfate pentahydrate, the elemental manganese is from manganese sulfate or manganese sulfate monohydrate and the elemental selenium is obtained from selenious acid. The injectable composition described in this application contains, in some aspects, zinc obtained from zinc sulfate heptahydrate, wherein the zinc and is at a dose of from about 2.5 to about 7 mg/day. The copper of the injectable composition can be obtained from cupric sulfate pentahydrate and is at a dose of from about 0.3 to about 1.5 mg/day, the manganese is manganese sulfate monohydrate and is at a dose of about 0.015 to about 0.08 mg/day, and the selenium is obtained from selenious acid and is at a dose of from about 20 to about 60 µg/day. In other aspects, the injectable composition contains zinc from zinc sulfate heptahydrate, wherein the zinc is at a dose of from about 2.5 to about 7 mg/day, the copper is obtained from cupric sulfate pentahydrate and is at a dose of from about 0.5 to about 1.5 mg/day, the manganese is obtained from manganese sulfate monohydrate and is at a dose of from about 0.15 to about 0.8 mg/day, and the selenium is obtained from selenious acid and is at a dose of about 20 to about 40 µg/day.

In various aspects, the trace elements of the compositions of this application comprise, consist essentially of or consist of zinc sulfate or zinc sulfate heptahydrate in an amount of from about 13.1 mg (13000 µg) to about 13.3 mg, cupric sulfate or cupric sulfate pentahydrate in an amount of about 1.1 mg to about 1.2 mg, manganese sulfate or manganese sulfate monohydrate in an amount of about 0.16 mg to about 0.18 mg and selenious acid in an amount of about 95 µg to about 99 µg per 1 mL of the injectable composition. In other aspects, in the injectable compositions, the trace elements comprise, consist essentially of or consist of zinc sulfate or zinc sulfate heptahydrate in an amount of from about 13.1 mg (13000 µg) to about 13.3 mg, cupric sulfate or cupric sulfate pentahydrate in an amount of from about 1.1 mg to about 1.2 mg, manganese sulfate or manganese sulfate monohydrate in an amount of from about 0.016 mg to about 0.018 mg and selenious acid in an amount of from about 95 µg to about 99 µg per 1 mL of the injectable composition. In yet other aspects, the zinc sulfate or zinc sulfate heptahydrate is in an amount of about 13.2 mg, the cupric sulfate or the cupric sulfate pentahydrate is in an amount of about 1.179 mg, the manganese sulfate or manganese sulfate monohydrate is in an amount of about 0.169 mg and the selenious acid is in an amount of about 98 µg per 1 mL of the injectable composition.

Zinc Sulfate heptahydrate is available from Avantor Performance Materials, LLC in Phillipsburg, NJ. Cupric sulfate pentahydrate USP can be obtained from Merck KGaA in Germany. Manganese sulfate monohydrate is available from Merck KGa in Germany. Selenious acid is available from Sigma Aldrich.

The trace elements composition can be added to one of an amino acid, a dextrose, a lipid, an electrolyte or a mixture thereof and administered to the patient parenterally (e.g., intravenously). Typically, the trace elements composition can be administered by intravenous infusion. For example, the trace elements composition can be added to parenteral nutrition and administered intravenously where about 100 mL to 4000 mL can be administered via IV infusion over, for example, about 4 hours to 24 hours, or about 8 hours to 48 hours to the patient.

One embodiment of the trace elements injectable composition of this application useful for adult or pediatric patients is summarized in Table 1.

TABLE 1

Injectable Composition

| Ingredient (Name and Quality Standard) | Function | Quantity per mL | % w/v | Elemental Equivalent |
|---|---|---|---|---|
| Zinc Sulfate•7H$_2$O, USP | Active | 13.20 mg | 1.320% | 3 mg Zn/mL |
| Cupric Sulfate•5H$_2$O, USP | Active | 1.18 mg | 0.118% | 0.3 mg Cu/mL |
| Manganese Sulfate•H$_2$O, USP | Active | 169 mcg | 0.017% | 55 µg Mn/mL |
| Selenious Acid, USP | Active | 98 mcg | 0.010% | 60 µg Se/mL |
| Sulfuric Acid, NF | pH adjustment | N/A | N/A | N/A |
| Water for Injection, USP | Solvent | q.s. to 1 mL | 98.535% | N/A |

N/A refers to not applicable; USP refers to United States Pharmacopeia; NF refers to National Formulary.

Elemental Impurities of Trace Elements Injectable Composition

The trace elements injectable composition, USP is a compendial drug product. Consequently, the characteristics of the injectable composition are based on the drug product release specifications established by the compendial monograph for the product, FDA guidance, and the International Council for Harmonization of Technical Requirements for Pharmaceuticals for Human Use (ICH) recommendations. The drug product release specifications, which include all critical drug product attributes, are illustrated in Table 2.

TABLE 2

Specifications and Properties of Trace Elements Injectable Composition

| Properties | Target | Justification |
|---|---|---|
| Description | Clear, colorless, to slightly blue solution and is essentially free from visible particulates. | Based on accumulated data and as per current USP <1>. |
| Identification | A. Zinc - The Assay preparation, prepared as directed in the Assay, exhibits an emission maximum at 472.215 nm when tested as directed for Procedure in the respective Assay. B. Copper - The Assay preparation, prepared as directed in the Assay, exhibits an emission maximum at 224.700 nm when tested as directed for Procedure in the respective Assay. C. Selenium - The Assay preparation, | In accordance with proposed USP monograph for Trace Elements Injectable Composition and ICH requirements for identification tests. |

TABLE 2-continued

Specifications and Properties of Trace Elements Injectable Composition

| Properties | Target | Justification |
|---|---|---|
| | prepared as directed in the Assay, exhibits an emission maximum at 196.026 nm when tested as directed for Procedure in the respective Assay. D. Manganese - The Assay preparation, prepared as directed in the Assay, exhibits an emission maximum at 279.827 nm when tested as directed for Procedure in the respective Assay. | |
| pH | Between 1.5 and 3.5 | In accordance with proposed USP monograph for Trace Elements Injectable Composition and ICH requirements for identification tests. |
| Residual Solvents | Meets Requirements under Option 2. | As per USP <467> and ICH Q3C. |
| Assay | Zinc: 90.0%-110.0% Label Claim (L.C. = 3 mg/mL of Zinc) Copper: 90.0%-110.0% Label Claim (L.C. = 0.3 mg/mL of Coper) Selenium: 90.0%-110.0% Label Claim (L.C. = 60 μg/mL of Selenium) Manganese: 90.0%-110.0% Label Claim (L.C. = 55 μg/mL of Manganese) | |
| Volume of Solution | 1 mL fill: the volume is not less than the labeled volume of 1 mL. | As per USP <1151>. |
| Aluminum | Not more than 6,000 μg/L | As per 21 CFR 201.323, USP <7>, and FDA recommendation for the limit of not more than 0.6 μg/kg/day. |
| Elemental Impurities | Meets requirements Cadmium (Cd): Not more than 0.4 μg/mL Lead (Pb): Not more than 0.5 μg/mL Arsenic (As): Not more than 1.5 μg/mL Mercury (Hg): Not more than 0.4 μg/mL Chromium (Cr): Not more than 1.0 μg/mL Iron (Fe): Not more than 10 μg/mL Boron (B): Not more than 50 μg/mL Calcium (Ca): Not more than 50 μg/mL Magnesium (Mg): Not more than 50 μg/mL Silicon (Si): Not more than 100 μg/mL | As per ICH Q3D and USP <232> for the intended dose volume of 1 mL/day for Adult and Pediatric patients. |
| Particulate Matter | NMT 6,000 particles ≥10 μm per vial NMT 600 particles ≥25 μm per vial If retested by the Microscopic Method: NMT 3,000 particles ≥10 μm per vial NMT 300 particles ≥25 μm per vial | As per USP <788>. |
| Sterility | If no growth is observed, the article tested meets the requirements of the test for sterility. | As per USP <71>. |
| Bacterial Endotoxins | The Endotoxin limit is not more than 50 EU/mL | As per USP <85> and the maximum daily dose of the drug product. |
| Other Requirements | It meets the requirements under Injections and Implanted Drug Products <1>. | As per USP <1>. |

While these injectable compositions contain little or no impurities, in some aspects, these compositions can include a chromium impurity in an amount not to exceed about 1 pig and, in other aspects, not to exceed 0.5 pig. In other instances, the injectable composition contains from about 0.0001 pig/mL to about 0.25 pig/mL of chromium. In many cases, the injectable composition of this disclosure does not contain any detectable chromium or no chromium at all.

In some embodiments, the chromium can be in the PN containing the trace elements composition or the trace elements composition itself in an amount of not more than about 0.15 μg/mL, 0.14 μg/mL, 0.13 μg/mL, 0.12 μg/mL, 0.11 μg/mL, 0.10 μg/mL, 0.09 μg/mL, 0.08 μg/mL, 0.07 μg/mL, 0.06 μg/mL, 0.05 μg/mL, 0.04 μg/mL, 0.03 μg/mL, 0.02 μg/mL to not more than about 0.01 μg/mL, or lower. Therefore, in this embodiment, it is desirable to have no or little chromium.

In various embodiments, other elemental impurities, for example, lead, arsenic, cadmium, mercury iron, chromium (potential manufacturing process contaminants) and boron, calcium, magnesium, and silicon (potential leachable elemental impurities from the drug product Type I glass vials and West elastomeric formulation 4432/50 grey stopper used as immediate packaging) have been considered.

Dosing recommendations for pediatric patients is based on body weight and ranges from about 0.2 mL to about 0.8 mL per day as shown in Table 3 where MDD refers to maximum daily dose.

TABLE 3

Dosing Requirements in mL/kg Body Weight for Trace Element Compositions

| Patient Group | Body Weight | MDD (mL) |
|---|---|---|
| Adult | ≥50 kg | 1 mL |
| Pediatric | 40 kg to 49 kg | 0.8 mL |
| Pediatric | 30 kg to 39 kg | 0.6 mL |
| Pediatric | 20 kg to 29 kg | 0.4 mL |
| Pediatric | 10 kg to 19 kg | 0.2 mL |

In some embodiments, the permitted daily limits (PDL) of the injectable trace elements of the current application include, as little as possible of cadmium, lead, arsenic, mercury, cobalt, vanadium, nickel, thallium, gold, palladium, iridium, osmium, rhodium, ruthenium, silver, platinum, lithium, antimony, barium, molybdenum, tin, chromium, aluminum, boron, calcium, iron, potassium, magnesium, sodium, tungsten, and/or silicon.

In some embodiments, the permitted daily limits (PDL) of the injectable trace elements of the current application are not to exceed about 0.4 µg/day of cadmium, about 0.5 µg/day of lead, about 1.5 µg/day of arsenic, about 0.4 µg/day of mercury, about 1 µg/day of cobalt, about 2 µg/day of vanadium, about 4 µg/day of nickel, about 1.6 µg/day of thallium, about 20 µg/day of gold, about 2 µg/day of palladium, about 2 µg/day of iridium, about 2 µg/day of osmium, about 2 µg/day of rhodium, about 2 µg/day of ruthenium, about 2 µg/day of silver, about 2 µg/day of platinum, about 50 µg/day of lithium, about 18 µg/day of antimony, about 140 µg/day of barium, about 300 µg/day of molybdenum, about 120 µg/day of tin, about 1 µg/day of chromium, about 6 µg/day of aluminum, about 50 µg/day of boron, about 50 µg/day of calcium, about 10 µg/day of iron, about 94,000 µg/day of potassium, about 50 µg/day of magnesium, about 24,000 µg/day of sodium, about 1 µg/day of tungsten, and/or about 100 µg/day of silicon.

Permitted Daily Exposure (PDE) for pediatric patient groups were calculated using the following equation: PDE (µg/day) for Pediatric=PDE per ICH (µg/day)/(50 kg)(10 kg).

Concentration limit for each element is based on PDE, the maximum daily volume, and ICH control threshold, defined as a level that is 30% of the established PDE in the drug product was calculated using the following formulas:

$$\text{Concentration Limit } (\mu g/mL) = PDE\ (\mu g/Day)/\text{Maximum Daily Volume (mL)}$$

$$\text{Control Threshold } (\mu g/mL) = \text{Concentration Limit } (\mu g/mL)/100\% \cdot 30\%$$

A summary of PDEs, concentration limits, and 30% control thresholds for evaluated elements are provided in Table 4.

TABLE 4

Elemental Impurities Concentration Limits for Trace elements injectable composition, USP for Pediatric Patient Population

| Element | Class | PDE Limit (µg/day) | PDE Limit Pediatric (µg/day) | Concentration Limit (µg/mL) | American Regent Specification (µg/mL) | Control Threshold (µg/mL) |
|---|---|---|---|---|---|---|
| Cd (Cadmium) | 1 | 2 | 0.4 | 0.4 | 0.4 | 0.12 |
| Pb (Lead) | 1 | 5 | 1 | 1 | 0.5 | 0.3 |
| As (Arsenic) | 1 | 15 | 3 | 3 | 1.5 | 0.45 |
| Hg (Mercury) | 1 | 3 | 0.6 | 0.6 | 0.4 | 0.1 |
| Co (Cobalt) | 2A | 5 | 1 | 1 | 1 | 0.3 |
| V (Vanadium) | 2A | 10 | 2 | 2 | 2 | 0.6 |
| Ni (Nickel) | 2A | 20 | 4 | 4 | 4 | 1.2 |
| Tl (Thallium) | 2B | 8 | 1.6 | 1.6 | 1.6 | 0.5 |
| Au (Gold) | 2B | 100 | 20 | 20 | 20 | 6 |
| Pd (Palladium) | 2B | 10 | 2 | 2 | 2 | 0.6 |
| Ir (Iridium) | 2B | 10 | 2 | 2 | 2 | 0.6 |
| Os (Osmium) | 2B | 10 | 2 | 2 | 2 | 0.6 |
| Rh (Rhodium) | 2B | 10 | 2 | 2 | 2 | 0.6 |
| Ru (Ruthenium) | 2B | 10 | 2 | 2 | 2 | 0.6 |
| Ag (Silver) | 2B | 10 | 2 | 2 | 2 | 0.6 |
| Pt (Platinum) | 2B | 10 | 2 | 2 | 2 | 0.6 |
| Li (Lithium) | 3 | 250 | 50 | 50 | 50 | 15 |
| Sb (Antimony) | 3 | 90 | 18 | 18 | 18 | 5.4 |
| Ba (Barium) | 3 | 700 | 140 | 140 | 140 | 42 |
| Mo (Molybdenum) | 3 | 1,500 | 300 | 300 | 300 | 90 |
| Sn (Tin) | 3 | 600 | 120 | 120 | 120 | 36 |
| Cr (Chromium) | 3 | 1,100 | 220 | 1.0 | 1.0 | 0.3 |
| Al (Aluminum) | other | 6 | 6 | 6 | 6.0 | 1.88 |
| B (Boron) | other | 3,400 | 680 | 50 | 50 | 15 |
| Ca (Calcium) | other | 82,500 | 16,500 | 50 | 50 | 15 |
| Fe (Iron) | other | 1,300 | 260 | 10 | 10 | 3 |
| K (Potassium) | other | 470,000 | 94,000 | 94,000 | 94,000 | 28,200 |
| Mg (Magnesium) | other | 35,000 | 7,000 | 50 | 50 | 15 |
| Na (Sodium) | other | 120,000 | 24,000 | 24,000 | 24,000 | 7,200 |
| W (Tungsten) | other | N/A | N/A | N/A | 1 | 1 |
| Si (Silicon) | In-house | 19,200 | 3,840 | 100 | 100 | 30 |

In various embodiments, the trace elements injectable compositions of this application do not contain any detectable chromium or any chromium at all. However, in other embodiments, for example, in a selenious acid injection or zinc sulfate injection or even in an injectable composition containing zinc, copper, selenium and manganese, the chromium content will not exceed about 0.3 μg/mL.

In various embodiments, the injectable compositions of this application also include (i) iodine from about 0.0001 to about 0.2 mcg/kg/day, fluoride from about 0.0001 to about 2.7 mcg/kg/day, aluminum from about 0.0001 to about 0.6 mcg/kg/day or a mixture thereof; or (ii) iodine from about 0 to about 0.2 mcg/kg/day, fluoride from about 0 to about 2.7 mcg/kg/day, aluminum from about 0 to about 0.6 mcg/kg/day or a mixture thereof. In other embodiments, the injectable composition of this application also includes (i) iron from about 0.0001 to about 10 μg/mL, silicon from about 0.0001 to about 100 μg/mL, magnesium from about 0.0001 to about 50 μg/mL, calcium from about 0.0001 to about 50 μg/mL, boron from about 0.0001 to about 50 μg/mL or a mixture thereof; or (ii) iron from about 0 to about 10 μg/mL, silicon from about 0 to about 100 μg/mL, magnesium from about 0 to about 50 μg/mL, calcium from about 0 to about 50 μg/mL, boron from about 0 to about 50 μg/mL or a mixture thereof.

pH Considerations

In various aspects, the injectable composition described in this application has a pH of from about 1.0 to about 5. In other aspects, the injectable composition has a pH from about 1.5 to about 3.5 or from about 1.5 to about 4.0. In many aspects, the pH of the trace elements composition described in this application can vary from about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0. In some instances, sodium hydroxide or sulfuric acid can be added to adjust the pH.

In some embodiments, pH limits for multi-element and/or single entity trace elements injections are listed in Table 5 below.

may precipitate. In the case of selenious acid, to maintain the active ingredient in the ionized form, a low pH is recommended.

The compositions of this application can be at least one of a preservative-free composition, a sterile composition, or a ready-to-use injectable aqueous composition designed to be injected or added to a parenteral nutrition. However, in some embodiments, the compositions can comprise a preservative. The preservative can be, in some cases, benzyl alcohol in an amount of 0.9% by weight based on a total weight of the injectable composition.

The injectable composition of trace elements can be dispensed in single dose vial or can be dispensed in multi-dose vials. The trace elements composition of this application is often presented as a 1-mL fill in a 2-mL single dose preservative free vial. In many instances the vial can accommodate from about be 1 mL, 2, 3, 4, 5, 6, 7, 8, 9 to about 10 mL of fluid. In some cases, the vials can be prepared of Pyrex glass or have the inside surface sprayed or coated with silica or can be made of plastic material. This is to minimize the amount of aluminum that may potentially be leaching from a glass vial to an amount not to exceed 0.6 μg/kg of body weight of a patient in need of trace elements treatment or no more than 25 μg/L of intravenous (IV) infusion. In some cases, the amount of aluminum can vary from about 1 μg/mL (1 ppm) to about 6 μg/mL of aluminum. In other cases, there is no aluminum present.

In some embodiments, the injectable compositions comprising water, from about 900 μg to about 4,000 μg of zinc, from about 40 μg to about 400 μg of copper, from about 4 μg to about 90 μg of selenium, and from about 1 μg to about 80 μg of manganese per 1 mL of the injectable composition and can be used as a component of or additive to a parenteral nutrition comprising at least one of an amino acid, a dextrose, a lipid, an electrolyte or a mixture thereof. In other embodiments, the injectable compositions comprise water, from about 2000 μg to about 4,000 μg of zinc, from about 200 μg to about 400 μg of copper, from about 30 μg to about 90 μg of selenium, and from about 20 μg to about 80 μg of manganese per 1 mL of the injectable composition and can

TABLE 5 pH Limits for Multi-Element and Single Entity Trace Elements Injections

| Drug Product | Fill size | Container | USP pH limit | In-process pH limit |
|---|---|---|---|---|
| Trace elements injectable composition, USP (3 mg/mL Zn as zinc sulfate, 0.3 mg/mL Cu as cupric sulfate, 55 μg/mL Mn as manganese sulfate, 60 μg/mL Se as selenious acid) | 1 mL | 2 mL vial | 1.5 to 3.5 | 1.9 to 2.1 |
| Zinc Sulfate Injection, USP 3 mg/mL (3 mg/mL Zn as zinc sulfate) | 10 mL | 10 mL vial | 2.0 to 4.0 | 2.2 to 2.5 |
| Zinc Sulfate Injection, USP 5 mg/mL (5 mg/mL Zn as zinc sulfate) | 5 mL | 5 mL vial | | |
| Selenious Acid Injection, USP | 10 mL | 10 mL vial | 1.8 to 2.4 | 2.0 to 2.2 |

With the exception of selenious acid, the active ingredients in trace elements injectable compositions of this application, are formed from their specific trace elements (zinc, copper, and manganese) by reaction with acids (sulfuric acid or hydrochloric acid) to form their respective mineral salt (e.g., zinc sulfate, cupric sulfate, and manganese sulfate). As weak acids, these salts are more stable in acidic solutions because in neutral and alkaline solutions they form metal hydroxides (e.g., $Zn(OH)_2$; $Cu(OH)_2$; and $Mn(OH)_2$) which be used as a component of or additive to a parenteral nutrition comprising at least one of an amino acid, a dextrose, a lipid, an electrolyte or a mixture thereof.

The parenteral nutrition (PN) can include at least one of an amino acid, dextrose, a lipid, an electrolyte, or a mixture thereof. The at least one of (i) the amino acid comprises lysine hydrochloride, phenylalanine, leucine, valine, threonine, methionine, isoleucine, tryptophan, alanine, arginine, glycine, proline, histidine, glutamic acid, serine, aspartic acid, tyrosine or a mixture thereof; (ii) the dextrose comprises dextrose monohydrate; (iii) the lipid comprises soybean oil, phospholipid, glycerin or a mixture thereof; or (iv) the electrolyte comprises sodium acetate trihydrate, potassium chloride, sodium chloride, potassium acetate, sodium glycerophosphate anhydrous, magnesium sulfate heptahydrate, calcium chloride dihydrate, calcium gluconate or a mixture thereof. The resulting parenteral nutrition (PN) compositions can have a pH in a range from about 3.5 to about 7.9.

The injectable PN compositions described in this disclosure are also nonpyrogenic solutions. Unexpectedly, it has been found that including trace elements in a parenteral nutrition allowed the parenteral nutrition to be stable when stored from about 2° C. to about 8° C. for at least up to about 14 days. In some instances, when stored from about 2° C. to about 8° C. for about 14 days, the parenteral nutrition can maintain a pH from about 5.50 to about 5.90. Moreover, in other instances, when stored from about 2° C. to about 8° C. for about 14 days, the parenteral nutrition comprises at least one of (i) no more than 12 particle per mL that are greater than 10 μm; or (ii) no more than 2 particle per mL that are greater than 25 μm.

In some embodiments, the parenteral nutrition can be in solution form and contains 0.2 mL to 1 mL trace elements injection per liter, can have no or negligible amounts of aluminum, for example, from about 0.2 μg/mL to about 6 μg/mL, which is an amount that should not be exceeded. In other cases, there is no aluminum present, which is therefore absent.

In many embodiments, when stored from about 2° C. to about 8° C. for about 14 days, the parenteral nutrition does not exhibit microbial growth. Microbes that could otherwise grow in the parenteral nutrition composition include *S. aureus, P. aeruginosa, E. coli, C. albicans, A. brasiliensis* or a mixture thereof. As with other compositions described in this application, parenteral nutrition compositions including trace elements are dispensed in a container typically is from about a 50 mL container to about a 4000 mL container. The parenteral nutrition can be in glass, polyvinyl chloride, di(2-ethylhexyl) phthalate, polyethylene, polypropylene, polyvinyl chloride, polycarbonate, polyolefin or a combination thereof that can hold larger volume parenteral nutrition from about a 50 mL container to about a 4000 mL. The parenteral nutrition container can have at least one port for the injection of the trace elements and/or other additives into the parenteral nutrition container.

The trace elements, before being added to the parenteral nutrition, can be in a single use vial or an ampule or in a container which comprises a vial having a stopper acceptable for a parenteral drug product and/or a cap. In many aspects, the trace elements can be placed into a 1 mL single dose vial or in 10 mL multiple dose vial. The vial or ampules can be made of molded glass, glass coated with silica or polypropylene.

Parenteral Nutrition Compositions Containing Trace Elements

Parenteral nutrition refers to solutions for the intravenous administration of nutrients necessary for the maintenance of life. Parenteral nutrition can be prepared not only for adult patients but also for pediatric and/or neonatal patients.

An injectable parenteral nutrition containing trace elements is provided that is stable for a longer period of time, thereby reducing the time and costs associated with frequent admixing. The quality of life of the patient and the caregiver is also improved by avoiding frequent trips to healthcare facilities for the admixing of injectable parenteral nutrition. An injectable parenteral nutrition containing trace elements is also provided that can be made in daily doses or in batches because it is stable for a longer period of time.

For example, because the PN containing one or more trace elements of the current application has been found to be stable under refrigeration for up to 14 days, now the healthcare provider (e.g., pharmacist) can make the daily dose of parenteral nutrition in batches for one or more patients and, for example, a week supply or more can be admixed and dispensed for that particular patient, which eliminates the need and reduces costs as now that pharmacist will not need to be available on a daily basis to make the parenteral nutrition close in time to when it is administered to the patient. Further, less frequent trips back and forth to the healthcare facility are required.

One or more trace elements can be added to the amino acids, dextrose, lipids, and/or electrolytes in the parenteral nutrition. The amino acids, dextrose, lipids, and/or electrolytes in the parenteral nutrition can be from commercially available parenteral nutrition products, such as for example, AminoProtect® (essential and non-essential amino acids, Anazao Health Corp.), Aminosyn® II (amino acid injection with electrolytes in dextrose injection with calcium, Hospira, Inc.), Aminosyn® II/Electrolytes (amino acid injection with electrolytes in dextrose injection with calcium, Hospira Inc.), Aminosyn® M (a crystalline amino acid solution with electrolytes, Hospira Inc.), Aminosyn® (a crystalline amino acid solution with electrolytes, Hospira Inc.), Aminosyn®-HBC (sulfite-free, amino acid injection high branched chain, Hospira Inc.), Aminosyn®-PF (sulfite-free, amino acid injection pediatric formula, Hospira Inc.), Aminosyn®-RF (sulfite free amino acid injection 5.2% renal formula, Hospira Inc.), Aminosyn®/Electrolytes (these are essential and non-essential amino acid injection with electrolytes, Hospira Inc.), BranchAmin® (branched chain amino acid solution of essential amino acids isoleucine, leucine, and valine, Baxter Healthcare Corp.), Clinimix® E/Dextrose (amino acid/dextrose 2.75/10, Baxter Healthcare Corp.), Clinimix® E/Dextrose (amino acid/dextrose 2.75/5, Baxter Healthcare Corp.), Clinimix® E/Dextrose (amino acid/dextrose 4.25/10, Baxter Healthcare Corp.), Clinimix® E/Dextrose (amino acid/dextrose 4.25/25, Baxter Healthcare Corp.), Clinimix® E/Dextrose (amino acid/dextrose 4.25/5, Baxter Healthcare Corp.), Clinimix® E/Dextrose (amino acid/dextrose 5/15, Baxter Healthcare Corp.), Clinimix® E/Dextrose (amino acid/dextrose 5/20, Baxter Healthcare Corp.), Clinimix® E/Dextrose (amino acid/dextrose 5/25, Baxter Healthcare Corp.), Clinimix® N14G30E (amino acid solution with electrolytes and a glucose solution with calcium, Baxter Healthcare Corp.), Clinimix® N9G15E (amino acid solution with electrolytes and a glucose solution with calcium chloride, Baxter Healthcare Corp.), Clinimix® N9G20E (amino acid solution 2.75% with electrolytes in dextrose 10% solution for injection, Baxter Healthcare Corp.), Clinimix®/Dextrose (amino acid/dextrose 2.75/5, Baxter Healthcare Corp.), Clinimix®/Dextrose (amino acid/dextrose 4.25/10, Baxter Healthcare Corp.), Clinimix®/Dextrose (amino acid/dextrose 4.25/20, Baxter Healthcare Corp.), Clinimix®/Dextrose (amino acid/dextrose 4.25/25, Baxter Healthcare Corp.), Clinimix®/Dextrose (amino acid/dextrose 4.25/5, Baxter Healthcare Corp.), Clinimix®/Dextrose (amino acid/dextrose 5/15, Baxter Healthcare Corp.), Clinimix®/Dextrose (amino acid/dextrose 5/20, Baxter Healthcare Corp.), Clinimix®/Dextrose (amino acid/dextrose 5/25, Baxter Healthcare Corp.), Clinisol® SF (sulfite-free amino acid injection, Baxter Healthcare Corp.), Clinolipid® (lipid injectable emulsion, Baxter Healthcare Corp.), Delflex® (peritoneal dialysis solutions (standard and low magnesium/low calcium) of dextrose and electrolytes in water for injection, Fresenius Medical Care North America), Elcys® (cysteine hydrochloride injection, Excela Pharma Science, LLC), FreAmine® HBC (amino acid injection, B. Braun Medical Inc.), FreAmine® III (amino acid injection, B. Braun Medical Inc.), Hyperlyte® CR (multi-electrolyte concentrate, B. Braun Medical Inc.), Hepatamine® (amino acid injection, B. Braun Medical Inc.), Intralipid® (purified soybean oil, purified egg lipids and glycerol anhydrous, Baxter healthcare Corp.), Isolyte® M in dextrose (multi-electrolyte injection in 5% dextrose, B. Braun Medical Inc.), Isolyte® P in dextrose (multi-electrolyte injection in 5% dextrose, B. Braun Medical Inc.), Isolyte® S in dextrose (multi-electrolyte injection, B. Braun Medical Inc.), Kabiven® (amino acids, electrolytes, dextrose and lipid injectable emulsion, Fresenius Kabi), Liposyn® II (intravenous fat emulsion contains 5% safflower oil, 5% soybean oil, up to 1.2% egg phosphatides, Hospira, Inc.), NephrAmine® (essential amino acid injection, B. Braun Medical Inc.), Novamine® (15% amino acids injection of essential and nonessential amino acids, Hospira Inc.), Nouress® (cysteine hydrochloride injection, Avadel Legacy Pharmaceuticals, LLC), Nutrilipid® (plant based fat emulsion, B. Braun Medical Inc.), Nutrilyte® Pro (multi-electrolyte injection, American Regent Inc.), Nutrilyte® II (multi-electrolyte injection, American Regent Inc.), Omegaven® (fish oil triglycerides, Fresenius Kabi), Perikabiven® (amino acids, electrolytes, dextrose and lipid injectable emulsion, Fresenius Kabi USA, LLC), Plasma-Lyte® 56 (multiple electrolytes and dextrose injection, Type 1, USP Baxter Healthcare Corporation) Plasma-Lyte 148 ® (multiple electrolytes and dextrose injection, Type 1, USP Baxter Healthcare Corporation), Procalamine® (3% amino acid and 3% glycerin injection with electrolytes, B. Braun Medical Inc.), Plenamine® (15% amino acid injection, B. Braun Medical Inc.), Premasol® (sulfite-free amino acid injection, Baxter Healthcare Corp.), Prosol® (amino acids injection, Baxter Healthcare Corp.), Renamin® (amino acid Injection, Baxter Healthcare Corp.), Ringer's injection, SMOFlipid (fish oil and plant based fat emulsion, Fresenius Kabi), Synthamin® 17 (10% amino acid infusion product, Baxter Healthcare Corp.), Travasol® (amino acid injection for intravenous use, Baxter Healthcare Corp.), TrophAmine® (amino acid injection, B. Braun Medical Inc.), dextrose, sodium chloride, calcium chloride, potassium chloride, magnesium chloride, sodium acetate, or a combination thereof.

Dosing recommendations for pediatric patients is based on body weight and ranges from about 0.2 mL to about 0.8 mL per day as shown in Table 3 above, where MDD refers to maximum daily dose.

Parenteral nutrition has become an integral part of the support of the neonate who is either unable to receive or tolerate enteral feeding. Feeding practices are generally based on birth weight, with the smallest infants receiving parenteral nutrition for the longest time after birth. Generally, neonates include infants in the first four weeks after birth. Term neonates have an estimated weight of from about 3 kg to less than 5 kg and preterm neonates have an estimated weight of less than 3 kg. Neonates also include very low birth weight (those having a weight of less than 1500 g) and extremely low birth weight (those having a weight of less than 1000 g). These neonate infants are susceptible to growth failure in postnatal life if nutritional demands are not met. Poor postnatal growth in preterm infants is associated with adverse neurodevelopmental outcomes during childhood. Thus, early parental nutrition is of paramount importance to provide appropriate protein and energy in neonates, both preterm and term, when enteral nutrition is not feasible or is suboptimal. We have, therefore, prepared a stable parenteral nutrition that can be used in a wide spectrum of patients, adult, pediatric and neonate.

The nutrient components of PN include dextrose, amino acids, fat, electrolytes, multivitamins, trace elements and water. Regarding the content and amounts of multivitamins and trace elements in PN solutions or compositions compliance with recommendations by the American Society for Parenteral and Enteral Nutrition (A.S.P.E.N.) is followed. In accordance with A.S.P.E.N. recommendations, an injectable composition is provided which is a parenteral nutrition. The parenteral nutrition or parenteral nutrition composition of this application comprises at least one of an amino acid, a dextrose, a lipid, an electrolyte or a mixture thereof and a trace element component which comprises, consists essentially of or consists of at least one of zinc, copper, selenium, and manganese. This means that, in some cases, the parenteral nutrition contains only one of the trace elements, for example only zinc or copper or manganese or selenium. In other cases, the parenteral nutrition can include more than one trace element, for example, only zinc and copper or a mixture of all four of these elements.

In various embodiments, before any trace elements compositions are added to the parenteral nutrition, the parenteral nutrition can comprise trace amounts of zinc, copper, manganese, and chromium from other sources, for example water for injection and/or the container of the injectable composition. For example, in some cases, the parenteral nutrition can comprise inherently and/or as impurities zinc in an amount of less than about 750 μg/L, copper in an amount of less than 75 μg/L, selenium in an amount of less than 15 μg/L, manganese in an amount of less than 13.7 μg/L and chromium in an amount of less than 0.25 μg/mL.

In various aspects, the parenteral nutrition comprises, consists essentially of or consists of from about 900 μg to about 4,000 μg of zinc, from about 40 μg to about 400 μg of copper, from about 4 μg to about 90 μg of selenium, and from about 1 μg to about 80 μg of manganese per about 250 mL to 4000 mL of parenteral nutrition. In some embodiments, the parenteral nutrition comprises, consists essentially of, or consists of 3,000 μg of zinc, 300 μg of copper, 60 μg of selenium, and 55 μg of manganese per about 250 mL to 4000 mL of parenteral nutrition. In other embodiments, the parenteral nutrition comprises, consists essentially of, or consists of 1,000 μg of zinc, 60 μg of copper, 6 μg of selenium, and 3 μg of manganese per about 250 mL to 4000 mL of parenteral nutrition.

The elemental zinc can be provided by zinc sulfate or zinc heptahydrate. Copper can be provided by cupric sulfate or cupric sulfate pentahydrate. Manganese can be sourced from manganese sulfate or manganese sulfate monohydrate. Selenium can be provided by selenious acid. Thus, in many cases, in the parenteral nutrition, zinc comprises zinc sulfate or zinc sulfate heptahydrate in an amount of from about 13.1 mg to about 13.3 mg, copper comprises, consists essentially of or consists of cupric sulfate or cupric sulfate pentahydrate in an amount of from about 1.1 mg to about 1.2 mg, manganese comprises manganese sulfate or manganese sulfate monohydrate in an amount of from about 0.16 mg to about 0.18 mg and selenium comprises selenious acid in an amount of from about 95 μg to about 99 μg per about 250 mL to 4000 mL of parenteral nutrition.

In some embodiments, in the parenteral nutrition, the zinc sulfate or zinc sulfate heptahydrate comprises, consists essentially of, or consists of an amount of about 13.2 mg, the cupric sulfate or the cupric sulfate pentahydrate comprises, consists essentially of or consists of an amount of about 1.179 mg, the manganese sulfate or manganese sulfate monohydrate comprises, consists essentially of or consists of an amount of about 0.0169 mg and the selenious acid comprises, consists essentially of or consists of an amount of about 98 µg.

In some embodiments, each trace element can be added to a PN solution, one at a time and the injection composition of this application can contain only one of these trace elements, for example, only zinc, copper, manganese, or selenium. This approach allows for tailoring of a PN solution to the needs of a specific patient in need who might have a zinc deficiency only, for example, but is not deficient in copper, manganese, or selenium.

In some embodiments, a selenious acid injection, USP can be indicated for use as a supplement to intravenous solutions given for parenteral nutrition (PN). Administration of selenium in PN solutions helps to maintain plasma selenium levels and to prevent depletion of endogenous stores and subsequent deficiency symptoms. Each mL contains 98.0 µg of selenious acid, USP (equivalent to 60 µg of elemental selenium), nitric acid, national formulary (NF) for pH adjustment (1.8 to 2.4) and water for injection, USP quantity sufficient (q.s). In some embodiments, the trace element composition comprises selenium or selenious acid and has a pH of about 3.5 to about 7.9.

In many aspects, selenium is present in the same concentration of 60 µg of elemental selenium per mL in the injectable composition comprising beside selenium, the multi-trace product which contains zinc sulfate heptahydrate 13.20 mg (equivalent to 3 mg zinc), cupric sulfate pentahydrate 1.18 mg (equivalent to 0.3 mg copper), and manganese sulfate monohydrate 169 µg (equivalent to 55 µg manganese) sulfuric acid for pH adjustment and water for injection q.s. Since selenious acid injection, USP could be administered in parenteral solutions as both, single and a component of multi-trace solutions, it was deemed appropriate to utilize the study of the trace elements injection which also contains zinc, copper and manganese USP for selenious acid injection, USP.

In many aspects, the parenteral nutrition includes at least one of (i) the amino acid which comprises lysine hydrochloride, phenylalanine, leucine, valine, threonine, methionine, isoleucine, tryptophan, alanine, arginine, glycine, proline, histidine, glutamic acid, serine, aspartic acid, tyrosine or a mixture thereof; (ii) the dextrose which comprises dextrose monohydrate; (iii) the lipid which comprises soybean oil, phospholipid, glycerin or a mixture thereof; (iv) the electrolyte which comprises sodium acetate trihydrate, potassium chloride, sodium chloride, potassium acetate, sodium glycerophosphate anhydrous, magnesium sulfate heptahydrate, calcium chloride dihydrate, calcium gluconate or a mixture thereof and (v) water, generally water for injection. In various aspects, the parenteral nutrition solution is nonpyrogenic.

In various aspects, the parenteral nutrition has a pH that varies is from about 3.5 to about 7.9. In some cases, the pH can be from about 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.3, 5.5., 5.7, 5.8, 5.9, 6.0, 6.1, 6.2, 6.3, 6.4, 6.5, 6.7, 6.8, 6.9, 7.0, 7.1, 7.2, 7.3, 7.4, 7.5, 7.6, 7.7, 7.8 to about 7.9.

It has been surprisingly found that when stored from about 2° C. to about 8° C. for up to about 14 days, the parenteral nutrition which includes the trace element composition of this application is stable remaining in a state or condition that is suitable for administration to a patient and without undergoing a substantial change in the potency of the active agent in the formulation over this specified time period.

Further, when stored from about 2° C. to about 8° C. for about 14 days the parenteral nutrition maintained a pH from about 5.50 to about 5.90. When stored from about 2° C. to about 8° C. for about 14 days, the parenteral composition of this application comprises, consists essentially of or consists of at least one of (i) no more than 12 particle per mL that are greater than 10 µm; or (ii) no more than 2 particle per mL that are greater than 25 µm. Moreover, when the parenteral nutrition of this disclosure is stored from about 2° C. to about 8° C. for about 14 days, it was surprisingly found that it did not exhibit any significant microbial growth with respect to such microbes as *S. aureus, P. aeruginosa, E. coli, C. albicans, A. brasiliensis* or a mixture thereof.

Generally parenteral nutrition can be prepared in a dual or triple chamber infusion bag which can have a separate port for the addition of trace elements prior to administration. Aluminium (Al) toxicity in parenteral nutrition solutions (PNS) has been a problem for many patients with impaired kidney function who frequently are in need of parenteral nutrition. In accordance with 21CFR201.323 (revised as of Apr. 1, 2019), regarding aluminum content, the Federal Drug Administration prescribes that the parenteral nutrition solution must contain a warning that the solution contains no more than 25 mcg/L of aluminum which may reach toxic levels with prolonged administration in patients with renal impairment. Preterm infants are at greater risk because their kidneys are immature, and they require large amounts of calcium and phosphate solutions which contain aluminum. Patients with renal impairment, including preterm infants, who receive parenteral levels of aluminum at greater than 4 to 5 mcg/kg/day, accumulate aluminum at levels associated with central nervous system and bone toxicity. Tissue loading may occur at even lower rates of administration. Nevertheless, whether or not the parenteral nutrition of this disclosure includes the trace elements composition as a component, the amount of aluminum should be kept in a daily exposure amount from about 0.1 µg/kg, 0.2, 0.3, 0.4, 0.5 to about 0.6 µg/kg, in any event not to exceed 0.6 µg/kg. In many cases, the parenteral nutrition of this application does not contain any aluminum and/or chromium as impurities.

In some embodiments, parenteral nutrition includes multivitamins, such as for example, vitamins, A, D, E, C, B1, B2, B6, B12, niacinamide, dexpanthenol, biotin and/or folic acid. In other embodiments, the trace elements when added to the PN may interact with the vitamins in the PN and may cause precipitation. Thus, in some embodiments, the injectable composition containing trace elements is added to parenteral nutrition that does not contain any vitamins.

In some embodiments, to the parenteral nutrition comprising at least one of an amino acid, a dextrose, a lipid, an electrolyte or a mixture thereof and a trace element, one or more injectable vitamins can be added. These one or more injectable vitamins can be added individually or together to the parenteral nutrition. These vitamins include one or more of vitamin A (e.g., retinol), vitamin D (e.g., ergocalciferol), vitamin E (e.g., dl-alpha-tocopheryl acetate), vitamin K (e.g., phytonadione), vitamin C (e.g., ascorbic acid), niacinamide, vitamin B2 (e.g., as riboflavin 5-phosphate sodium), vitamin B1 (e.g., thiamine), vitamin B6 (e.g., pyridoxine HCl), dexpanthenol (e.g., d-pantothenyl alcohol), biotin, folic acid, B12 (e.g., cyanocobalamin), or a combination thereof.

An example of vitamins for injection for adults (INFU-VITE® Adult) that can be added to the parenteral nutrition before or after the addition of the trace elements include those vitamins in a two vial system listed below.

| Vial 1* | |
|---|---|
| Ingredient | Amount per Unit Dose |
| Fat Soluble Vitamins** | |
| Vitamin A (retinol) | 1 mg$^a$ |
| Vitamin D (ergocalciferol) | 5 mcg$^b$ |
| Vitamin E (dl-alpha-tocopheryl acetate) | 10 mg$^c$ |
| Vitamin K (phytonadione) | 150 mcg |
| Water Soluble Vitamins | |
| Vitamin C (ascorbic acid) | 200 mg |
| Niacinamide | 40 mg |
| Vitamin B2 (as riboflavin 5-phosphate sodium) | 3.6 mg |
| Vitamin B1 (thiamine) | 6 mg |
| Vitamin B6 (pyridoxine HCl) | 6 mg |
| Dexpanthenol (d-pantothenyl alcohol) | 15 mg |

*With 30% propylene glycol and 2% gentisic acid ethanolamide as stabilizers and preservatives; sodium hydroxide for pH adjustment; 1.6% polysorbate 80; 0.028% polysorbate 20; 0.002% butylated hydroxytoluene; 0.0005% butylated hydroxyanisole.
**Fat soluble vitamins A, D, E and K are water solubilized with polysorbate 80.
$^a$1 mg vitamin A equals 3,300 USP units.
$^b$5 mcg ergocalciferol equals 200 USP units.
$^c$10 mg vitamin E equals 10 USP units.

| Vial 2* | |
|---|---|
| Biotin | 60 mcg |
| Folic acid | 600 mcg |
| B12 (cyanocobalamin) | 5 mcg |

*With 30% propylene glycol; and citric acid, sodium citrate, and sodium hydroxide for pH adjustment.

An example of pediatric injectable vitamins that can be added to the parenteral nutrition before or after the addition of the trace elements include those found in INFUVITE® PEDIATRIC Each 4 mL of Vial 1 contains 10 vitamins (shown below).

Active Ingredients in 4 mL of Vial 1

| Active Ingredient | Quantity |
|---|---|
| Ascorbic acid (Vitamin C) | 80 mg |
| Vitamin A* (as palmitate) | 2,300 IU (equals 0.7 mg) |
| Vitamin D3* (cholecalciferol) | 400 IU (equals 10 mcg) |
| Thiamine (Vitamin B1) (as the hydrochloride) | 1.2 mg |
| Riboflavin (Vitamin B2) (as riboflavin 5-phosphate sodium) | 1.4 mg |
| Pyridoxine HCl (Vitamin B6) | 1 mg |
| Niacinamide | 17 mg |
| Dexpanthenol (as d-pantothenyl alcohol) | 5 mg |
| Vitamin E* (dl-α-tocopheryl acetate) | 7 IU (equals 7 mg) |
| Vitamin K1* | 0.2 mg |

*Polysorbate 80 is used to water solubilize the oil-soluble vitamins A, D, E, and K.

Inactive ingredients in Vial 1: 50 mg polysorbate 80, sodium hydroxide and/or hydrochloric acid for pH adjustment, and water for injection. Each 1 mL of Vial 2 contains 3 vitamins (see shown below).

Active Ingredients in 1 mL of Vial 2

| Active Ingredient | Quantity |
|---|---|
| Folic acid | 140 mcg |
| Biotin | 20 mcg |
| Vitamin B12 (cyanocobalamin) | 1 mcg |

Inactive ingredients in Vial 2: 75 mg mannitol, citric acid and/or sodium citrate for pH adjustment and water for injection.

Container of the Trace Elements Injectable Composition

In various embodiments, the injectable composition containing trace elements is disposed in a container. The container can have a variety of volumes. Typically, the container for the trace elements injectable composition before it is added to a parenteral solution can have a volume of from about 1 mL to about 10 mL. In some examples, the container can have a volume of from about 1 mL, 2, 3, 4, 5, 6, 7, 8, 9 to about 10 mL.

Containers in which the trace elements composition can be stored include any container that is suitable for storing a pharmaceutical. Typical containers can be inert to the trace elements composition. In some embodiments, treated glass containers such as siliconized glass containers are also useful. In some embodiments, plastic containers can also be used that are inert and/or are treated or coated to be inert. Suitable containers include vials, ampules, bottles, cartridges, syringes, pre-filled syringes, plastic IV bags, or the like. The container can be sealed with a closure, such as, for example, a rubber stopper, plunger, lid, top or the like. Suitable inert or non-reactive stoppers may be obtained from several commercial manufacturers. In general, the closures can be made with inert, non-reactive materials with little to no leachables. In some embodiments, closures also include those that are coated or treated with inert materials such as siliconized polymer or Teflon/fluoropolymer coated/treated closures. By way of example and not in limitation of the present application, rubber closures that are suitable in the present application include bromobutyl rubber, chlorobutyl rubber, fluoropolymers, silicones, siliconized bromobutyl rubber, and/or siliconized chlorobutyl rubber.

Non-reactive, non-elastomeric closures are also useful for the trace elements composition. For example, non-rubber closures include metal closures, or plastics such as polyethylene, polypropylene, nylon, polyurethane, polyvinylchloride, polyacrylates, polycarbonates, or the like that cause little to no degradation to the trace elements composition or that are treated or coated so as to cause little or no degradation of the trace elements composition.

In many aspects, useful containers for the injectable compositions of this disclosure include a single use vial or ampule or the containers comprise a vial having a barrier coated stopper and/or an aluminum cap. In some embodiments, the vial or ampule comprises molded glass or polypropylene. In other cases, the container for the injectable compositions of this disclosure can be made of a variety of materials. Non-limiting materials can include glass, a plastic (e.g., polyethylene, polypropylene, polyvinyl chloride, polycarbonate, etc.), the like, or a combination thereof provided that it can both prevent oxygen penetration and minimize aluminum, heavy metals and anions contamination to the composition. In certain embodiments, the container is fabricated from multilayered plastic (PL 2501, PL 2040), also known as a galaxy container, a plastic container primarily for intravenous use. Solutions are in contact with the polyethylene layer of the container and can leach out certain chemical components of the plastic in very small amounts within the expiration period.

In other aspects, the container can be fabricated from glass as a single use 1 mL vial, for example, a Type I glass vial for injectable products. In some aspects, the pharmaceutical compositions of this disclosure can also be stored in glass vials or ampules, for example, single use 1 mL glass vials or ampules. In various embodiments, the container can be Type I glass (e.g., molded glass, tubing glass, glass coated with silica, etc.), plastic (e.g., polymeric materials such as polypropylene, COC, COP, multi-shell, etc.) or the like. In some embodiments, Type I glass can be a borosilicate glass, which is relatively inert with good chemical resistance.

In some cases, the injectable composition is dispensed into a container that can be a single use container, for example, a single use vial or ampule or the container comprises a vial having a barrier coated stopper and/or an aluminum cap. As described above, the vial or ampule can be made of molded glass or polypropylene. The container may, optionally, further comprise a light barrier. In certain embodiments, the light barrier can be an aluminum material disposed over a pouch.

The injectable composition of trace elements can be dispensed, for example, in 1 mL single dose vial or can be dispensed in 10 mL multi-dose vials. In some cases, the vials can be prepared of Pyrex glass or sprayed or coated with silica or can be made of plastic material. This is to minimize the amount of aluminum that may potentially be leaching from a glass vial to a daily exposure amount not to exceed 0.6 μg/kg of body weight of a patient in need of trace elements treatment or no more than 25 μg/L of intravenous (IV) infusion for parenteral nutrition. In some cases, the daily exposure amount of aluminum can vary from about 0.1 μg/kg to about 0.6 μg/kg of aluminum. In other cases, there is no detectable aluminum present in the injectable compositions of this application.

To ensure that the amount of aluminum in a multicomponent PN is maintained below 25 μg/L (CFR 201.323), choosing a low aluminum content vial such as Gerresheimer Gx®33 is expected to reduce the amount of aluminum leached from a glass container. The West 4432 FluroTec® B2-40 coated stopper was selected because the barrier technology of the FluroTec® film, in combination with the B2-40 coating, utilized in the West 4432 FluroTec® B2-40 stopper can significantly reduce potential sources of particulate contamination, specifically by reducing inorganic and organic leachable substances and by providing lubricity without the need for free silicone oil. Using glass vials with or without a coated stopper provided a targeted shelf-life of 24 months.

The container in which the injectable compositions are held may affect the level of certain components. In certain embodiments, the injectable composition can be enclosed in a single-use container. These containers can include, for example, vials, ampules, or syringes. As previously discussed, the pH range for the injectable composition of either parenteral nutrition and/or injectable composition comprising trace elements varies from about 1.0 to about 7. This pH may disrupt the plastic coating or silicon coating inside the glass container and aluminum, heavy metals and anions could leach during the shelf life of the product, especially over prolonged storage of the product.

Elemental impurities monitored in the finished drug products described in this disclosure include without limitation Cd, Pb, As, Hg, Co, V, Ni, Tl, Au, Pd, Ir, Os, Rh, Ru, Se, Ag, Pt, Li, Sb, Ba, Mo, Cu, Sn, and Cr. In some embodiments, the injectable composition comprising trace element or the parenteral nutrition comprising the injectable composition include 0.0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, to about 5.0 ppb of these impurities. However, the levels of specific metals ions are monitored in the finished drug product units over the entire shelf life but are not quantified in the bulk Water for Injection (WFI), USP used to prepare the batch. Rather, the level of soluble metals and any other electrolytes is measured in the bulk WFI, USP via measurement of conductivity.

In some embodiments, the one or more trace elements are indicated for use as a supplement to intravenous solutions given for parenteral nutrition. Administration of the solution in parenteral TPN solutions helps to maintain plasma levels of one or more elements: zinc, copper, manganese, selenium or optionally chromium and to prevent depletion of endogenous stores of these trace elements and subsequent deficiency symptoms. In some embodiments, the one or more trace elements can be used to maintain, supplement or increase one or more trace elements: zinc, copper, manganese, selenium or optionally chromium.

The trace element can be elemental and sourced from any salt, hydrate, and/or solvate forms thereof. For example, the elemental zinc can be from, for example, zinc gluconate trihydrate, zinc gluconate, zinc chloride, zinc sulfate, zinc sulfate heptahydrate, zinc oxide, zinc sulfide, zinc trisodium, zinc carbonate, zinc acetate, zinc citrate, zinc lactate, zinc hydroxide or a combination thereof. For example, the elemental manganese can be from, for example, manganese sulfate, manganese sulfate monohydrate, manganese chloride, manganese gluconate, manganese glycerophosphate, manganese carbonate, manganese hydroxide, or a combination thereof. For example, the elemental copper can be from, for example, cupric sulfate, cupric sulfate pentahydrate, cupric hydroxide, cupric oxide, copper carbonate, copper citrate, copper gluconate, or a combination thereof. For example, the elemental selenium can be from, for example, selenious acid, sodium selenite, disodium selenite, sodium hydrogen selenite, potassium selenite, zinc selenite, copper selenite, manganese selenite or a combination thereof. In some embodiments, the zinc selenite, copper selenite, or manganese selenite or a combination thereof are not readily soluble in water but at a pH of between about 1.5 to about 3.5, the zinc selenite, copper selenite, or manganese selenite or a combination are water soluble. For example, the elemental chromium can be from, for example, chromium trichloride, chromium trichloride hexahydrate, chromium trisulfate or a combination thereof.

The trace elements can be in the trace elements composition in the following ratios:

| Product | Ratio elemental Zn to elemental Cu | Ratio elemental Zn to elemental Mn | Ratio elemental Zn to elemental Se |
| --- | --- | --- | --- |
| MTE-4® | 1 mg Zn to 0.4 mg Cu Ratio: 2.5 to 1 | 1 mg Zn to 0.1 mg Mn Ratio: 10 to 1) | N/A |
| MTE-4® Conc. | 5 mg Zn to 1 mg Cu Ratio: 5 to 1 | 5 mg Zn to 0.5 mg Mn Ratio: 10 to 1 | N/A |

-continued

| Product | Ratio elemental Zn to elemental Cu | Ratio elemental Zn to elemental Mn | Ratio elemental Zn to elemental Se |
|---|---|---|---|
| MTE-4 ® Neonatal | 1.5 mg Zn to 0.1 mg Cu Ratio: 15 to 1 | 1.5 mg Zn to 0.025 mg Mn Ratio: 60 to 1 | N/A |
| MTE-4 ® Pediatric | 1 mg Zn to 0.1 mg Cu Ratio: 10 to 1 | 1 mg Zn to 0.025 mg Mn Ratio: 40 to 1 | N/A |
| MTE-5 ® | 1 mg Zn to 0.4 mg Cu Ratio: 2.5 to 1 | 1 mg Zn to 0.1 mg Mn Ratio: 10 to 1 | 1 mg Zn to 0.02 mg Se Ratio: 50 to 1 |
| MTE-5 ® Conc. | 5 mg Zn to 1 mg Cu Ratio: 5 to 1 | 5 mg Zn to 0.5 mg Mn Ratio: 10 to 1 | 5 mg Zn to 0.06 mg Se Ratio: 83.3 to 1 |

These ratios are elemental to elemental ratios (e.g., elemental Zn to elemental Cu, elemental Zn to elemental Mn, etc.). In some embodiments, these ratios can also be the ratios for the newer formulations that have no or little chromium. In some embodiments, the trace elements are in a ratio of: elemental zinc to elemental copper from about 100:1, 80:1, 70:1, 60:1, 50:1, 30:1, 20:1, 15:1, 10:1, 5:1, 2.5:1 to about 2:1; elemental zinc to elemental manganese in a ratio from about 4000:1, 3,000:1, 2,000:1, 1,000:1, 500:1, 200:1, 100:1, 60:1, 55:1, 50:1, 45:1, 40:1, 35:1, 30:1, 25:1, 20:1, 15; 1, 10:1 to about 5:1; elemental zinc to elemental selenium in a ratio from about 1000:1, 500:1, 200:1, 100:1, 90:1, 85:1, 83.3:1, 80:1, 75:1, 70:1, 65:1, 60:1, 55:1, 50:1, 45:1, 40:1, 35:1, 30:1, 25:1, 20:1, 15:1, 10:1 to about 9:1; elemental copper to elemental selenium in a ratio from about 100:1, 50:1, 20:1, 15:1, 10:1, 5:1, 3:1, 2:1, 1:1 to about 0.4:1; elemental copper to elemental manganese in a ratio from about 400:1, 300:1, 200:1, 100:1, 90:1, 85:1, 80:1, 75:1, 70:1, 65:1, 60:1, 55:1, 50:1, 45:1, 40:1, 35:1, 30:1, 25:1, 20:1, 15:1, 10:1, 5.5:1, 5:1, 2.5:1, 2:1, 1:1 to about 0.5:1; and/or elemental selenium to elemental manganese in a ratio from about 100:1, 90:1, 75:1, 50:1, 30:1, 20:1, 10:1, 5:1, 3; 1, 2:1, 1.1:1, 1:1, 0.5:1, 0.4:1 to about 0.05:1.

In some embodiments, the trace elements can be in the trace elements composition in the following elemental ratios: Zn/Cu: 10:1, Zn/Se: 50:1, Zn/Mn: 55:1, Cu/Se: 5:1, Cu/Mn: 5.5:1, and/or Se/Mn: 1.1:1. In some embodiments, these can lead to the trace elements composition stability and the parenteral nutrition stability.

Exemplary trace elements compositions for use in the current application include Multitrace®-4, available from American Regent Shirley, NY, USA.

| | Multitrace ®-4 (Trace Elements Injection 4, USP) 10 mL Multiple Dose Vial (Preserved with 0.9% Benzyl Alcohol) | | Multitrace ®-4 Concentrate (Trace Elements Injection 4, USP) 1 mL Single Dose Vial (Preservative Free) | Multitrace ®-4 Concentrate (Trace Elements Injection 4, USP) 10 mL Multiple Dose Vial (Preserved with 0.9% Benzyl Alcohol) |
|---|---|---|---|---|
| Trace Elements | Content of Trace Elements/1 mL | Trace Elements | Content of Trace Elements/1 mL | Trace Elements |
| Zinc (as Sulfate) | 1 mg | Zinc (as Sulfate) | 5 mg | Zinc (as Sulfate) |
| Copper (as Sulfate) | 0.4 mg | Copper (as Sulfate) | 1 mg | Copper (as Sulfate) |
| Manganese (as Sulfate) | 0.1 mg | Manganese (as Sulfate) | 0.5 mg | Manganese (as Sulfate) |
| Chromium (as Chloride) | 4 mcg | Chromium (as Chloride) | 10 mcg | Chromium (as Chloride) |
| In Water for Injection, USP | N/A | In Water for Injection, USP | N/A | In Water for Injection, USP |
| pH | Solution may be adjusted with Sulfuric Acid and/or Sodium Hydroxide | pH | Solution may be adjusted with Sulfuric Acid and/or Sodium Hydroxide | pH |

| | Multitrace ®-4 Concentrate (Trace Elements Injection 4, USP) 10 mL Multiple Dose Vial (Preserved with 0.9% Benzyl Alcohol) | Multitrace ®-4 Neonatal (Trace Elements Injection 4, USP) 2 mL Single Dose Vial (Preservative Free) | | Multitrace ®-4 Pediatric (Trace Elements Injection 4, USP) 3 mL Single Dose Vial (Preservative Free) | |
|---|---|---|---|---|---|
| | Content of Trace Elements/1 mL | Trace Elements | Content of Trace Elements/1 mL | Trace Elements | Content of Trace Elements/1 mL |
| | 5 mg | Zinc (as Sulfate) | 1.5 mg | Zinc (as Sulfate) | 1 mg |
| | 1 mg | Copper (as Sulfate) | 0.1 mg | Copper (as Sulfate) | 0.1 mg |
| | 0.5 mg | Manganese (as Sulfate) | 25 mcg | Manganese (as Sulfate) | 25 mcg |
| | 10 mcg | Chromium (as Chloride) | 0.85 mcg | Chromium (as Chloride) | 1 mcg |

| | | | | | |
|---|---|---|---|---|---|
| N/A | In Water for Injection, USP | N/A | In Water for Injection, USP | N/A | |
| Solution may be adjusted with Sulfuric Acid and/or Sodium Hydroxide | pH Solution may be adjusted with Sulfuric Acid and/or Sodium Hydroxide | | pH Solution may be adjusted with Sulfuric Acid and/or Sodium Hydroxide | | |

Exemplary trace elements compositions for use in the current application can also include Multitrace®-5, available from American Regent Shirley, NY, USA.

| Multitrace ®-5 (Trace Elements Injection 5, USP) 10 mL Multiple Dose Vial (Preserved with 0.9% Benzyl Alcohol) | | Multitrace ®-5 Concentrate (Trace Elements Injection 5, USP) 1 mL Single Dose Vial (Preservative Free) | | Multitrace ®-5 Concentrate (Trace Elements Injection 5, USP) 10 mL Multiple Dose Vial (Preserved with 0.9% Benzyl Alcohol) | |
|---|---|---|---|---|---|
| Trace Elements | Content of Trace Elements/1 mL | Trace Elements | Content of Trace Elements/1 mL | Trace Elements | Content of Trace Elements/1 mL |
| Zinc (as Sulfate) | 1 mg | Zinc (as Sulfate) | 5 mg | Zinc (as Sulfate) | 5 mg |
| Copper (as Sulfate) | 0.4 mg | Copper (as Sulfate) | 1 mg | Copper (as Sulfate) | 1 mg |
| Manganese (as Sulfate) | 0.1 mg | Manganese (as Sulfate) | 0.5 mg | Manganese (as Sulfate) | 0.5 mg |
| Chromium (as Chloride) | 4 mcg | Chromium (as Chloride) | 10 mcg | Chromium (as Chloride) | 10 mcg |
| Selenium (as Selenious Acid) | 20 mcg | Selenium (as Selenious Acid) | 60 mcg | Selenium (as Selenious Acid) | 60 mcg |
| In Water for Injection, USP | N/A | In Water for Injection, USP | N/A | In Water for Injection, USP | N/A |
| pH | Solution may be adjusted with Sulfuric Acid and/or Sodium Hydroxide | pH | Solution may be adjusted with Sulfuric Acid | pH | Solution may be adjusted with Sulfuric Acid |

Exemplary trace elements compositions that can be used in the current application can include those without chromium some listed below.

| Trace Elements Injection 3, USP (No Chromium) 10 mL Multiple Dose Vial (Preserved with 0.9% Benzyl Alcohol) | | Trace Elements Injection 3, USP (No Chromium) 1 mL Single Dose Vial (Preservative Free) | | Trace Elements Injection 3, USP (No Chromium) 10 mL Multiple Dose Vial (Preserved with 0.9% Benzyl Alcohol) | |
|---|---|---|---|---|---|
| Trace Elements | Content of Trace Elements/1 mL | Trace Elements | Content of Trace Elements/1 mL | Trace Elements | |
| Zinc (as Sulfate) | 1 mg | Zinc (as Sulfate) | 5 mg | Zinc (as Sulfate) | |
| Copper (as Sulfate) | 0.4 mg | Copper (as Sulfate) | 1 mg | Copper (as Sulfate) | |
| Manganese (as Sulfate) | 0.1 mg | Manganese (as Sulfate) | 0.5 mg | Manganese (as Sulfate) | |
| In Water for Injection, USP | | N/A | | In Water for Injection, USP | |
| pH | Solution may be adjusted with Sulfuric Acid and/or Sodium Hydroxide | pH | Solution may be adjusted with Sulfuric Acid and/or Sodium Hydroxide | pH | |

Trace Elements Compositions having 4 trace elements with no chromium are shown below.

| | Trace Elements Injection 3, USP (No Chromium) 10 mL Multiple Dose Vial (Preserved with 0.9% Benzyl Alcohol) | | Neonatal Trace Elements Injection 3, USP (No Chromium) 2 mL Single Dose Vial (Preservative Free) | | Pediatric Trace Elements Injection 3, USP (No Chromium) 3 mL Single Dose Vial (Preservative Free) |
|---|---|---|---|---|---|
| | Content of Trace Elements/1 mL | Trace Elements | Content of Trace Elements/1 mL | Trace Elements | Content of Trace Elements/1 mL |
| | 5 mg | Zinc (as Sulfate) | 1.5 mg | Zinc (as Sulfate) | 1 mg |
| | 1 mg | Copper (as Sulfate) | 0.1 mg | Copper (as Sulfate) | 0.1 mg |
| | 0.5 mg | Manganese (as Sulfate) | 25 mcg | Manganese (as Sulfate) | 25 mcg |
| | In Water for Injection, USP | | N/A | | In Water for Injection, USP |
| | Solution may be adjusted with Sulfuric Acid and/or Sodium Hydroxide | pH | Solution may be adjusted with Sulfuric Acid and/or Sodium Hydroxide | pH | Solution may be adjusted with Sulfuric Acid and/or Sodium Hydroxide |

| Trace Elements 4 Injection (No Chromium) 10 mL Multiple Dose Vial (Preserved with 0.9% Benzyl Alcohol) | | Trace Elements 4 Injection Concentrated (No Chromium) 1 mL Single Dose Vial (Preservative Free) | | Trace Elements 4 Injection Concentrated (No Chromium) 10 mL Multiple Dose Vial (Preserved with 0.9% Benzyl Alcohol) | |
|---|---|---|---|---|---|
| Trace Elements | Content of Trace Elements/1 mL | Trace Elements | Content of Trace Elements/1 mL | Trace Elements | Content of Trace Elements/1 mL |
| Zinc (as Sulfate) | 1 mg | Zinc (as Sulfate) | 5 mg | Zinc (as Sulfate) | 5 mg |
| Copper (as Sulfate) | 0.4 mg | Copper (as Sulfate) | 1 mg | Copper (as Sulfate) | 1 mg |
| Manganese (as Sulfate) | 0.1 mg | Manganese (as Sulfate) | 0.5 mg | Manganese (as Sulfate) | 0.5 mg |
| Selenium (as Selenious Acid) | 20 mcg | Selenium (as Selenious Acid) | 60 mcg | Selenium (as Selenious Acid) | 60 mcg |
| In Water for Injection, USP | N/A | In Water for Injection, USP | N/A | In Water for Injection, USP | N/A |
| pH | Solution may be adjusted with Sulfuric Acid and/or Sodium Hydroxide | pH | Solution may be adjusted with Sulfuric Acid | pH | Solution may be adjusted with Sulfuric Acid |

Headspace Oxygen

In certain embodiments, the trace elements further comprise within the container, headspace gas that includes oxygen in an amount of from about 0.5% v/v to about 5.0% v/v, or from about 0.5% v/v to about 4.0% v/v, or from about 0.5% v/v to about 3.5% v/v, from about 0.5% v/v to about 3.0% v/v, or from about 0.5% v/v to about 2.5% v/v, or from about 0.5% v/v to about 2.0% v/v, or from about 0.5% v/v to about 1.5% v/v, or from about 0.5% v/v to about 1.0% v/v, or in some cases from about 0.1% v/v to about 0.5% v/v, or from about 0.1% v/v to about 0.4% v/v, or from about 0.1% v/v to about 0.3% v/v, or from about 0.1% v/v to about 0.2% v/v. For the sake of clarity and the ease of discussion and measurement, these values are taken for the injectable composition at the time of its manufacture ("time zero" data point), or during and up to 1 month from time zero. Additional time points beyond the 1 month from time zero data point may provide similar headspace oxygen levels.

Without wishing to be bound by a particular theory, the dissolved oxygen levels, and the head space oxygen levels within a sealed container of injectable compositions described herein may reach an equilibrium at some time point during its shelf-life. Such equilibrium may be maintained for a very short time, i.e., for a few seconds, or for a very long time, i.e., for several months. Such equilibrium may on occasion be disturbed by simple agitation. Therefore, it should be recognized that dissolved oxygen levels and headspace oxygen levels may fluctuate from one time point to another in terms of absolute numbers. However, the numbers are expected to stay within the ranges disclosed herein. Occasionally, one number (e.g., dissolved oxygen) may exceed or fall out of a certain range (e.g., from about 0.5 to about 3.0 PPM) at a 15 day time point but may fall within that range at some other time point (e.g., 30 day time point, or later). Therefore, in some aspects, the ranges, subranges, and specific data points disclosed and discussed herein are suitable for time points beyond the time zero- and 1-month time points. In one aspect, the time points could be extended to from about 2 months, 3 months, 6 months, 9 months, 12 months, 15 months, 18 months, and about 24 months.

In some cases, the total amount of oxygen in the sealed container may be an appropriate measure to evaluate the stability of the injectable compositions. For example, the total amount of oxygen within the container may be arrived at by adding up the amount of dissolved oxygen in the carrier and the amount of head space oxygen. These values can also be expressed independently in separate units (i.e., dissolved oxygen as ppm and head space oxygen as % v/v). An example would be that the parenteral nutrition or the injectable composition of trace elements contains a dissolved oxygen level of from about 0.0 ppm to 5.0 ppm, more specifically, from about 0.0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, to about 5.0 ppm and a head space oxygen level of about 0.5% v/v to about 4.0% v/v. In certain embodiments, the total amount of oxygen within the container is expected to increase upon filling into vials due to the inherent aeration of the drug product during filling (e.g., splashing). Based on what has been seen for other drug products, the dissolved oxygen in the finished units (e.g., vials) is expected to be in the range of from about 0.0 ppm to about 7.0 ppm, more specifically, from about 0.0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9 to about 7.0 ppm.

The amount of oxygen present in the headspace of the container can be controlled by filling the headspace with an inert gas, such as nitrogen or argon. Alternatively, the head space oxygen may be controlled by vacuum operation without using an inert gas. In another aspect, the head space oxygen may be controlled by a combination of vacuum operation and inert gas overlay. In one other aspect, the head space oxygen is controlled by repeated pulses of vacuum and inert gas overlay in tandem such that the process may start first with vacuum operation followed by inert gas overlay followed by vacuum operation. The combination of vacuum operation and inert gas overlay (or inert gas overlay and vacuum operation) is considered one pulse when both steps are used together. A typical head space control operation may comprise from one to eight pulses. Typically, there could be two, three, four, or five pulses. Each pulse could last from about one tenth of one second to five seconds or from five to fifteen seconds when conducted by automated high-speed equipment custom designed for this specific purpose. In some embodiments, the pulse may last from about 0.1 to about 2.0 seconds. In some embodiments, the pulse may last from about 0.1 to about 1.0 seconds, or from about 0.1 to about 0.4 seconds. When done using manual methods, each pulse could take up to 30-60 seconds or longer.

In many cases, the headspace oxygen of the containers useful for the injectable compositions of this disclosure include (i) from about 0.5% v/v to about 5.0% v/v from the time of manufacture to about 6 months from manufacture when stored at temperatures from 25° C. to 60° C. or (ii) from about 0.5% v/v to about 10.0% v/v from the time of manufacture to about 6 months from manufacture when stored at temperatures from 25° C. to 60° C.; and the dissolved oxygen present in the injectable composition can be in an amount from about 0.1 parts per million (ppm) to about 9 ppm from the time of manufacture to about 1 month from manufacture when stored at room temperature, wherein the composition is enclosed in a single-use container having a volume of from about 1 mL to about 10 mL.

During a manufacturing process, in one embodiment, dissolved oxygen levels are controlled via sparging with an inert gas. Additionally, a blanket of inert gas (e.g., nitrogen, argon, helium) can be maintained throughout manufacturing and storage to control atmospheric oxygen exposure, while an opaque container (stainless steel or amber glass) is selected to protect the formulation from exposure to light. In some embodiments, it was found that the trace elements injectable composition of this application containing at least one of zinc, copper, manganese and selenium or a mixture thereof, a USP injectable product, was not sensitive to oxygen and thus, a nitrogen blanket/sparging during compounding was not required during the manufacturing of the trace elements injectable composition.

In some embodiments, the injectable composition is preservative-free. As used herein, preservative-free includes compositions that do not contain any preservative. Thus, the composition does not contain, for example, benzalkonium chloride, methyl, ethyl, propyl or butylparaben, benzyl alcohol, phenylethyl alcohol, or benzethonium.

In some embodiments, one or more preservatives can be incorporated into the injectable pharmaceutical composition described in this disclosure, especially in a multi-dose injectable composition. Preservatives can be introduced into a pharmaceutical solution to kill bacteria, yeast, and mold. The bacteria, yeast, and mold can be introduced accidentally when multiple aliquots are withdrawn from a container which holds multiple doses of a medicament.

A number of preservatives are available which can kill or prevent the growth of commonly encountered contaminants; these contaminants include, but are not limited to the bacteria *P. aeruginosa, E. coli* and *S. aureus*; the yeast *C. albicans*; and the mold *A. brasiliensis*. In various embodiments, the preservative comprises benzyl alcohol in an amount of 0.9% by weight based on a total weight of the injectable composition.

The preservative or preservatives are present in an amount which is effective to impart the desired preservative characteristics and allows the final composition to comply with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products.

Method of Preparing the Injectable Compositions

The stable injectable compositions of the present application can be made by mixing from about 900 µg to about 4,000 µg of zinc, from about 40 µg to about 400 µg of copper, from about 4 µg to about 90 µg of selenium, and from about 1 µg to about 80 µg of manganese with water to form 1 mL of the injectable composition. I The components of the trace elements can be mixed in any order. For example, one or more trace elements can be added together and then mixed with water to form a solution having the desired concentration. The mixed trace elements solution pH can be adjusted to a desired value and then the pH adjusted solution can, optionally, be filtered through one or more 0.22 µm sterile filters. The filtered solution can then be filled into the desired container to form the injectable trace elements solution suitable for addition to a parenteral nutrition.

In some embodiments, the injectable compositions of one or more trace elements comprises, consists essentially of, or consists of 3,000 µg of zinc, 300 µg of copper, 60 µg of selenium, and 55 µg of manganese per 1 mL of the injectable composition. These trace element compositions are useful for applications to adult and/or pediatric patients.

A pediatric patient includes a patient known to be less than 15 years of age. In some embodiments, the pediatric patient has a weight of less than 36 kg, but greater than 10 kg of body weight.

In other embodiments, the stable injectable composition of one or more trace elements comprises, consists essentially of, or consists of 1000 µg of zinc, 60 µg of copper, 6 µg of selenium, and 3 µg of manganese per 1 mL of the injectable composition. These trace element injectable compositions are useful for applications to neonates.

A neonate includes an infant aged 1 month or younger. In some embodiments, the neonate is less than 10 kg of body weight.

In some embodiments, the new trace element compositions of the current application have reduced amounts of zinc, copper, manganese and no detectable chromium compared to the Multitrace®-5 concentrated, while the selenium amount is the same. For example, the amount of selenium for the adult Multitrace®-5 concentrated composition and the new adult/pediatric composition is the same, which is 60 mcg/mL selenium. The other trace elements in the new adult/pediatric composition of the current application are zinc, copper, and manganese, which are in reduced amounts—mainly 3000 mcg/mL zinc, 300 mcg/mL copper, 55 mcg/mL manganese, and no detectable chromium compared to the Multitrace®-5 concentrated composition as shown in Table 35.

In some embodiments, for the new neonatal composition, compared to the Multitrace®-4 neonatal composition, the zinc, copper, and manganese are in reduced amounts—mainly 1000 mcg/mL zinc, 60 mcg/mL copper, 3 mcg/mL manganese compared to the Multitrace®-4 neonatal composition. However, the selenium for the new neonatal composition is 6 mcg/mL, which is increased as shown in Table 35.

In some embodiments, both the new adult/pediatric composition and the new neonatal composition have no detectable chromium, which is unlike other commercially available compositions (e.g., ADDAMEL™, Multitrace®-5, and Multitrace®-4) as shown in Table 35.

In many aspects, the trace elements of the injectable composition are elemental metals, for example, the zinc is elemental zinc, the copper is elemental copper, the selenium is elemental selenium, the manganese is elemental manganese and the water is sterile water for injection. In other aspects, the trace elements are sourced from salts of these metals. For example, the elemental zinc is from zinc sulfate or zinc sulfate heptahydrate, the elemental copper is from cupric sulfate or cupric sulfate pentahydrate, the elemental manganese is from manganese sulfate or manganese sulfate monohydrate and the elemental selenium is from selenious acid. In these compositions, at least one of the zinc comprises from about 0.23 wt. percent to about 1.33 wt. percent, the copper comprises from about 0.05 wt. percent to about 0.13 wt. percent, the manganese comprises from about 0.026 wt. percent to about 0.013 wt. percent, the selenium comprises from about 0.002 wt. percent to about 0.02 wt. percent, or the water comprises from about 96 wt. percent to about 98.5 of the injectable composition based on a total weight of the injectable composition.

In many cases, in the trace elements injectable composition prepared by the above method, the zinc is sourced from zinc sulfate heptahydrate at a dose of from about 2.5 to about 7 mg/day, the copper is sourced form cupric sulfate pentahydrate at a dose of from about 0.5 to about 1.5 mg/day, the manganese is sourced from manganese sulfate monohydrate at a dose of from about 0.15 to about 0.8 mg/day, and the selenium is sourced from selenious acid at a dose of from about 20 to about 60 µg/day. In some other embodiments, the method of preparing the trace elements composition of this disclosure provides an injectable composition where the zinc is zinc sulfate heptahydrate at a dose of from about 2.5 to about 7 mg/day, the copper is cupric sulfate pentahydrate at a dose of from about 0.5 to about 1.5 mg/day, the manganese is manganese sulfate monohydrate at a dose of from about 0.015 to about 0.08 mg/day, and the selenium is sourced selenious acid at a dose of from about 20 to about 60 µg/day. In some embodiments, selenious acid, is a weak acid and it can form salts with metal oxides and hydroxides, such as potassium, zinc, copper, manganese, calcium, or molybdenum. It can also form salts with ammonia (e.g., ammonium selenite) and organic bases.

In many instances the pH of the trace elements composition varies in a range from about 1.0 to about 9. In some instances, the pH of the trace elements composition can be about 1.0, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9 to about 9.0.

In some embodiments, the pH of the trace elements composition can be adjusted using pH adjusting agents including organic or inorganic acids and bases. Suitable acids include, but are not limited to, inorganic acids such as hydrochloric acid, hydrobromic acid, sulfuric acid, nitric acid, phosphoric acid or the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid or the like. Suitable inorganic bases include, but are not limited to, sodium hydroxide, potassium hydroxide, K2CO3, Na2CO3, K3PO4, Na3PO4, K2HPO4, Na2HPO4, organic bases include salts of primary, secondary, and tertiary amines, substituted amines including naturally occurring substituted amines, cyclic amines, ethanolamine, 2-diethylaminoethanol, lysine, arginine, histidine or the like.

In various embodiments, gamma radiation is used in the terminal sterilization step, which involves utilizing ionizing energy from gamma rays that penetrate deeply into a vial containing the injectable composition of this disclosure. Gamma rays are highly effective in killing microorganisms, they leave no residues, nor do they have sufficient energy to impart radioactivity to the apparatus. Gamma rays can be employed when the injectable composition is a vial or ampule because gamma ray sterilization does not require high pressures or vacuum conditions, and thus the container of the injectable composition is not stressed.

In other embodiments, electron beam (e-beam) radiation may be used to sterilize the injectable composition described in this disclosure. E-beam radiation comprises a form of ionizing energy, which is generally characterized by low penetration and high-dose rates. E-beam irradiation is similar to gamma ray processing in that it alters various chemical and molecular bonds on contact, including the reproductive cells of microorganisms. Beams produced for e-beam sterilization are concentrated, highly charged streams of electrons generated by the acceleration and conversion of electricity.

Autoclaving is usually performed in an autoclave. An autoclave uses pressurized steam as their sterilization agent. The basic concept of an autoclave is to have each item sterilized—whether it is a liquid, plastic ware, or glassware—come in direct contact with steam at a specific temperature and pressure for a specific amount of time. Time, steam, temperature, and pressure are the four main parameters required for a successful sterilization using an autoclave.

The amount of time and temperature required for sterilization of a vial or ampule containing the injectable composition can use higher temperatures for sterilization and requires shorter times. The most common temperatures used are 121° C. and 132° C. In order for steam to reach these high temperatures, steam has to be pumped into the chamber at a pressure higher than normal atmospheric pressure. In various embodiments, a terminal sterilization feasibility study confirmed that the finished product is stable and can maintain its characteristics upon terminal sterilization. Thus, in various embodiments, the trace elements injectable compositions of this application are terminally sterilized at 122.2° C. for 15 minutes.

The injectable compositions of the present disclosure are packaged in pharmaceutically acceptable containers. Pharmaceutically acceptable containers include intravenous bags, bottles, vials, and/or syringes. In certain embodiments, the containers include intravenous bags and syringes, which can be polymer-based, and vials and intravenous bottles, which can be made of glass. In some embodiments, the components of the container that come into contact with the pharmaceutical composition do not contain polyvinylchloride (PVC). In various aspects, the container is an intravenous bag that does not have any PVC containing components in contact with the pharmaceutical composition. It is also desirable to protect the pharmaceutical compositions from light. Therefore, the container may, optionally, further comprise a light barrier. In certain embodiments, the light barrier can be an aluminum over a pouch.

In many aspects, the present disclosure also provides methods for preparing sterile pharmaceutical compositions. Examples of suitable procedures for producing sterile pharmaceutical drug products include, but are not limited to, terminal moist heat sterilization, ethylene oxide, radiation (i.e., gamma and electron beam), and aseptic processing techniques. Any one of these sterilization procedures can be used to produce the sterile pharmaceutical compositions described herein.

Sterile pharmaceutical compositions may also be prepared using aseptic processing techniques. Sterility is maintained by using sterile materials and a controlled working environment. All containers and apparatus are sterilized, preferably by heat sterilization, prior to filling. Then, the container is filled under aseptic conditions, such as by passing the composition through a filter and filling the units. Therefore, the compositions can be sterile filled into a container to avoid the heat stress of terminal sterilization.

Method of Preparing Parenteral Nutrition

The trace elements of the current application include lower daily amounts of at least one of zinc, copper, chromium and/or manganese per 1 mL of the composition than currently available products.

In some embodiments, the trace elements composition contains little or no chromium. The chromium that is present can be present as an impurity and not to exceed about 1 µg and, in other aspects, not to exceed 0.5 µg, in other embodiments, not to exceed about 0.25 µg/mL, and in other embodiments, not to exceed 0.1 µg/mL. In other instances, the injectable composition contains from about 0.0001 µg/mL to about 0.25 µg/mL of chromium. Therefore, when the trace element is added to the PN (e.g., PN of one liter or more), the PN will have no added chromium but may, in some embodiments, contain a chromium impurity from about 0.0001 µg/mL to about 0.25 µg/mL, or in some embodiments, no chromium.

In some embodiments, the amount of chromium in the parenteral nutrition containing the trace elements composition or the trace elements composition itself is not more than about 0.15 µg/mL to not more than about 0.07 µg/mL or lower. With the not more than about 0.15 µg/mL of chromium, the maximum potential exposure to chromium (e.g., 0.045 µg/kg/day) will be 22.5% of the maximum chromium dose that can be used for parenteral nutrition in a target patient population (e.g., children (weighing 0.4-9.9 kg)). This can be based on a target dose volume of, for example, 0.3 mL/kg/day. In some embodiments, this will reduce the risk of toxicity from total chromium exposure in the parenteral nutrition (e.g., from intentionally added chromium and chromium as an impurity).

The trace elements in solution form can be added to the parenteral nutrition typically at a port of the parenteral nutrition container using aseptic technique and, optionally, under a laminar flow hood. The parenteral nutrition can have essential and non-essential amino acids, dextrose, water, lipids, and/or electrolytes in it.

In many embodiments, a method of making a parenteral nutrition containing trace elements is provided. The method comprises adding trace elements to the parenteral nutrition, the trace elements comprising about 900 µg to about 4,000 µg of zinc, about 40 µg to about 400 µg of copper, about 4 µg to about 90 µg of selenium, and about 1 µg to about 80 µg of manganese per 250 mL to about 4000 mL of the parenteral nutrition, the parenteral nutrition comprising at least one of amino acid, a dextrose, a lipid, an electrolyte, or a mixture thereof. In some cases, the parenteral nutrition obtained by this method contains 3,000 µg of zinc, 300 µg of copper, 60 µg of selenium, and 55 µg of manganese per 250 mL to about 4000 mL of the parenteral nutrition. In other cases, the parenteral nutrition obtained by this method contains 1000 µg of zinc, 60 µg of copper, 6 µg of selenium, and 3 µg of manganese per 1 mL of the injectable composition per 250 mL to about 4000 mL of the parenteral nutrition.

In yet other cases, in the parenteral nutrition the zinc comprises zinc sulfate or zinc sulfate heptahydrate in an amount of about 13.1 mg to about 13.3 mg, the copper comprises cupric sulfate or cupric sulfate pentahydrate in an amount of about 1.1 mg to about 1.2 mg, the manganese comprises manganese sulfate or manganese sulfate monohydrate in an amount of about 0.16 mg to about 0.18 mg and the selenium comprises selenious acid in an amount of about 95 µg to about 99 µg per about 250 mL to 4000 mL of parenteral nutrition. In another embodiment, the parenteral nutrition obtained by this method comprises zinc sulfate or zinc sulfate heptahydrate in an amount of about 13.2 mg, cupric sulfate or cupric sulfate pentahydrate of the parenteral nutrition in an amount of from about 1.179 mg, manganese sulfate or manganese sulfate monohydrate in an amount of about 0.0169 mg and the selenious acid is in an amount of about 98 µg per 250 mL to 4000 mL of parenteral nutrition.

In some embodiment, there is a method of making a parenteral nutrition containing trace elements at least one of (i) the amino acid comprises lysine hydrochloride, phenylalanine, leucine, valine, threonine, methionine, isoleucine, tryptophan, alanine, arginine, glycine, proline, histidine, glutamic acid, serine, aspartic acid, tyrosine or a mixture thereof; (ii) the dextrose comprises dextrose monohydrate; (iii) the lipid comprises soybean oil, phospholipid, glycerin or a mixture thereof; or (iv) the electrolyte comprises sodium acetate trihydrate, potassium chloride, sodium chloride, potassium acetate, sodium glycerophosphate anhydrous, magnesium sulfate heptahydrate, calcium chloride dihydrate, calcium gluconate or a mixture thereof. In the parenteral nutrition provided by this method, the dextrose comprises dextrose 5%, dextrose 10%, dextrose 20%, dextrose 25%, or dextrose 50% in water.

The parenteral nutrition provided by this method is stable when stored from about 2° C. to about 8° C. for up to about 14 days. In many instances, when stored from about 2° C. to about 8° C. for about 14 days, the parenteral nutrition maintained a pH from about 5.50 to about 5.90 and, in some cases, a pH from about 4.5 to about 7.

In some embodiments, the 14 days stability is measured from the time when the trace elements composition is added at room temperature to the parenteral nutrition. In some embodiments, the 14 days stability is measured from the time when the trace elements composition is added at room temperature to the parenteral nutrition and then stored under refrigeration at 2° C. to about 8° C. In some embodiments, the 14 days stability is measured from the time when the trace elements composition is added at room temperature to the parenteral nutrition and about to be administered to the patient, but is not and then is stored under refrigeration at 2° C. to about 8° C. for the 14 days.

Further, when stored from about 2° C. to about 8° C. for about 14 days, the parenteral nutrition comprises at least one of (i) no more than 12 particle per mL that are greater than 10 µm; or (ii) no more than 2 particle per mL that are greater than 25 µm. In other cases, when stored from about 2° C. to about 8° C. for about 14 days, the parenteral nutrition did not exhibit microbial growth when in contact with bacteria such as *S. aureus, P. aeruginosa, E. coli, C. albicans, A. brasiliensis* or a mixture thereof.

Method of Use of the Injectable Compositions

After addition of the trace elements to the parenteral nutrition, the parenteral nutrition can then be connected to an IV tube set and the parenteral nutrition administered via infusion over the desired period of time to the patient (e.g., 24 hours).

The parenteral nutrition can be used to provide a source of calories, protein, electrolytes, or essential fatty acids for adult patients requiring parenteral nutrition. In some embodiments, the method of the present application includes administering to a patient in need thereof an injectable parenteral nutrition formulation comprising at least one of amino acid, a dextrose, a lipid, an electrolyte, or a mixture thereof. Therefore, one or more trace elements (e.g., zinc, copper, selenium, manganese) can be added to injectable amino acids, dextrose, water, lipids, electrolytes, or a combination thereof based on the specific need of the patient.

The trace elements can be a single trace element (e.g., zinc alone) or a combination of trace elements (e.g., zinc, copper, selenium, manganese) that can be added to the injectable amino acids, dextrose, water, lipids, electrolytes or a combination thereof based on the specific need of the patient.

In various other embodiments, the parenteral nutrition comprises from about 900 µg to about 4,000 µg of zinc, from about 40 µg to about 400 µg of copper, from about 4 µg to about 90 µg of selenium, and from about 1 µg to about 80 µg of manganese per 250 mL to 4000 mL of the parenteral nutrition. In some aspects, the parenteral nutrition comprises, consists essentially of, or consists of 3,000 µg of zinc, 300 µg of copper, 60 µg of selenium, and 55 µg of manganese per 250 mL to about 4000 mL of the parenteral nutrition. In some aspects, the parenteral nutrition comprises, consists essentially of, or consists of 1,000 µg of zinc, 60 µg of copper, 6 µg of selenium, and 3 µg of manganese per 250 mL to about 4000 mL of the parenteral nutrition.

In other aspects, the zinc comprises zinc sulfate or zinc sulfate heptahydrate in an amount of about 13.1 mg to about 13.3 mg, the copper comprises cupric sulfate or cupric sulfate pentahydrate in an amount of about 1.1 mg to about 1.2 mg, the manganese comprises manganese sulfate or manganese sulfate monohydrate in an amount of about 0.16 mg to about 0.18 mg and the selenium comprises selenious acid in an amount of about 95 µg to about 99 µg per about 250 mL to 4000 mL of parenteral nutrition. In yet other aspects, the zinc sulfate or zinc sulfate heptahydrate is in an amount of about 13.2 mg, the cupric sulfate or the cupric sulfate pentahydrate is in an amount of about 1.179 mg, the manganese sulfate or manganese sulfate monohydrate is in an amount of about 0.169 mg and the selenious acid is in an amount of about 98 µg.

In many embodiments, the at least one of the amino acid useful in the method of providing a source of calories comprises lysine hydrochloride, phenylalanine, leucine, valine, threonine, methionine, isoleucine, tryptophan, alanine, arginine, glycine, proline, histidine, glutamic acid, serine, aspartic acid, tyrosine or a mixture thereof. The dextrose useful in this method includes dextrose monohydrate, anhydrous and hydrous forms of dextrose, for example, dextrose 5%, dextrose 10%, dextrose 20%, dextrose 25%, or dextrose 50% in water. or a combination thereof. Useful lipids include without limitation soybean oil, phospholipid, glycerin, or a mixture thereof. The electrolyte can comprise sodium acetate trihydrate, potassium chloride, sodium chloride, potassium acetate, sodium glycerophosphate anhydrous, magnesium sulfate heptahydrate, calcium chloride dihydrate, calcium gluconate or a mixture thereof.

In various aspects, the parenteral nutrition used in the method of providing a source of calories, protein, electrolytes, or essential fatty acids is nonpyrogenic and can have a pH that can vary from about 3.5 to about 7.9.

It has been surprisingly found that the parenteral nutrition used in the method of providing a source of calories, protein, electrolytes, or essential fatty acids is stable when stored from about 2° C. to about 8° C. for up to about 14 days. In many aspects, the stable parenteral nutrition when stored from about 2° C. to about 8° C. for about 14 days can maintain a pH from about 5.50, 5.60, 5.70, 5.80 to about 5.90. In various instances, when stored from about 2° C. to about 8° C. for about 14 days, the parenteral nutrition comprises at least one of (i) no more than 12 particle per mL that are greater than 10 µm; or (ii) no more than 2 particle per mL that are greater than 25 µm. Also, when stored at from about 2° C. to about 8° C. for about 14 days, the parenteral nutrition did not exhibit microbial growth caused by such microbes as, for example, *S. aureus, P. aeruginosa, E. coli, C. albicans, A. brasiliensis* or a mixture thereof.

In various embodiments, a method of maintaining plasma trace elements in a patient in need thereof is provided. The method of maintaining plasma trace elements comprises administering at least an injectable composition to the patient, the injectable composition comprising water, from about 900 µg to about 4,000 µg of zinc, from about 40 µg to about 400 µg of copper, from about 4 µg to about 90 µg of selenium, and from about 1 µg to about 80 µg of manganese per 1 mL of the injectable composition. In many aspects, when the injectable composition is stored from about 2° C. to about 8° C. for about 14 days, then the injectable composition comprises at least one of (i) no more than 12 particle per mL that are greater than 10 μm; or (ii) no more than 2 particle per mL that are greater than 25 μm. In other aspects, when stored from about 2° C. to about 8° C. for about 14 days, the injectable composition did not exhibit microbial growth caused by any one of several microbes, for example, S. aureus, P. aeruginosa, E. coli, C. albicans, A. brasiliensis or a mixture thereof. In many cases, when stored from about 2° C. to about 8° C. for about 14 days, the injectable composition maintained a pH from about 5.50 to about 5.90.

In various embodiments, the method of maintaining plasma trace elements in a patient in need thereof further comprises treating patients having a negative nitrogen balance. In other embodiments, the method of maintaining plasma trace elements in a patient in need thereof further comprises the use of the electrolyte as a supplement to intravenous solutions given for parenteral nutrition to maintain plasma levels of anyone of zinc, copper, manganese or selenium or a mixture thereof to prevent depletion of endogenous stores of these trace elements and subsequent deficiency symptoms.

These and other aspects of the present application will be further appreciated upon consideration of the following examples, which are intended to illustrate certain particular embodiments of the application, but they are not intended to limit its scope, as defined by the claims.

EXAMPLES

Examples of the stable, ready-to-use injectable compositions containing trace elements such as zinc, copper, selenium, and manganese are described in some of the examples below. The examples also include parenteral nutrition solutions with or without the stable injectable compositions having trace elements such as zinc, copper, selenium, and manganese. The trace elements of the current application include lower daily amounts of at least one of zinc, copper, chromium, and/or manganese per 1 mL of the trace element solution than currently available products. When added to parenteral solution the parenteral solution containing the trace elements remained stable for about at least 3 days up to 14 days under refrigeration.

Example 1

In this example, an injectable sterile, nonpyrogenic solution including trace elements of zinc, copper, manganese, and selenium is prepared by mixing these elements with water for injection to form 1 mL of injectable composition per single dose vial. This composition contains not more than 1.0 μg chromium in conformance with USP formulation requirements. The formulation is summarized in Table 6.

TABLE 6

Injectable Composition

| Ingredient Name | Quantity per mL | Elemental Equivalent |
|---|---|---|
| Zinc Sulfate•7H$_2$O, USP | 13.20 mg | 3 mg Zn/mL |
| Cupric Sulfate•5H$_2$O, USP | 1.18 mg | 0.3 mg Cu/mL |
| Manganese Sulfate•H$_2$O, USP | 169.00 mcg | 55 μg Mn/mL |
| Selenious Acid, USP | 98.00 mcg | 60 μg Se/mL |
| Sulfuric Acid, NF | N/A | N/A |
| Water for Injection, USP | Q.S. to 1 mL | N/A |

N/A = Not Applicable

Each mL contains: zinc sulfate, USP (heptahydrate) 13.20 mg (equivalent to 3 mg zinc); cupric sulfate, USP (pentahydrate) 1.18 mg (equivalent to 0.3 mg copper); selenious acid, USP 98 μg (equivalent to 60 μg selenium); manganese sulfate, USP (monohydrate) 169 μg (equivalent to 55 μg manganese); and water for injection, USP q.s. The pH range of the solution is 1.5 to 3.5 and may be adjusted with sulfuric acid, NF.

Example 2

This example discusses studies of known parenteral nutrition admixed with the injectable compositions of trace elements described in this application. Studies of parenteral nutrition (PN) solutions admixed with the injectable compositions of trace elements of this application were conducted over a 3 day and 14-day interval. PN solutions used in these studies were CLINIMIX® and KABIVEN® as listed in Table 7 below.

TABLE 7

| | | Parenteral Nutrition | | |
|---|---|---|---|---|
| Type | Ingredient | CLINIMIX E 4.25/25 | CLINIMIX E 4.25/10 | KABIVEN ® |
| | Soybean Oil (g/100 mL) | — | — | 3.9 |
| | Dextrose Hydrous, USP (g/100 mL) | 25 | 10 | 9.8 |
| | Amino Acids (g/100 mL) | 4.25 | 4.25 | 3.31 |
| | Total Nitrogen (mg/100 mL) | 702 | 702 | 526 |
| Essential Amino Acids | Leucine | 311 | 311 | 263 |
| | Isoleucine | 255 | 255 | 164 |
| | Leucine | — | — | 231 |
| | Valine | 247 | 247 | 213 |
| | Lysine (as the hydrochloride) | 247 | 247 | 263 |
| | Phenylalanine | 238 | 238 | 231 |
| | Histidine | 204 | 204 | 199 |
| | Threonine | 179 | 179 | 164 |
| | Methionine | 170 | 170 | 164 |
| | Tryptophan | 77 | 77 | 55 |
| Nonessential Amino Acids (mg/100 mL) | Alanine | 880 | 880 | 467 |
| | Arginine | 489 | 489 | 330 |
| | Glycine | 438 | 438 | 231 |
| | Proline | 289 | 289 | 199 |
| | Serine | 213 | 213 | 131 |
| | Aspartic Acid, USP | — | — | 99 |
| | Tyrosine | 17 | 17 | 6.7 |

TABLE 7-continued

Parenteral Nutrition

| Type | Ingredient | CLINIMIX E 4.25/25 | CLINIMIX E 4.25/10 | KABIVEN ® |
|---|---|---|---|---|
| Electrolytes (mg/100 ml) | Sodium Acetate Trihydrate, USP | 297 | 297 | 239 |
| | Potassium Chloride | — | — | 174 |
| | Sodium Glycerophosphate, Anhydrous | — | — | 147 |
| | Dibasic Potassium Phosphate, USP | 261 | 261 | — |
| | Sodium Chloride, USP | 77 | 77 | — |
| | Magnesium chloride, USP | 51 | 51 | — |
| | Magnesium Sulfate Heptahydrate, USP | — | — | 96 |
| | Calcium Chloride Dihydrate, USP | 33 | 33 | 29 |
| Electrolyte Profile (mEq/L) | Sodium | 35 | 35 | 31 |
| | Potassium | 30 | 30 | 23 |
| | Magnesium | 5 | 5 | 7.8 |
| | Calcium | 4.5 (2.2 mmol/L) | 4.5 (2.2 mmol/L) | 3.8 (1.9 mmol/L) |
| | Acetate | 70 | 70 | 38 |
| | Chloride | 39 | 39 | 45 |
| | Sulfate | — | — | 7.8 |
| | Phosphate (as HPO$_4$) | 30 (15 mmol/L) | 30 (15 mmol/L) | N.A. (9.7 mmol/L) |
| | pH range | 6.0 (4.5 to 7.0) | 6.0 (4.5 to 7.0) | 5.6 |
| | Osmolarity (mOsmol/L) (calc.) | 1825 | 1070 | 1060 |
| | From Dextrose | 850 | 340 | 330 |
| | From Lipid | — | — | 390 |
| | From Amino Acids | 170 | 170 | 130 |
| | Total (Dextrose, Lipid and Amino Acids) | 1020 | 510 | 1060 |

CLINIMIX E 4.25/25 contained 24% dextrose concentration and was used in a three (3)-day study. Because this formulation was discontinued, CLINIMIX E 4.25/10 which contained 10% dextrose concentration was used in the 14-day study. The same KABIVEN® formulation described in Table 2 was used in both 3-day and 14-day studies.

In these studies, 1 mL of the injectable trace element composition was added to two (2) L IV PN infusion bags of KABIVEN® and CLINIMIX E. KABIVEN® admixtures with and without 1 mL of Injectable trace element composition were stored for about at least 3 days (72 hours) at 2-8° C. Upon testing as described below the KABIVEN® admixtures met the acceptance criteria of a "no growth" protocol. CLINIMIX E admixtures with and without the introduction of Injectable trace element composition found the admixtures stored for about at least 3 days (72 hours) at either 2° C. to 8° C. or 20° C. to 25° C. met the acceptance criteria of "no growth" protocol. Based on the results of these admixture studies, we concluded that the admixture of injectable trace element composition in 2 L infusion PN solutions of KABIVEN® and CLINIMIX E supported the manufacturers' original package insert labeling recommendations for KABIVEN® and CLINIMIX E.

For example, for KABIVEN®, the labeling recommendation states that "KABIVEN® should be used immediately after mixing and the introduction of additives. If not used immediately, the storage time and conditions prior to use should not be longer than 24 hours at 2° to 8° C. (36° to 46° F.). After removal from storage at 2° to 8° C. (36° to 46° F.), the admixture should be infused within 24 hours. Any mixture remaining must be discarded."

For CLINIMIX E the labeling recommendations caution "Use promptly after mixing. Any storage with additives should be under refrigeration and limited to a period, no longer than 24 hours. After removal from refrigeration, use promptly and complete the infusion within 24 hours. Any mixture remaining must be discarded."

In order to establish stability data for parenteral nutrition admixed with the injectable compositions of trace elements, we conducted a stability study of injectable trace element composition (trace elements injectable composition, USP) in parenteral nutrition admixtures (assay test); a pH study of parenteral nutrition (PN) admixtures upon addition of injectable trace element composition (trace elements injectable composition, USP); a compatibility study of injectable trace element composition (trace elements injectable composition, USP) in parenteral nutrition admixtures; and a reduced inoculation antimicrobial effectiveness study for injectable trace element composition (trace elements injectable composition, USP) in parenteral nutrition admixtures.

These studies were intended to support the USP <797> medium risk storage for up to 9 days under refrigeration [2° to 8° C. (36° to 46° F.)]. At the time of initiating the 14-day admixture studies, it was noted that the current package insert (PI) labeling of KABIVEN® and CLINIMIX now includes the following beyond use dating (BUD) statements for storage:

For KABIVEN®: In the absence of additives, once activated, KABIVEN® remains stable for 48 hours at 25° C. (77° F.). If not used immediately, the activated bag can be stored for up to 7 days under refrigeration [2° to 8° C. (36° to 46° F.)]. After removal from refrigeration, the activated bag should be used within 48 hours. For CLINIMIX E: Storage after removal of overwrap: once removed from the protective clear overwrap, mixed (peel seal activated) or unmixed (peel seal intact), CLINIMIX E solutions may be stored under refrigeration for up to 9 days. The results or our studies are discussed in examples 3, below.

Example 3—Stability Study of Injectable Trace Element Composition (Trace Elements Injectable Composition, USP) in Parenteral Nutrition Admixtures Assay Test In this example, we evaluated whether the addition of an injectable trace element composition to parenteral nutrition (PN) admixtures would result in chemical degradation of individual ingredients under the prescribed in-use condition of up to 14 days. The PN admixtures were assay tested for zinc, copper, selenium, and manganese. Chromium was evaluated as a potential elemental impurity.

In this example, control PN admixtures (e.g., without an injectable trace element composition) of KABIVEN® and CLINIMIX E were tested for trace element levels of zinc, copper, selenium, manganese, and chromium and the findings are summarized in Tables 8 and 10 below. Tables 9 and 11 illustrate assay results of a KABIVEN® and CLINIMIX E PN IV solutions treated with the injectable trace element composition of this application and stored 14 days at 2° C. to 8° C.

TABLE 8

Assay Results for KABIVEN ® Control Admixtures without Injectable Trace Element Composition

| Assay | Zinc | Copper | Selenium | Manganese | Chromium |
|---|---|---|---|---|---|
| Results | <750 µg/L | <75 µg/L | <15 µg/L< | <13.7 µg/L | <0.25 µg/mL |

TABLE 9

Assay Results for Injectable Trace Element Composition in KABIVEN ® Solution Stored 14 days at 2° C. to 8° C.

| Assay | Acceptance Criteria | Day 0 | Day 5 | Day 7 | Day 10 | Day 14 |
|---|---|---|---|---|---|---|
| Zinc | 90.0-110.0% | 96.5 | 93.9 | 93.8 | 97.0 | 96.0 |
| Copper | 90.0-110.0% | 101.8 | 98.7 | 97.8 | 99.9 | 105.5 |
| Selenium | 90.0-110.0% | 92.6 | 93.5 | 97.9 | 92.6 | 90.8 |
| Manganese | 90.0-110.0% | 100.7 | 95.0 | 92.1 | 102.5 | 97.9 |

TABLE 10

Assay Results for CLINIMIX E Control PN Admixture without Injectable Trace Element Composition

| Assay | Zinc | Copper | Selenium | Manganese | Chromium |
|---|---|---|---|---|---|
| Results | <750 µg/L | <75 µg/L | <15 µg/L | <13.7 µg/L | <0.25 µg/mL |

TABLE 11

Assay Results for Injectable trace element composition in CLINIMIX Solution Stored for 14 days at 2° C. to 8° C.

| Assay | Acceptance Criteria | Day 0 | Day 5 | Day 7 | Day 10 | Day 14 |
|---|---|---|---|---|---|---|
| Zinc | 90.0-110.0% | 98.5 | 94.4 | 96.5 | 96.2 | 96.3 |
| Copper | 90.0-110.0% | 109.7 | 98.8 | 101.5 | 101.0 | 106.0 |
| Selenium | 90.0-110.0% | 108.8 | 102.0 | 104.2 | 101.2 | 95.7 |
| Manganese | 90.0-110.0% | 105.0 | 97.2 | 98.9 | 101.6 | 106.8 |

The results of this study show that assay values of parenteral nutrition solutions of KABIVEN® and CLINIMIX E in two (2) L infusion solutions each spiked with 1.0 mL of injectable trace element composition and stored under refrigeration (2° C. to 8° C.) remained within the protocol acceptance criteria of 90.0-110.0% acceptance criteria for the fourteen (14) day duration of the study.

Example 4—pH Study of Parenteral Nutrition (PN) Admixtures Upon Addition of Injectable Trace Element Composition (Trace Elements Injectable Composition)

In this example, a study was conducted to evaluate pH changes before and after the addition of injectable trace element composition added to PN solutions of KABIVEN® and CLINIMIX E. The study was conducted to determine if the addition of the injectable trace element composition of this disclosure would significantly change the pH of the PN admixtures under the prescribed in-use conditions. The pH measurements were performed at Day 0, Day 5, Day 7, Day 10 and Day 14 on samples stored at 2° C. to 8° C. and the results are illustrated in Tables 12 and 13. In the assays summarized in Tables 9 and 10, the control sample is either KABIVEN® or CLINIMIX E PN mixture as found in an IV bag or TE-4 represents a bag of KABIVEN® or CLINIMIX E to which 1.0 mL of injectable trace element composition containing zinc, copper, selenium, and manganese was added.

TABLE 12 pH Results for Injectable Trace Element Composition added to KABIVEN ® Solution Stored 14 days at 2° C. to 8° C.

| Test | Acceptance Criteria | Day 0 Control | Day 0 TE-4 | Day 5 Control | Day 5 TE-4 | Day 7 Control | Day 7 TE-4 | Day 10 Control | Day 10 TE-4 | Day 14 Control | Day 14 TE-4 |
|---|---|---|---|---|---|---|---|---|---|---|---|
| pH | Record results | 5.52 | 5.51 | 5.51 | 5.51 | 5.49 | 5.50 | 5.50 | 5.49 | 5.50 | 5.50 |

Control = bag of KABIVEN ®
TE-4 = bag of KABIVEN ® with added 1.0 mL of injectable trace element composition including Zn, Cu, Mn, and Se.

TABLE 13 pH Results for Injectable trace element composition added to CLINIMIX Solution Stored 14 days at 2° C. to 8° C.

| Test | Acceptance Criteria | Day 0 Control | Day 0 TE-4 | Day 5 Control | Day 5 TE-4 | Day 7 Control | Day 7 TE-4 | Day 10 Control | Day 10 TE-4 | Day 14 Control | Day 14 TE-4 |
|---|---|---|---|---|---|---|---|---|---|---|---|
| pH | Record results | 5.86 | 5.87 | 5.85 | 5.85 | 5.86 | 5.85 | 5.86 | 5.86 | 5.87 | 5.86 |

Control = bag of CLINIMIX
TE-4 = bag of CLINIMIX with added 1.0 mL of Injectable trace element composition including Zn, Cu, Mn, and Se.

The results of these studies illustrate that pH of KABIVEN® and CLINIMIX E PN solutions, each spiked with 1.0 mL of Injectable trace element composition did not differ from the pH of their respective control samples. In addition, the pH of KABIVEN® control, CLINIMIX E and samples spiked with injectable trace element composition was unchanged after storage under refrigeration from 2° C. to 8° C. for up to 14 days.

Based on the results of these studies, it can be concluded that the addition of 1.0 mL of injectable trace element composition to the 2 L solution of KABIVEN® and/or CLINIMIX E will not alter the pH of the PN solutions when stored for 14 days at refrigeration (2° C. to 8° C.).

Example 5—Compatibility Study of Injectable Trace Element Composition (Trace Elements Injectable Composition, USP) in Parenteral Nutrition Admixtures The studies summarized in Tables 14, 15, 16 and 17 were initiated to assure that the injectable trace element composition of this disclosure and PN solutions of KABIVEN and CLINIMIX E are physically compatible. The PN admixtures with and without the injectable trace element composition were tested for visual examination and particulate matter (PM) by means of USP <788> Method 2 (Microscopic Particle Count Test). The testing was performed at Day 0, Day 5, Day 7, Day 10, and Day 14 on samples stored at 2-8° C.

TABLE 14

PM Results for Injectable trace element composition (TE-4) in KABIVEN ® Bags Stored 14 days at 2° C. to 8° C.

| Test | Acceptance Criteria | 0 days Control | 0 days TE-4 | 5 days Control | 5 days TE-4 | 7 Days Control | 7 Days TE-4 | 10 days Control | 10 days TE-4 | 14 Days Control | 14 Days TE-4 |
|---|---|---|---|---|---|---|---|---|---|---|---|
| Visual Examination | Precipitates have not formed during the addition of Injectable trace element composition | NA | Conforms | NA | Conforms | NA | Conforms | NA | Conforms | NA | Conforms |
| | The emulsion has not separated. | NA | Conforms | NA | Conforms | NA | Conforms | NA | Conforms | NA | Conforms |
| Particulate Matter <788>:Method 2 Microscopic Particle Count Test | NMT 12 particles per 1 mL that are ≥10 μm. | <1 | <1 | <1 | <1 | <1 | <1 | <1 | <1 | <1 | <1 |
| | NMT 2 particles per 1 mL that are ≥25 μm. | <1 | <1 | <1 | <1 | <1 | <1 | <1 | <1 | <1 | <1 |
| | 100 μm (for informational purposes only) | 0 | 0 | 0 | 0 | <1 | <1 | <1 | <1 | <1 | <1 |

Control = bag of KABIVEN ®
TE-4 = bag of KABIVEN ® with added 1.0 mL of injectable trace element composition including Zn, Cu, Mn, and Se.

TABLE 15

Particle Categorization for Injectable trace element composition in KABIVEN ® Bags Stored 14 days at 2° C. to 8° C.

| Test Station | Particle Description Control | TE-4 |
|---|---|---|
| 0 Days | Major: dark particles (10-50 μm) Minor: light particles (10-40 μm), polymeric (20-70 μm) ≥100 μm: no particles noted | Major: dark particles (10-40 μm) Minor: light particle (10-40 μm), polymeric (20-70 μm) ≥100 μm: no particles noted |
| 5 Days | Major: light particles (10-80 μm) Minor: dark particles (10-70 μm), polymeric (30-80 μm) ≥100 μm: no particles noted | Major: dark particles (10-70 μm) Minor: light particles (10-70 μm), polymeric (60 μm) ≥100 μm: no particles noted |
| 7 Days | Major: dark particles (10-40 μm) Minor: light particles (10-30 μm), polymeric (30->100 μm), fibrous (80 μm) ≥100 μm: polymeric (190 μm, 240 μm) | Major: dark particles (10-60 μm) Minor: light particles (10-40 μm), polymeric (30-50 μm) ≥100 μm: fibrous (310 μm) |
| 10 Days | Major: dark particles (10-40 μm) Minor: light particles (10-60 μm), polymeric (20->100 μm) ≥100 μm: fibrous (180 μm), polymeric (270 μm) | Major: dark particles (10-40 μm) Minor: light particles (10-50 μm), polymeric (20->100 μm) ≥100 μm: polymeric (200 μm) |
| 14 Days | Major: dark particles (10-80 μm) Minor: light particles (10-40 μm), polymeric (20->100 μm) ≥100 μm: polymeric (290 μm, 170 μm, 140 μm, 210, 250 μm, 200 μm) | Major: dark particles (10-70 μm) Minor: light particles (10-80 μm), polymeric (20-90 μm) ≥100 μm: no particles noted |

Control = bag of KABIVEN ®
TE-4 = bag of KABIVEN ® with added 1.0 mL of injectable trace element composition including Zn, Cu, Mn, and Se.

TABLE 17

Particle Categorization for Injectable trace element composition in CLINIMIX E Bags Stored 14 Days at 2° C. to 8° C.

| Test Station | Particle Description Control | TE-4 |
|---|---|---|
| 0 Days | Major: dark particles (10-60 μm) Minor: light particles (10-70 μm), polymeric (80 μm), fibrous (90 μm) ≥100 μm: no particles noted | Major: dark particles (10-90 μm) Minor: light particle (10-70 μm), polymeric (80 μm) ≥100 μm: fibrous (460 μm) |
| 5 Days | Major: dark particles (10-50 μm) Minor: light particles (10-40 μm), polymeric (20-70 μm) ≥100 μm: fibrous (380 μm) | Major: dark particles (10-90 μm) Minor: light particles (10-70 μm), polymeric (20 μm-60 μm) ≥100 μm: fibrous (150 μm, 170 μm, 260 μm) |
| 7 Days | Major: dark particles (10-80 μm) Minor: light particles (10-70 μm), polymeric (20-60 μm) ≥100 μm: no particles noted | Major: dark particles (10-80 μm) Minor: light particles (10-90 μm), polymeric (20-90 μm) ≥100 μm: no particles noted |
| 10 Days | Major: dark particles (10-80 μm) Minor: light particles (10-70 μm), polymeric (20-90 μm) ≥100 μm: no particles noted | Major: dark particles (10->100 μm) Minor: light particles (10-80 μm), polymeric (70 μm) ≥100 μm: dark particle (160 μm) |
| 14 Days | Major: dark particles (10-50 μm) Minor: light particles (10-90 μm), polymeric (20-90 μm), fibrous (30->100 μm) | Major: dark particles (10-50 μm) Minor: light particles (10-80 μm), polymeric (20-80 μm) ≥100 μm: no particles noted |

Control = bag of CINIMIX E
TE-4 = bag of CINIMIX E with added 1.0 mL of Injectable trace element composition including Zn, Cu, Mn, and Se.

The compatibility study results for both, the control and admixture samples illustrated in Tables 14, 15, 16 and 17 indicated that particulate matter in these samples remained

TABLE 16

Particulate Matter Results for Injectable Trace Element Composition in CLINIMIX E Bags Stored 14 Days at 2° C. to 8° C.

| Test | Acceptance Criteria | 0 days Control | 0 days TE-4 | 5 days Control | 5 days TE-4 | 7 Days Control | 7 Days TE-4 | 10 days Control | 10 days TE-4 | 14 Days Control | 14 Days TE-4 |
|---|---|---|---|---|---|---|---|---|---|---|---|
| Visual Examination | Precipitates have not formed during the addition of injectable trace element composition | NA | Conforms | NA | Conforms | NA | Conforms | NA | Conforms | NA | Conforms |
| | The emulsion has not separated. | NA | Conforms | NA | Conforms | NA | Conforms | NA | Conforms | NA | Conforms |
| Particulate Matter <788>:Method 2 Microscopic Particle Count Test | NMT 12 particles per 1 mL that are ≥10 μm. | <1 | <1 | <1 | <1 | <1 | 1 | 1 | 1 | <1 | <1 |
| | NMT 2 particles per 1 mL that are ≥25 μm. | <1 | <1 | <1 | <1 | <1 | <1 | <1 | <1 | <1 | <1 |
| | 100 μm (for informational purposes only) | 0 | <1 | <1 | <1 | 0 | 0 | 0 | <1 | <1 | 0 |

Control = bag of CINIMIX E ™
TE-4 = bag of CINIMIX E with added 1.0 mL of Injectable trace element composition including Zn, Cu, Mn, and Se.

within USP <788> limits for large volume parenteral solutions. In addition, the consistency of the particle counts and particle morphologies of the control and injectable trace element composition admixture samples, demonstrated no evidence of incompatibility.

Based on the results of this study, injectable trace element composition containing zinc, copper, selenium, and manganese of this application is compatible with KABIVEN® and CLINIMIX E solutions when stored for 14 days at refrigeration (2° C. to 8° C.).

Example 6—Reduced Inoculation Antimicrobial Effectiveness Study for Injectable Trace Element Composition (Trace Elements Injectable Composition, USP) in Parenteral Nutrition Admixtures In this example, the purpose of the reduced inoculation antimicrobial effectiveness study was to demonstrate whether or not there would be adventitious microbial contamination growth during the preparation and storage of parenteral nutrition admixtures with injectable trace element composition containing zinc, copper, selenium and manganese. The PN admixtures of Kobiven® and CLINIMIX E treated with injectable trace element composition were challenged with five appropriate compendial microorganisms (i.e., *Escherichia coli, Pseudomonas aeruginosa, Staphylococcus aureus, Candida albicans*, and *Aspergillus brasiliensis*) at low inoculum levels 10-100 colony forming units/mL (CFU) for up to 14 days at 2-8° C. storage conditions.

It is noted that the inoculum concentration of *Candida albicans* exceeded protocol upper limit of 100 CFU/mL (obtained 120 CFU/mL) had a reported Log CFU recovery of 2.1. There was no impact on the study as the Log CFU recoveries which were accurately enumerated at each time point of the study.

At each test point, the Log CFU recovery values were measured, were 10-100 CFU is equivalent to 1-2 Log CFU. The acceptance criteria of the protocol was "no growth" which was defined as not more than 0.5 log increases from the calculated inoculum concentration. The results in tables 18, 19, 20, 21, 22, 23, 24, and 25 are reported as Log CFU/mL of product.

TABLE 18

Log Recovery Values for KABIVEN ® Admixture Bags with Injectable Trace Element Composition (2° C. to 8° C.)

| Organism (ATCC) | Inoculated | Time 0 | Day 5 | Day 7 | Day 10 | Day 14 |
|---|---|---|---|---|---|---|
| S. aureus (6538) | 1.8 | 1.7 | 1.8 | 1.9 | 1.9 | 1.8 |
| P. aeruginosa (9027) | 1.6 | 1.8 | 0.9 | 0.8 | 0.5 | 0.5 |
| E. coli (8739) | 2.0 | 2.1 | 1.9 | 1.8 | 1.6 | 1.6 |
| C. albicans (10231) | 2.1[a] | 2.1 | 2.0 | 2.0 | 2.0 | 2.0 |
| A. brasiliensis (16404) | 1.4 | 1.5 | 1.4 | 1.2 | 1.2 | 1.2 |
| Negative Product (TSA) | N/A | <0.0 | <0.0 | <0.0 | <0.0 | <0.0 |
| Negative Product (SDA) | N/A | <0.0 | <0.0 | <0.0 | <0.0 | <0.0 |

[a]Inoculum concentration exceeded protocol limit of 100 CFU/mL (obtained 120 CFU/mL). There was no impact on the study.

TABLE 19

Log Reduction Values for KABIVEN ® Admixture Bags with Injectable Trace Element Composition (2° C. to 8° C.)

| Organism (ATCC) | Inoculated | Time 0 | Day 5 | Day 7 | Day 10 | Day 14 |
|---|---|---|---|---|---|---|
| S. aureus (6538) | 1.8 | −0.1 | 0.0 | +0.1 | +0.1 | 0.0 |
| P. aeruginosa (9027) | 1.6 | +0.2 | −0.7 | −0.8 | −1.1 | −1.1 |
| E. coli (8739) | 2.0 | +0.1 | −0.1 | −0.2 | −0.4 | −0.4 |
| C. albicans (10231) | 2.1[a] | 0.0 | −0.1 | −0.1 | −0.1 | −0.1 |
| A. brasiliensis (16404) | 1.4 | +0.1 | 0.0 | −0.2 | −0.2 | −0.2 |

[a]Inoculum concentration exceeded protocol limit of 100 CFU/mL (obtained 120 CFU/mL). There was no impact on the study.

TABLE 20

Log Recovery Values for KABIVEN ® Admixture Bags without Injectable trace element composition (2° C. to 8° C.)

| Organism (ATCC) | Inoculated | Time 0 | Day 5 | Day 7 | Day 10 | Day 14 |
|---|---|---|---|---|---|---|
| S. aureus (6538) | 1.8 | 2.0 | 1.8 | 1.9 | 2.0 | 1.8 |
| P. aeruginosa (9027) | 1.6 | 1.6 | 0.8 | 0.5 | 0.6 | 0.5 |
| E. coli (8739) | 2.0 | 2.1 | 1.9 | 1.9 | 1.9 | 1.6 |
| C. albicans (10231) | 2.1[a] | 2.0 | 2.0 | 2.0 | 2.1 | 2.1 |
| A. brasiliensis (16404) | 1.4 | 1.5 | 1.1 | 1.3 | 1.3 | 1.3 |

TABLE 20-continued

Log Recovery Values for KABIVEN ® Admixture Bags without Injectable trace element composition (2° C. to 8° C.)

| Organism (ATCC) | Inoculated | Time 0 | Day 5 | Day 7 | Day 10 | Day 14 |
|---|---|---|---|---|---|---|
| Negative Product (TSA) | N/A | <0.0 | <0.0 | <0.0 | <0.0 | <0.0 |
| Negative Product (SDA) | N/A | <0.0 | <0.0 | <0.0 | <0.0 | <0.0 |

[a]Inoculum concentration exceeded protocol limit of 100 CFU/mL (obtained 120 CFU/mL). There was no impact on the study.

TABLE 21

Log Reduction Values for KABIVEN ® Admixture Bags without Injectable Trace Element Composition (2° C. to 8° C.)

| Organism (ATCC) | Inoculated | Time 0 | Day 5 | Day 7 | Day 10 | Day 14 |
|---|---|---|---|---|---|---|
| S. aureus (6538) | 1.8 | +0.2 | 0.0 | +0.1 | +0.2 | 0.0 |
| P. aeruginosa (9027) | 1.6 | 0.0 | −0.8 | −1.1 | −1.0 | −1.1 |
| E. coli (8739) | 2.0 | +0.1 | −0.1 | −0.1 | −0.1 | −0.2 |
| C. albicans (10231) | 2.1[a] | −0.1 | −0.1 | −0.1 | −0.0 | 0.0 |
| A. brasiliensis (16404) | 1.4 | +0.1 | −0.3 | −0.1 | −0.1 | −0.1 |

[a]Inoculum concentration exceeded protocol limit of 100 CFU/mL (obtained 120 CFU/mL). There was no impact on the study.

KABIVEN® (contains dextrose, essential and nonessential amino acids with electrolyte and a 20% lipid emulsion) with and without injectable trace element composition containing zinc, copper, manganese and selenium were stored for up to 14 days at 2° C. to 8° C. met the protocol's acceptance criteria of "no growth." The marginally higher inoculum concentration of C. albicans did not enhance any microbial proliferation within the product.

TABLE 22

Log Recovery Values for CLINIMIX E Admixture Bags (contains essential and non-essential amino acids with electrolyte in dextrose with calcium) with Injectable trace element composition (2° C. to 8° C.)

| Organism (ATCC) | Inoculated | Time 0 | Day 5 | Day 7 | Day 10 | Day 14 |
|---|---|---|---|---|---|---|
| S. aureus (6538) | 1.8 | 1.9 | 1.8 | 1.8 | 1.8 | 1.7 |
| P. aeruginosa (9027) | 1.6 | 1.9 | 0.9 | 1.1 | 1.0 | 0.7 |
| E. coli (8739) | 2.0 | 2.0 | 1.6 | 1.4 | 1.2 | 1.0 |
| C. albicans (10231) | 2.1[a] | 2.0 | 2.0 | 2.0 | 1.9 | 1.9 |
| A. brasiliensis (16404) | 1.4 | 1.5 | 1.3 | 1.3 | 1.3 | 1.3 |
| Negative Product (TSA) | N/A | <0.0 | <0.0 | <0.0 | <0.0 | <0.0 |
| Negative Product (SDA) | N/A | <0.0 | <0.0 | <0.0 | <0.0 | <0.0 |

[a]Inoculum concentration exceeded protocol limit of 100 CFU/mL (obtained 120 CFU/mL). There was no impact on the study.

TABLE 23

Log Reduction Values for CLINIMIX E Admixture Bags with Injectable trace element composition (2° C. to 8° C.)

| Organism (ATCC) | Inoculated | Time 0 | Day 5 | Day 7 | Day 10 | Day 14 |
|---|---|---|---|---|---|---|
| S. aureus (6538) | 1.8 | +0.1 | 0.0 | 0.0 | 0.0 | −0.1 |
| P. aeruginosa (9027) | 1.6 | +0.3 | −0.7 | −0.5 | −0.6 | −0.9 |
| E. coli (8739) | 2.0 | 0.0 | −0.4 | −0.6 | −0.8 | −1.0 |
| C. albicans (10231) | 2.1[a] | −0.1 | −0.1 | −0.1 | −0.2 | −0.2 |
| A. brasiliensis (16404) | 1.4 | +0.1 | −0.1 | −0.1 | −0.1 | −0.1 |

[a]Inoculum concentration exceeded protocol limit of 100 CFU/mL (obtained 120 CFU/mL). There was no impact on the study.

TABLE 24

Log Recovery Values for CLINIMIX E Admixture Bags without Injectable
Trace Element Composition (2° C. to 8° C.)

| Organism (ATCC) | Inoculated | Time 0 | Day 5 | Day 7 | Day 10 | Day 14 |
|---|---|---|---|---|---|---|
| S. aureus (6538) | 1.8 | 2.1 | 1.9 | 1.8 | 1.8 | 1.7 |
| P. aeruginosa (9027) | 1.6 | 1.7 | 1.1 | 0.8 | 0.7 | 0.5 |
| E. coli (8739) | 2.0 | 2.0 | 1.6 | 1.5 | 1.3 | 1.0 |
| C. albicans (10231) | 2.1$^a$ | 2.0 | 1.9 | 1.9 | 1.9 | 1.9 |
| A. brasiliensis (16404) | 1.4 | 1.5 | 1.2 | 1.2 | 1.3 | 1.3 |
| Negative Product (TSA) | N/A | <0.0 | <0.0 | <0.0 | <0.0 | <0.0 |
| Negative Product (SDA) | N/A | <0.0 | <0.0 | <0.0 | <0.0 | <0.0 |

$^a$Inoculum concentration exceeded protocol limit of 100 CFU/mL (obtained 120 CFU/mL). There was no impact on the study.

TABLE 25

Log Reduction Values for CLINIMIX E Admixture Bags without Injectable
Trace Element Composition (2° C. to 8° C.)

| Organism (ATCC) | Inoculated | Time 0 | Day 5 | Day 7 | Day 10 | Day 14 |
|---|---|---|---|---|---|---|
| S. aureus (6538) | 1.8 | +0.3 | −0.1 | 0.0 | 0.0 | −0.1 |
| P. aeruginosa (9027) | 1.6 | +0.1 | −0.5 | −0.8 | −0.9 | −1.1 |
| E. coli (8739) | 2.0 | 0.0 | −0.4 | −0.5 | −0.7 | −1.0 |
| C. albicans (10231) | 2.1$^a$ | −0.1 | −0.2 | −0.2 | −0.2 | −0.2 |
| A. brasiliensis (16404) | 1.4 | +0.1 | −0.2 | −0.2 | −0.1 | −0.1 |

$^a$Inoculum concentration exceeded protocol limit of 100 CFU/mL (obtained 120 CFU/mL). There was no impact on the study.

The Log recovery values results of CLINIMIX E IV admixtures with and without injectable trace element composition containing zinc, copper, selenium and manganese found that admixtures stored for up to 14 days at 2° C. to 8° C. met the protocol's acceptance criteria of "no growth."

The results of the reduced inoculation AME study, found both KABIVEN® and CLINIMIX E admixtures with and without the introduction of injectable trace element composition and stored for up to 14 days under refrigeration (2° C. to 8° C.) met the protocol's acceptance criteria of "no growth."

Since the results of the four-admixture studies met our acceptance criteria, we concluded that the addition of injectable trace element composition to either 2 L infusion solution (KABIVEN® and/or CLINIMIX E) supports the manufacturers' current package insert (PI) labeling of both KABIVEN® and CLINIMIX E that the PN admixtures are stable for up to 9 days when kept under refrigeration. As a result, a package insert for the injectable trace element composition of this invention can include the following USP <797> medium-risk BUD statements for package insert for refrigerated storage up to 9 days.

Therefore, the package insert for injectable trace element composition has been revised to include the following storage recommendation: "Use parenteral nutrition solutions containing injectable trace element composition promptly after mixing. Any storage of the admixture should be under refrigeration from 2° C. to 8° C. (36° F. to 46° F.) and limited to a period, no longer than 9 days. After removal from refrigeration, use promptly and complete the infusion within 24 hours. Discard any remaining admixture." This package insert statement, in conjunction with our 14-day admixture studies at 2° to 8° C., now provide healthcare professionals, pharmacists and end-users extensive admixture stability information for selenious acid injection, USP, zinc sulfate injection, USP, and injectable trace element composition containing zinc, copper, manganese and selenium (Trace elements injectable composition, USP) in parenteral nutrition infusion solutions under refrigeration [2° to 8° C. (36° to 46° F.)].

Example 7—Process for Preparing Trace Elements Injectable Compositions

Three exhibit batches (lot RD15-013, RD16-001, RD16-007) and bridging batch (lot RD18-007) of the trace elements injectable composition, USP formulation were prepared utilizing the equipment and process parameters summarized in Table 26 below.

TABLE 26

Process Parameters for Injectable Composition

| Manufacturing Train and Process Parameters | |
|---|---|
| Concentration | Zinc: 3 mg/mL |
| | Copper: 0.3 mg/mL |
| | Selenium: 60 μg/mL |
| | Manganese: 55 μg/mL |
| Batch Size | 60 Liters |
| Formulation Vessel | T-8 |
| | Operating Volume of 30-100 L |
| | Fixed Speed Mixer: 290 rpm/minute |
| Mixing Time for Addition of APIs Zinc Sulfate•7H$_2$O, USP Cupric Sulfate•5H$_2$O, USP Manganese Sulfate•H$_2$O, USP Selenious Acid, USP to Initial Water for Injection Charge | NLT 10 minutes |
| Mixing Time for pH Adjustment(s) | NLT 10 minutes |
| Mixing Time (post initial Q.S.) | NLT 15 minutes |
| Mixing Time (post final Q.S.) | NLT 15 minutes |
| Bulk Holding Time | 48 hours |
| Pre-Filter | 10" Pall Profile II (Polypropylene filament) 1.0 micron (ID: AB1Y0107PH4) |

TABLE 26-continued

Process Parameters for Injectable Composition

Manufacturing Train
and Process Parameters

| | |
|---|---|
| Filling Line | 1 or 3 |
| Sterilizing Filter Type, Size, and Model Number | Pall Ultipor $N_{66}$ 0.2 Micron Filter, Size 4"ID: MCY4440NFPH4-4" |
| Number of Sterilizing Filters to Use | 1 |
| Filter Priming Volume | NLT 1.0 Liter |
| Receiving Vessel | 45 L Pyrex Glass Carboy |
| Container: USP Type I glass vial, Gerresheimer Gx33 | FV02T13G33 |
| Stopper: West 4432 FluroTec B2-40 | ST13WB4432FLRS |
| Fill Volume | 1 mL |

TABLE 26-continued

Process Parameters for Injectable Composition

Manufacturing Train
and Process Parameters

| | |
|---|---|
| Nitrogen Flush | No |
| Terminally Sterilized | Yes |
| Autoclave Cycle | 122.2° C. for 15 minutes |

NTL refers to not less than.

The compounding procedure described below was followed for a 60 L batch. A 50 L USP bulk tank (range 45-55 L) was charged with of water for injection (WFI). A mixer (Fixed Speed: 290 RPM) was turned on and the temperature was recorded. The mixer was turned off and specified amounts of USP Zinc Sulfate·7H$_2$O, Cupric Sulfate·5H$_2$O, Manganese Sulfate·H$_2$O and Selenious Acid were added into the bulk tank.

The bulk tank was closed and mixing continued for a minimum of 10 minutes (range 10 to 15 minutes) or until dissolved. At the completion of mixing, the mixer was stopped, the tank opened, and the bulk product was visually inspected to ensure complete dissolution. Approximately 50 mL of the bulk solution was taken and checked for pH at 25° C.±2° C. The target pH was 2.0 (range 1.9 to 2.1). If the pH of the bulk solution was not 2.0 (range 1.9 to 2.1), the pH was slowly adjusted with 10% v/v sulfuric acid solution to a target pH of 2.0 (range 1.9 to 2.1) and mixed for a minimum of 10 minutes (10 to 15 minutes) after each pH adjustment solution.

The mixer was turned off and the bulk solution Q.S. to 60 Liters with Water for Injection, USP. Tank was closed, and the bulk solution mixed for a minimum of 15 minutes (range 15 to 20 minutes).

Mixing was continued while cooling the bulk to 25° C.±2° C. Mixer was turned off, the tank opened and re-verified Q.S., otherwise more water for injection USP was added, if necessary. If additional WFI, USP was added, tank was closed, and bulk solution was mixed for a minimum of 15 minutes (typical range 15 to 20 minutes). If no additional water was added, tank was closed, and this step marked as N/A. At end of mixing, the bulk tank was opened, approximately 50 mL of the bulk solution collected, and the pH checked at 25° C.±2° C. Target pH was 2.0 (range 1.9 to 2.1). If the pH was not 2.0 (range 1.9 to 2.1) pH was slowly adjusted with 10% v/v sulfuric acid solution to a target pH of 2.0 (range 1.9 to 2.1). Bulk was mixed for a minimum of 10 minutes (10 to 15 minutes) after each pH adjustment solution.

Following the above compounding, in-process chemistry samples were taken and analyzed. The in-process results for the four exhibit batches are provided in Table 27:

TABLE 27

In-Process Results

| | | Results | | | |
|---|---|---|---|---|---|
| Test | Specifications | RD15-013 | RD16-001 | RD16-007 | RD18-007 |
| Specific Gravity | Report Result | 1.009 g/mL | 1.009 g/mL | 1.009 g/mL | 1.009 g/mL |
| pH | 1.9 to 2.1 | 2.0 | 2.0 | 2.0 | 2.0 |
| Assay - Zinc | 93.0% to 107.0% | 99.5% | 102.2% | 100.8% | 99.2% |
| Assay - Copper | 93.0% to 107.0% | 101.5% | 104.7% | 103.5% | 102.2% |
| Assay - Selenium | 93.0% to 107.0% | 96.3% | 96.3% | 98.1% | 98.6% |
| Assay - Manganese | 93.0% to 107.0% | 95.9% | 99.8% | 99.1% | 99.1% |

Prior to transferring the bulk into the aseptic processing area (APA), a sample of the bulk solution (approximately 100 mL) was taken and submitted to for bioburden testing. The results are provided in Table 28.

TABLE 28

Bioburden Results

| | | Results | | | |
|---|---|---|---|---|---|
| Test | Specifications* | RD15-013 | RD16-001 | RD16-007 | RD18-007 |
| Bioburden | NMT 10 CFU/mL | <1 CFU/mL | <1 CFU/mL | <1 CFU/mL | <1 CFU/mL |

CFU refers to colony forming units.

A pre-use water bubble point test was performed on the sterilizing grade filter to verify the integrity of the filter. Subsequently, the bulk product was passed through a 10" 1.0 μm pre-filter and transfer line to the filling room. It was continuously filtered through one 4" 0.2 μm filter and was supplied into a sterile receiving vessel in the APA Filling Line 1 or Line 3. The filtered bulk solution was filled into 2 mL Type I, sulfur treated flint glass tubular vials with 13 mm neck openings. The filled units were then stoppered with 13 mm gray West 4432, B2-40 stoppers, and sealed with 13 mm West aluminum flip-off seals with caps. A post-filtration bubble point test was performed to check the integrity of the sterilizing-grade filter.

USP lots RD15-013, RD16-001, RD16-007, and RD18-007 were filled as a 1 mL filling a 2 mL vial. Twelve consecutively filled vials were taken from the beginning, middle and end of the fil runs and gravimetrically tested to confirm fill volumes. The fill volume check sampling and results are summarized in Table 29.

TABLE 29

| | Fill Volume Results | | | | | | | | | | | |
|---|---|---|---|---|---|---|---|---|---|---|---|---|
| | Minimum: 1.16 g (1.15 mL)/Target: 1.31 g (1.3 mL)/Maximum: 1.41 g (1.4 mL) | | | | | | | | | | | |
| Acceptance | Lot # RD15-013 | | | Lot # RD16-001 | | | Lot # RD16-007 | | | Lot # RD18-007 | | |
| Criteria | Beg | Mid | End | Beg | Mid | End | Beg | Mid | End | Beg | Mid | End |
| Average (g) Intra-lot Results | 1.34 | 1.31 | 1.31 | 1.36 | 1.30 | 1.30 | 1.36 | 1.31 | 1.31 | 1.29 | 1.28 | 1.28 |
| | Average = 1.32 g (RSD = 2.7%) | | | Average = 1.32 g (RSD = 3.2%) | | | Average = 1.33 g (RSD = 2.3%) | | | Average = 1.28 g (RSD = 1.8%) | | |

Each tray of filled vials was loaded into an autoclave and the finished product was sterilized by autoclaving at 122.2° C. for 15 minutes. Following sterilization, the units were 100% inspected. A summary of the specifications and test results for the three exhibit batches and one bridging batch are provided in the Table 30.

Appropriate stability studies were initiated, and the required number of units of each exhibit batch were placed into storage at 25° C./60% RH, 30° C./65% RH, and 40° C./75% RH.

TABLE 30

| | Release Test Results for Trace Elements Injectable Composition | | | | |
|---|---|---|---|---|---|
| Test | Acceptance Criteria | Exhibit Batch RD15-013 | Exhibit Batch RD16-001 | Exhibit Batch RD16-007 | Bridging Batch RD18-007 |
| Description | Clear, colorless to slightly blue solution and is essentially free from visible particulates. | Pass | Pass | Pass | Pass |
| Identification | A. Zinc - The Assay preparation, prepared as directed in the Assay, exhibits an emission maximum at 472.215 nm when tested as directed for Procedure in the respective Assay. | Pass | Pass | Pass | Pass |
| | B. Copper - The Assay preparation, prepared as directed in the Assay, exhibits an emission maximum at 224.700 nm when tested as directed for Procedure in the respective Assay. | Pass | Pass | Pass | Pass |
| | C. Selenium - The Assay preparation, prepared as directed in the Assay, exhibits an emission maximum at 196.026 nm when tested as directed for Procedure in the respective Assay. | Pass | Pass | Pass | Pass |
| | D. Manganese - The Assay preparation, prepared as directed in the Assay, exhibits an emission maximum at 279.827 nm when tested as directed for Procedure in the respective Assay. | Pass | Pass | Pass | Pass |
| pH | <791> Between 1.5 and 3.5. | 2.0 | 2.0 | 2.0 | 2.0 |
| Assay | Zinc: It contains not less than 90.0% and not more than 110.0% of the labeled amount of Zn. (L.C. = 3 mg/mL of Zinc) | 99.0% | 102.4% | 101.7% | 98.3% |
| | Copper: It contains not less than 90.0% and not more than 110.0% of the labeled amount of Cu. (L.C. = 0.3 mg/mL of Copper) | 101.8% | 103.9% | 104.6% | 101.5% |
| | Manganese: It contains not less than 90.0% and not more than 110.0% of the labeled amount of Mn. (L.C. = 55 µg/mL of Manganese) | 96.6% | 99.0% | 99.3% | 97.8% |
| | Selenium: It contains not less than 90.0% and not more than 110.0% of the labeled amount of Se. (L.C. = 60 µg/mL of Selenium) | 96.3% | 96.8% | 98.6% | 98.3% |

TABLE 30-continued

Release Test Results for Trace Elements Injectable Composition

| Test | Acceptance Criteria | Exhibit Batch RD15-013 | Exhibit Batch RD16-001 | Exhibit Batch RD16-007 | Bridging Batch RD18-007 |
|---|---|---|---|---|---|
| Residual Solvents | <467> Meets requirements under Option 2 | Meets requirements | Meets requirements | Meets requirements | Meets requirements |
| Aluminum* (GFAAS) | Not more than 6,000 μg/L. | <1250 μg/L | <1250 μg/L | <1250 μg/L | <1250 μg/L |
| Aluminum (ICP-MS) | Not more than 6,000 μg/L. | <1880 μg/L | <1880 μg/L | <1880 μg/L | <1880 μg/L |
| Elemental Impurities: | Arsenic: Not more than 1.5 μg/mL | <0.45 μg/mL | <0.45 μg/mL | <0.45 μg/mL | <0.45 μg/mL |
| | Cadmium: Not more than 0.6 μg/mL | <0.2 μg/mL | <0.2 μg/mL | <0.2 μg/mL | <0.2 μg/mL |
| | Mercury: Not more than 0.4 μg/mL | <0.1 μg/mL | <0.1 μg/mL | <0.1 μg/mL | <0.1 μg/mL |
| | Lead: Not more than 0.5 μg/mL | <0.2 μg/mL | <0.2 μg/mL | <0.2 μg/mL | <0.2 μg/mL |
| | Chromium: Not more than 1.0 μg/mL | <0.3 μg/mL | <0.3 μg/mL | <0.3 μg/mL | <0.3 μg/mL |
| | Iron: Not more than 10 μg/mL | <3 μg/mL | <3 μg/mL | <3 μg/mL | <3 μg/mL |
| | Silicon: Not more than 100 μg/mL | <30 μg/mL | <30 μg/mL | <30 μg/mL | <30 μg/mL |
| | Magnesium: Not more than 50 μg/mL | <15 μg/mL | <15 μg/mL | <15 μg/mL | <15 μg/mL |
| | Calcium: Not more than 50 μg/mL | <15 μg/mL | <15 μg/mL | <15 μg/mL | <15 μg/mL |
| | Boron: Not more than 50 μg/mL | <15 μg/mL | <15 μg/mL | <15 μg/mL | <15 μg/mL |
| Volume of Solution | 1 mL vial: Not less than 1.0 mL. | 1.3 mL | 1.3 mL | 1.3 mL | 1.2 mL |
| Particulate Matter | <788> Meets requirements of the Light Obscuration Particle Count Test for small-volume injections, limits are: NMT 6,000 particles ≥10 μm per container NMT 600 particles ≥25 μm per container | 1 | 8 | 4 | 1 |
| | If retested by the Microscopic method limits are: NMT 3,000 particles ≥10 μm per container NMT 300 particles ≥25 μm per container | <1 | <1 | <1 | 0 |
| Sterility | <71> If no growth is observed, the article tested meets the requirements of the test for sterility. | No growth | No growth | No growth | No growth |
| Bacterial Endotoxins | <85> The Endotoxin limit is not more than 50 EU/mL. | <17.50 EU/mL | <17.50 EU/mL | <17.50 EU/mL | <17.50 EU/mL |
| Other requirements Current USP <1> | Meets requirements | N/A | N/A | N/A | N/A |

*Aluminum was tested by both, GFAAS (graphite furnace atomic absorption spectroscopy) and ICP-MS (inductively coupled plasma mass spectrometry) methods, during the ICP-MS method development and validation.

Example 8—Stability Tests

In this example, the trace elements injectable compositions, USP lots RD15-013, RD16-001, RD16-007, and RD18-007 were subjected to stability protocols as summarized in Table 31. PP-70,J 1

TABLE 31

Stability Protocols

| Stability Storage Condition | Test Station (Month) |
|---|---|
| Finished Product release | Initial (0) |
| Upright 25 ± 2° C./60% RH ± 5% RH | 3, 6, 9, 12, 18, 24 |
| Inverted 25 ± 2° C./60% RH ± 5% RH | 3, 6, 9, 12, 18, 24 |
| Upright 40 ± 2° C./75% RH ± 5% RH | 1, 3, 6 |
| Inverted 40 ± 2° C./75% RH ± 5% RH | 1, 3, 6 |

From the collected data, it can be seen that after 6-month exposure to 40° C./75% RH and 24-month exposure to 25° C./60% RH conditions, all results were stable, and met the stability specifications. The stability data confirms that the manufacturing process and container closure components chosen for the manufacture of the trace elements injectable composition, USP were acceptable. Based on the results of the 24-month stability studies and acceptable 6-month accelerated stability results for the exhibit batches, we concluded that the trace elements injectable composition, USP had a 24-month expiration dating.

On the trace elements injectable composition of this application, we also conducted photostability studies. The stability storage conditions and exposure criteria for the drug product photostability study are summarized in the following table (Table 32) in accordance with the ICH Q1B Photostability Testing Guideline recommendations.

TABLE 32

Photostability Recommendations

| Storage Condition | Exposure |
|---|---|
| 25° C. ± 2° C., Horizontal, Visible Light Exposure | Not less than 1.2 million lux hours |
| 25° C. ± 2° C., Horizontal, Near Ultraviolet (UV) Light Exposure | Not less than 200-watt hours/m² |

The protocol was designed to evaluate the drug product in its immediate packaging system under light exposure by studying the following quality attributes: pH, assay, elemental impurities, description, and particulate matter. The finished product samples from the exhibit batch Lot RD15-013 were used for this study. Photostability results for the visible and UV light exposures are provided in Tables 33 and 34, respectively.

TABLE 33

Photostability Results for Visible Light Exposure

| Test Name | Specifications | Initial[1] | Shelf I | Shelf I-Control Wrapped Vials |
|---|---|---|---|---|
| Visible Light Exposure | NLT 1.2 (million lux hours) | 0 | 1.36 | 1.36 |
| Description[2] | Conforms | Conforms | Conforms | Conforms |
| pH | 1.5-3.5 | 2.0 | 2.0 | 2.0 |
| Copper Assay | 90.0-110.0 (%) | 103.0 | 102.0 | 102.3 |
| Manganese Assay | 90.0-110.0 (%) | 97.8 | 96.8 | 97.6 |
| Zinc Assay | 90.0-110.0 (%) | 100.7 | 99.6 | 100.4 |
| Selenium Assay | 90.0-110.0 (%) | 96.5 | 97.5 | 97.3 |
| Aluminum Test (GFAA) | NMT 6000 (µg/L)[3] | <1250 | <1250 | <1250 |
| Aluminum (ICP-MS) | NMT 6000 (µg/L)[3] | <1880 | <1880 | <1880 |
| Silicon | NMT 100 (µg/mL) | <30 | <30 | <30 |
| Magnesium | NMT 50 (µg/mL) | <15 | <15 | <15 |
| Calcium | NMT 50 (µg/mL) | <15 | <15 | <15 |
| Boron | NMT 50 (µg/mL) | <15 | <15 | <15 |
| Particulate Matter 10 µm | NMT 6000 (particles/container) | 1 | 3 | 1 |
| Particulate Matter 25 µm | NMT 600 (particles/container) | <1 | <1 | <1 |

TABLE 34

Photostability Results for UV Light Exposure

| Test Name | Specifications | Initial[1] | Shelf I | Shelf I-Control Wrapped Vials |
|---|---|---|---|---|
| UV Light Exposure | NLT 200 (w/m²) | 0 | 422.34 | 422.34 |
| Description[2] | Conforms | Conforms | Conforms | Conforms |
| pH | 1.5-3.5 | 2.0 | 2.0 | 2.0 |
| Copper Assay | 90.0-110.0 (%) | 103.0 | 102.3 | 102.2 |
| Manganese Assay | 90.0-110.0 (%) | 97.8 | 96.8 | 97.1 |
| Zinc Assay | 90.0-110.0 (%) | 100.7 | 100.0 | 99.9 |
| Selenium Assay | 90.0-110.0 (%) | 96.5 | 93.5 | 94.8 |
| Aluminum Test (GFAA) | NMT 6000 (µg/L)[3] | <1250 | <1250 | <1250 |
| Aluminum (ICP-MS) | NMT 6000 (µg/L)[3] | <1880 | <1880 | <1880 |
| Silicon | NMT 100 (µg/mL) | <30 | <30 | <30 |
| Magnesium | NMT 50 (µg/mL) | <15 | <15 | <15 |
| Calcium | NMT 50 (µg/mL) | <15 | <15 | <15 |
| Boron | NMT 50 (µg/mL) | <15 | <15 | <15 |
| Particulate Matter 10 µm | NMT 6000 (particles/container) | 1 | 1 | 1 |
| Particulate Matter 25 µm | NMT 600 (particles/container) | <1 | <1 | <1 |

[1]Samples not stored in the photostability chamber.
[2]Clear colorless to slightly blue solution and is essentially free from visible particulates.
[3]Limit for Aluminum was changed from 6250 µg/mL to 6000 µg/mL after completion of this study.
NMT = Not More Than
NLT = Not Less Than The data from the photostability evaluation above indicated that all the test parameters met specifications thus confirming that the product was stable even after exposure to visible and/or UV lights.

Example 9—Comparative Trace Element Compositions

This example shows currently available trace element compositions (e.g., Multitrace®-5 concentrated) that contain zinc, copper, selenium, manganese and chromium, which is compared to the new trace element compositions of the current application (shown in Table 35 as *, **) that have reduced amounts of zinc, copper, manganese and no detectable chromium compared to the Multitrace®-5 concentrated.

TABLE 35

| Composition | Zinc | Copper | Selenium | Manganese | Chromium | Comments |
|---|---|---|---|---|---|---|
| | mcg/mL | | | | | |
| Multitrace ®-5 (Available from American Regent) | 1000 | 400 | 20 | 100 | 4 | |
| Multitrace ®-5 Concentrated (Available from American Regent) | 5000 | 1000 | 60 | 500 | 10 | |
| Multitrace ®-4 (Available from American Regent) | 1000 | 400 | NA | 100 | 4 | |
| Multitrace ®-4 Concentrated (Available from American Regent) | 5000 | 1000 | NA | 500 | 10 | |
| Multitrace ®-4 Pediatric (Available from American Regent) | 1000 | 100 | NA | 25 | 1 | |
| Multitrace ®-4 Neonatal (Available from American Regent) | 1500 | 100 | NA | 25 | 0.85 | |
| ADDAMEL ™ (Available from Frensenius Kabi) | 650 | 130 | 3.2 | 27 | 1 | Also contains Iodide (13 mcg), Fluoride (95 mcg), Molybdenum (1.9 mcg). |
| *New composition Adult/Pediatric (also in Table 6) | 3000 | 300 | 60 | 55 | NA | |
| **New composition Neonatal | 1000 | 60 | 6 | 3 | NA | |

From the Table 35, the amount of selenium for the adult Multitrace®-5 concentrated composition and the new adult/pediatric composition is the same, which is 60 mcg/mL selenium. The other trace elements in the new adult/pediatric composition are zinc, copper, and manganese, which are in reduced amounts—mainly 3000 mcg/mL zinc, 300 mcg/mL copper, 55 mcg/mL manganese, and no detectable chromium compared to the Multitrace®-5 concentrated composition.

For the new neonatal composition, compared to the Multitrace®-4 neonatal composition, the zinc, copper, and manganese are in reduced amounts—mainly 1000 mcg/mL zinc, 60 mcg/mL copper, 3 mcg/mL manganese compared to the Multitrace®-4 neonatal composition. However, the selenium for the new neonatal composition is 6 mcg/mL, which is increased.

Both the new adult/pediatric composition and the new neonatal composition have no detectable chromium, which is unlike other commercially available compositions (e.g., Addamel™, Multitrace®-5, and Multitrace®-4).

These new compositions are customized to about 80% of the respective adult/pediatric and neonatal populations that need trace element additions to the parenteral nutrition. For example, the new adult/pediatric trace element composition is customized for patients above 10 kg body weight, while the new neonatal trace element composition is customized for patients under 10 kg body weight. The new adult/pediatric trace element composition and the new neonatal trace element composition will be safer than currently available trace element products.

Further, the adult/pediatric trace element composition when added to the KABIVEN® and CLINIMIX E admixtures and stored for up to 14 days under refrigeration (2° C. to 8° C.) met the protocol's acceptance criteria and showed stability in PN after 14 days under refrigeration as discussed in Examples 1-6.

Example 10—Comparative Trace Element Compositions

TABLE 36

Recommended Weight-Based Daily Dosage of Trace Element (mL) for Pediatric Patients weighing 10 kg to 49 kg and Corresponding Amount of Each Trace Element (mcg)

| Body Weight | Recommended Weight-Based Dosage of Trace Element In Volume | Amount of Trace Element Provided by the Corresponding Trace Element Volume | | | |
|---|---|---|---|---|---|
| | | Zinc | Copper | Manganese | Selenium |
| 10 kg to 19 kg | 0.2 mL | 600 mcg | 60 mcg | 11 mcg | 12 mcg |
| 20 kg to 29 kg | 0.4 mL | 1,200 mcg | 120 mcg | 22 mcg | 24 mcg |

TABLE 36-continued

Recommended Weight-Based Daily Dosage of Trace Element
(mL) for Pediatric Patients weighing 10 kg to 49 kg
and Corresponding Amount of Each Trace Element (mcg)

| Body Weight | Recommended Weight-Based Dosage of Trace Element In Volume | Amount of Trace Element Provided by the Corresponding Trace Element Volume | | | |
|---|---|---|---|---|---|
| | | Zinc | Copper | Manganese | Selenium |
| 30 kg to 39 kg | 0.6 mL | 1,800 mcg | 180 mcg | 33 mcg | 36 mcg |
| 40 kg to 49 kg | 0.8 mL | 2,400 mcg | 240 mcg | 44 mcg | 48 mcg |

Additional Supplementation with Trace Element

For pediatric patients weighing 10 kg to 49 kg, additional zinc (in heavier patients in some weight bands), copper and selenium may be needed to meet the recommended daily dosage of these trace elements, shown below. To determine the additional amount of supplementation that is needed, compare the calculated daily recommended dosage based on the body weight of the patient to the amount of each trace element provided by Trace Element (Table 36) and other dietary sources:

Zinc: 50 mcg/kg/day (up to 3,000 mcg/day)
Copper: 20 mcg/kg/day (up to 300 mcg/day)
Selenium: 2 mcg/kg/day (up to 60 mcg/day).

Example 11—Trace Elements Composition (Tralement™)

Tralement™ is indicated in adult and pediatric patients weighing at least 10 kg as a source of zinc, copper, manganese, and selenium for parenteral nutrition when oral or enteral nutrition is not possible, insufficient, or contraindicated.

The trace element composition Tralement™ can be in a single dose vial. Each mL contains zinc about 3 mg (equivalent to zinc sulfate 7.41 mg), copper about 0.3 mg (equivalent to cupric sulfate 0.75 mg), manganese about 55 mcg (equivalent to manganese sulfate 151 mcg), selenium about 60 mcg (equivalent to selenious acid 98 mcg), and water for injection. Sulfuric acid may be added to adjust pH between 1.5 and 3.5.

In some embodiments, the zinc used in the trace element composition can be zinc heptahydrate having the molecular formula $ZnSO_4 \cdot 7H_2O$ and a molecular weight of 287.54 g/mol.

In some embodiments, the copper used in the trace element composition can be cupric sulfate that is in pentahydrate form having the molecular formula $CuSO_4 \cdot 5H_2O$ and a molecular weight of 249.69 g/mol.

In some embodiments, the manganese used in the trace element composition can be manganese sulfate that is in a monohydrate form having the molecular formula $MnSO_4 \cdot H_2O$ and a molecular weight of 169.02 g/mol.

In some embodiments, the selenium in the trace element composition can be selenious acid that has the molecular formula $H_2SeO_3 \cdot H_2O$ and a molecular weight of 128.97 g/mol.

Example 12—Trace Elements Composition (Multrys™)

The trace elements composition (Multrys™) is indicated in neonatal and pediatric patients weighing less than 10 kg as a source of zinc, copper, manganese, and selenium for parenteral nutrition when oral or enteral nutrition is not possible, insufficient, or contraindicated.

The trace elements composition (Multrys™) can contain 4 trace elements in a sterile, nonpyrogenic, clear, and colorless to slightly blue solution, that can be used as a combination of four trace elements and an additive to intravenous solutions for parenteral nutrition. In this particular embodiment of this example, it has no preservative. Each single-dose vial can contain 1 mL. *Each mL contains zinc about 1,000 mcg (equivalent to zinc sulfate 2,470 mcg), copper about 60 mcg (equivalent to cupric sulfate 150 mcg), manganese about 3 mcg (equivalent to manganese sulfate 8.22 mcg), selenium about 6 mcg (equivalent to selenious acid 9.8 mcg), and water for injection. Sulfuric acid may be added to adjust pH between 1.5 and 3.5.

Zinc sulfate can be in a heptahydrate form having the molecular formula: $ZnSO_4 \cdot 7H_2O$ and molecular weight of about 287.54 g/mol. The cupric sulfate can be in a pentahydrate form having the molecular formula: $CuSO_4 \cdot 5H_2O$ and molecular weight: 249.69 g/mol. The manganese sulfate can be in a monohydrate form and have the molecular formula: $MnSO_4 \cdot H_2O$ and molecular weight of about 169.02 g/mol. The selenious acid has the molecular formula: $H_2SeO_3$ and molecular weight of about 128.97 g/mol. In this particular embodiment of this example, the trace elements composition contains no more than 1,500 mcg/L of aluminum.

Recommended Dosage in Pediatric Patients and Monitoring Considerations

Multrys™ is a fixed-combination product. Each mL of Multrys™ provides zinc 1,000 mcg, copper 60 mcg, manganese 3 mcg, and selenium 6 mcg.

Recommended Dosage for Pediatric Patients Weighing 0.4 kg to 0.59 kg

The total recommended dosage of Multrys™ is 0.2 mL every other day.

Daily supplementation of Zinc, Copper, and Selenium will be needed to meet daily requirements (See Table B below).

Recommended Dosage for Pediatric Patients Weighing 0.6 kg to Less than 10 kg

The recommended dosage of Multrys™ is 0.3 mL/kg/day rounded to nearest 0.1 mL for up to a maximum of 1 mL per day.

The recommended volume of Multrys™ to be added to parenteral nutrition ranges from 0.2 mL per day to 1 mL per day based on body weight, see Table A below.

TABLE A

Recommended Daily Volume of Multrys™ and Corresponding Amount of Each Trace Element (mcg)

| Body Weight | Recommended Daily Volume | Amount of Trace Element Provided by the Corresponding Multrys™ Volume | | | |
|---|---|---|---|---|---|
| | | Zinc mcg | Copper mcg | Manganese mcg | Selenium mcg |
| 0.6 kg to 0.8 kg | 0.2 mL | 200 | 12 | 0.6 | 1.2 |
| 0.9 kg to 1.1 kg | 0.3 mL | 300 | 18 | 0.9 | 1.8 |
| 1.2 kg to 1.4 kg | 0.4 mL | 400 | 24 | 1.2 | 2.4 |
| 1.5 kg to 1.7 kg | 0.5 mL | 500 | 30 | 1.5 | 3 |
| 1.8 kg to 2 kg | 0.6 mL | 600 | 36 | 1.8 | 3.6 |
| 2.1 kg to 2.3 kg | 0.7 mL | 700 | 42 | 2.1 | 4.2 |
| 2.4 kg to 2.6 kg | 0.8 mL | 800 | 48 | 2.4 | 4.8 |
| 2.7 kg to 2.9 kg | 0.9 mL | 900 | 54 | 2.7 | 5.4 |
| 3 kg to 9.9 kg | 1 mL | 1,000 | 60 | 3 | 6 |

Additional Trace Element Supplementation with Multrys™

Multrys™ is recommended only for pediatric patients who require supplementation with all four of the individual trace elements (i.e., zinc, copper, manganese and selenium).

To determine the additional amount of supplementation that is needed, compare the calculated daily recommended dosage based on the body weight of the patient to the amount of each trace element provided by Multrys™ and enteral nutrition sources.

TABLE B

Daily Requirement for Trace Element Supplementation for Pediatric Patients

| Trace Element | Patient Weight (kg) | Daily Requirement* |
|---|---|---|
| Zinc | Less than 3 kg | 400 mcg/kg/day |
| | 3 kg to 5 kg | 250 mcg/kg/day |
| | 5 to 10 kg | 100 mcg/kg/day |
| Copper | — | 20 mcg/kg/day |
| Selenium | — | 2 mcg/kg/day |
| Manganese** | — | 1 mcg/kg/day |

*Multrys™ is not recommended for pediatric patients who may require a lower dosage of one or more of these individual trace elements.
**Avoid additional manganese supplementation with Multrys™ use. Accumulation of manganese in the brain can occur with long-term administration with higher than the recommended dosage of 1 mcg/kg/day.

For pediatric patients weighing less than 3 kg, Multrys™ does not provide the recommended daily dosage of zinc.

Zinc: For patients weighing less than 3 kg, add Zinc Sulfate to provide total daily recommended dose of 400 mcg/kg/day using parenteral and/or enteral routes of administration.

For pediatric patients weighing 0.4 kg to 0.59 kg and 4 kg to 9.9 kg, Multrys™ does not provide the recommended daily dosage of copper or selenium.

Copper: For patients weighing 0.4 to 0.59 kg or 4 kg to 9.9 kg, add Cupric Chloride to provide total daily recommended dose of 20 mcg/kg/day using parenteral and/or enteral routes of administration.

Selenium: For patients weighing 0.4 to 0.59 kg or 4 kg to 9.9 kg, add Selenious Acid to provide total daily recommended dose of 2 mcg/kg/day using parenteral and/or enteral routes of administration.

Monitoring

Monitor zinc, copper, and selenium serum concentrations and manganese whole blood concentrations during long-term administration of parenteral nutrition.

Low Chromium

In some embodiments, the amount of chromium in the parenteral nutrition containing the trace elements composition (e.g., Multrys™ or Tralement™) or the trace elements composition (e.g., Multrys™ or Tralement™) itself is not more than about 0.15 g/mL to not more than about 0.07 g/mL or lower. With the not more than about 0.15 g/mL of chromium, the maximum potential exposure to chromium (e.g., 0.045 g/kg/day) will be 22.5% of the maximum chromium dose that can be used for parenteral nutrition in a target patient population (e.g., children (weighing 0.4-9.9 kg)). This can be based on a target dose volume of, for example, 0.3 mL/kg/day. In some embodiments, this will reduce the risk of toxicity from total chromium exposure in the parenteral nutrition (e.g., from intentionally added chromium and chromium as an impurity).

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings. Since modifications will be apparent to those of skill in the art, it is intended that this disclosure be limited only by the scope of the appended claims.

What is claimed is:

1. A method of supplementing trace elements to an adult or pediatric human patient in need thereof, the method comprising administering an injectable trace element composition to the patient, the injectable trace element composition comprising water, about 3,000 μg of zinc, about 300 μg of copper, about 60 μg of selenium, and about 55 μg of manganese per 1 mL of the injectable trace element composition, wherein the injectable trace element composition contains no iron or iron in an amount not to exceed 10 μg, no chromium or chromium in an amount not to exceed 1 μg and no aluminum or aluminum in an amount not to exceed 6 μg per 1 mL of the injectable trace element composition.

2. The method of claim 1, wherein the injectable trace element composition comprises 3,000 μg of zinc, 300 μg of copper, 60 μg of selenium, and 55 μg of manganese per 1 mL of the injectable trace element composition.

3. The method of claim 1, wherein the injectable trace element composition consists essentially of water, about 3,000 μg of zinc, about 300 μg of copper, about 60 μg of selenium, about 55 μg of manganese and optionally sulfuric acid per 1 mL of the injectable trace element composition.

4. The method of claim 1, wherein the injectable trace element composition consists of water, about 3,000 μg of zinc, about 300 μg of copper, about 60 μg of selenium, about 55 μg of manganese and optionally sulfuric acid per 1 mL of the injectable trace element composition.

5. The method of claim 1, wherein the zinc, copper, selenium, and manganese are active ingredients in the injectable trace element composition.

6. The method of claim 1, wherein the zinc is elemental zinc from zinc sulfate or zinc sulfate heptahydrate, the copper is elemental copper from cupric sulfate or cupric sulfate pentahydrate, the manganese is elemental manganese from manganese sulfate or manganese sulfate monohydrate and the selenium is elemental selenium from selenious acid.

7. The method of claim 1, wherein the injectable trace element composition contains from 0 µg to 0.5 µg of chromium per 1 mL of the injectable trace element composition.

8. The method of claim 1, wherein the injectable trace element composition is administered to the adult or pediatric human patient and is a source of zinc, copper, manganese, and selenium when added to parenteral nutrition.

9. The method of claim 7, wherein the injectable trace element composition contains impurities of aluminum in an amount not to exceed 6 µg per 1 mL of the injectable trace element composition.

10. The method of claim 1, wherein the injectable trace element composition further comprises (i) at least one of silicon from about 0.0001 µg to about 100 µg, magnesium from about 0.0001 µg to about 50 µg, calcium from about 0.0001 µg to about 50 µg, or from about 0.0001 µg to about 50 µg per 1 mL of the injectable trace element composition; or (ii) at least one of silicon from about 0 µg to about 100 µg, magnesium from about 0 µg to about 50 µg, calcium from about 0 µg to about 50 µg, or boron from about 0 µg to about 50 µg per 1 mL of the injectable trace element composition.

11. The method of claim 1, wherein the injectable trace element composition has a pH of about 1.0 to about 5.0.

12. A method of supplementing trace elements to an adult or pediatric human patient in need thereof, the method comprising administering to the patient a trace element composition, the trace element composition comprising water, about 7.41 mg of zinc sulfate or zinc sulfate heptahydrate, about 0.75 mg of cupric sulfate or cupric sulfate pentahydrate, about 151 µg of manganese sulfate or manganese sulfate monohydrate and about 98 µg of selenious acid per 1 mL of the trace element composition, wherein the trace element composition contains no iron or iron in an amount not to exceed 10 µg, no chromium or chromium in an amount not to exceed 1 µg and no aluminum or aluminum in an amount not to exceed 6 µg per 1 mL of the trace element composition.

13. The method of claim 12, wherein the trace element composition contains less than about 0.5 µg ug/mL of chromium per 1 mL of the trace element composition.

14. The method of claim 12, wherein the trace element composition consists essentially of water, about 7.41 mg of zinc sulfate or zinc sulfate heptahydrate, about 0.75 mg of cupric sulfate or cupric sulfate pentahydrate, about 151 µg of manganese sulfate or manganese sulfate monohydrate, about 98 µg of selenious acid and optionally sulfuric acid per 1 mL of the trace element composition.

15. The method of claim 12, wherein the trace element composition consists of water, about 7.41 mg of zinc sulfate or zinc sulfate heptahydrate, about 0.75 mg of cupric sulfate or cupric sulfate pentahydrate, about 151 ug of manganese sulfate or manganese sulfate monohydrate, about 98 µg of selenious acid and optionally sulfuric acid per 1 mL of the trace element composition.

16. The method of claim 12, wherein the trace element composition is injectable and has a pH of about 1.0 to about 5.0.

17. The method of claim 12, wherein the trace element composition contains from 0 µg to 0.5 µg of chromium per 1 mL of the trace element composition.

18. The method of claim 17, wherein the trace element composition contains impurities of aluminum in an amount not to exceed 6 µg per 1 mL of the trace element composition.

19. A method of supplementing trace elements to a pediatric or neonatal human patient in need thereof, the method comprising administering a trace element composition to the patient, the trace element composition comprising water, about 1,000 µg of zinc, about 60 µg of copper, about 6 µg of selenium, and about 3 µg of manganese per 1 mL of the trace element composition, wherein the trace element composition contains no iron or iron in an amount not to exceed 10 µg, no chromium or chromium in an amount not to exceed 1 µg and no aluminum or aluminum in an amount not to exceed 6 µg per 1 mL of the trace element composition.

20. The method of claim 19, wherein the trace element composition consists essentially of water, about 1,000 µg of zinc, about 60 µg of copper, about 6 µg of selenium, about 3 µg of manganese and optionally sulfuric acid per 1 mL of the trace element composition.

21. The method of claim 19, wherein the trace element composition consists of water, about 1,000 µg of zinc, about 60 µg of copper, about 6 µg of selenium, about 3 µg of manganese and optionally sulfuric acid per 1 mL of the trace element composition.

22. The method of claim 19, wherein the zinc, copper, manganese, and selenium are active ingredients in the trace element composition.

23. The method of claim 19, wherein the trace element composition is injectable and contains from 0 µg to 0.5 µg of chromium per 1 mL of the trace element composition.

24. The method of claim 19, wherein the trace element composition is administered to a pediatric or neonatal human patient and is a source of zinc, copper, manganese, and selenium when added to parenteral nutrition.

25. The method of claim 19, wherein the trace element composition contains impurities of aluminum in an amount not to exceed 6 µg per 1 mL of the trace element composition.

26. A method of supplementing trace elements to a pediatric or neonatal human patient in need thereof, the method comprising administering to the patient an injectable trace element composition comprising water, about 2,470 µg of zinc sulfate or zinc sulfate heptahydrate, about 150 µg of cupric sulfate or cupric sulfate pentahydrate, about 8.22 µg of manganese sulfate or manganese sulfate monohydrate, and about 9.8 µg of selenious acid per 1 mL of the injectable trace element composition, wherein the injectable trace element composition contains no iron or iron in an amount not to exceed 10 82 g, no chromium or chromium in an amount not to exceed 1 µg and no aluminum or aluminum in an amount not to exceed 6 µg per 1 mL of the injectable trace element composition.

27. The method of claim 26, wherein the injectable trace element composition consists essentially of water, about 2,470 µg of zinc sulfate or zinc sulfate heptahydrate, about 150 µg of cupric sulfate or cupric sulfate pentahydrate, about 8.22 µg of manganese sulfate or manganese sulfate monohydrate, about 9.8 µg of selenious acid and optionally sulfuric acid per 1 mL of the injectable trace element composition.

28. The method of claim 26, wherein the injectable trace element composition consists of water, about 2,470 µg of zinc sulfate or zinc sulfate heptahydrate, about 150 µg of cupric sulfate or cupric sulfate pentahydrate, about 8.22 µg of manganese sulfate or manganese sulfate monohydrate, about 9.8 µg of selenious acid and optionally sulfuric acid per 1 mL of the injectable trace element composition.

29. The method of claim 26, wherein the zinc sulfate or zinc sulfate heptahydrate, cupric sulfate or cupric sulfate pentahydrate, manganese sulfate or manganese sulfate monohydrate, and selenious acid are active ingredients in the injectable trace element composition.

30. The method of claim 19, wherein the trace element composition further comprises (i) at least one of silicon from about 0.0001 µg to about 100 µg, magnesium from about 0.0001 µg to about 50 µg, calcium from about 0.0001 µg to about 50 µg, boron from about 0.0001 µg to about 50 µg per 1 mL of the trace element composition; or (ii) at least one of silicon from about 0 µg to about 100 µg, magnesium from about 0 µg to about 50 µg, calcium from about 0 µg to about 50 µg, or boron from about 0 µg to about 50 µg per 1 mL of the trace element composition.

\* \* \* \* \*